US005576000A

United States Patent [19]
Reitz, Jr. et al.

[11] Patent Number: 5,576,000
[45] Date of Patent: Nov. 19, 1996

[54] MOLECULAR CLONES OF HIV-1 VIRAL STRAINS MH-ST1 AND BA-L, AND USES THEREOF

[75] Inventors: Marvin S. Reitz, Jr., Derwood, Md.; Genoveffa Franchini, Washington, D.C.; Phillip D. Markham, Rockville, Md.; Robert C. Gallo, Bethesda, Md.; Franco C. Lori, Bethesda, Md.; Mikulas Popovic, Bethesda, Md.; Suzanne Gartner, N. Potomac, Md.

[73] Assignee: The United States of America as represented by the Department of Health and Human Services, Washington, D.C.

[21] Appl. No.: 388,809

[22] Filed: Feb. 15, 1995

Related U.S. Application Data

[62] Division of Ser. No. 22,835, Feb. 25, 1993, Pat. No. 5,420,030, which is a continuation of Ser. No. 599,491, Oct. 17, 1990, abandoned.

[51] Int. Cl.⁶ .................................................. A61K 39/21
[52] U.S. Cl. .......................... 424/188.1; 424/184.1; 424/204.1; 424/207.1; 424/208.1; 530/350; 530/388.3; 530/388.35; 435/5; 435/7.1; 435/974
[58] Field of Search .................... 530/350, 388.3, 530/388.35; 435/5, 7.1, 236, 974; 424/184.1, 188.1, 204.1, 207.1, 208.1

*Primary Examiner*—Christine M. Nucker
*Assistant Examiner*—Jeffrey Stucker
*Attorney, Agent, or Firm*—Morgan & Finnegan, LLP

[57] ABSTRACT

The present invention relates to the HIV-1 strains MN-ST1 and BA-L which are typical United States HIV-1 isotypes. The present invention relates to DNA segments encoding the envelope protein of MN-ST 1 or BA-L, to DNA constructs containing such DNA segments and to host cells transformed with such constructs. The viral isolates and envelope proteins of the present invention are of value for use in vaccines and bioassays for the detection of HIV-1 infection in biological samples, such as blood bank samples.

5 Claims, 54 Drawing Sheets

Figure 2A

```
          10         20         30         40         50         60
   TGGAAGGGCT AATTCACTCC CAACGAAGAC AAGATATCCT TGATCTGTGG ATCTACCACA 70         80         90        100        110        120
   CACAAGGCTA CTTCCCTGAT TAGCAGAACT ACACACCAGG GCCAGGGATC AGATATCCAC 130        140        150        160        170        180
   TGACCTTTGG ATGGTGCTAC AAGCTAGTAC CAGTTGAGCC AGAGAAGTTA GAAGAAGCCA 190        200        210        220        230        240
   ACAAAGGAGA GAACACCAGC TTGTTACACC CTGTGAGCCT GCATGGAATG GATGACCCGG 250        260        270        280        290        300
   AGAGAGAAGT GTTAGAGTGG AGGTTTGACA GCCGCCTAGC ATTTCATCAC ATGGCCCGAG 310        320        330        340        350        360
   AGCTGCATCC GGAGTACTTC AAGAACTGCT GACATCGAGC TTGCTACAAG GGACTTTCCG 370        380        390        400        410        420
   CTGGGGACTT TCCAGGGAGG CGTGGCCTGG GCGGGACTGG GGAGTGGCGA GCCCTCAGAT 430        440        450        460        470        480
   CCTGCATATA AGCAGCTGCT TTTTGCCTGT ACTGGGTCTC TCTGGTTAGA CCAGATCTGA 490        500        510        520        530        540
   GCCTGGGAGC TCTCTGGCTA ACTAGGGAAC CCACTGCTTA AGCCTCAATA AAGCTTGCCT 550        560        570        580        590        600
   TGAGTGCTTC AAGTAGTGTG TGCCCGTCTG TTATGTGACT CTGGTAGCTA GAGATCCCTC 610        620        630        640        650        660
   AGATCCTTTT AGGCAGTGTG GAAAATCTCT AGCAGTGGCG CCCGAACAGG GACTTGAAAG 670        680        690        700        710        720
   CGAAAGAAAA ACCAGAGCTC TCTCGACGCA GGACTCGGCT TGCTGAAGCG CGCACGGCAA 730        740        750        760        770        780
   GAGGCGAGGG GCGGCGACTG GTGAGTACGC CAAAAATTCT TGACTAGCGG AGGCTAGAAG 790        800        810        820        830        840
   GAGAGAGATG GGTGCGAGAG CGTCGGTATT AAGCGGGGGA GAATTAGATC GATGGGAAAA 850        860        870        880        890        900
   CATTCGGTTA AGGCCAGGGG GAAAGAAAAA ATATAAATTA AAACATGTAG TATGGGCAAG 910        920        930        940        950        960
   CAGGGAGCTA GAACGATTCG CAGTCAATCC TGGCCTGTTA GAAACATCAG AAGGCTGTAG 970        980        990       1000       1010       1020
   ACAAATACTG GGACAGCTAC AACCATCCCT TCAGACAGGA TCAGAAGAAC TTAAATCATT 1030       1040       1050       1060       1070       1080
   ATATAATACA GTAGCAACCC TCTATTGTGT GCATCAAAAG ATAGAGATAA AAGACACCAA 1090       1100       1110       1120       1130       1140
   GGAAGCTTTA GAGAAAATAG AGGAAGAGCA AAACAAAAGT AAGAAAAAAG CACAGCAAGC 1150       1160       1170       1180       1190       1200
   AGCAGCTGAC ACAGGAAACA GAGGAAACAG CAGCCAAGTC AGCCAAAATT ACCCCATAGT 1210       1220       1230       1240       1250       1260
   GCAGAACATC GAGGGGCAAA TGGTACATCA GGCCATATCA CCTAGAACTT TAAATGCATG
```

Figure 2B

```
          1270       1280       1290       1300       1310       1320
     GGTAAAAGTA GTAGAAGAGA AGGCTTTCAG CCCAGAAGTA ATACCCATGT TTTCAGCATT 1330       1340       1350       1360       1370       1380
     ATCAGAAGGA GCCACCCCAC AAGATTTAAA CACCATGCTA AACACAGTGG GGGGACATCA 1390       1400       1410       1420       1430       1440
     AGCAGCCATG CAAATGTTAA AAGAGACCAT CAATGAGGAA GCTGCAGAAT GGGATAGATT 1450       1460       1470       1480       1490       1500
     GCATCCAGTG CATGCAGGGC CTATTACACC AGGCCAGATG AGAGAACCAA GGGGAAGTGA 1510       1520       1530       1540       1550       1560
     CATAGCAGGA ACTACTAGTA CCCTTCAGGA ACAAATAGGA TGGATGACAA ATAATCCACC 1570       1580       1590       1600       1610       1620
     TATCCCAGTA GGAGAAATCT ATAAAGATG GATAATCCTG GATTAAATA AAATAGTAAG 1630       1640       1650       1660       1670       1680
     GATGTATAGC CCTTCCAGCA TTCTGGACAT AAGACAAGGA CCAAAGGAAC CCTTTAGAGA 1690       1700       1710       1720       1730       1740
     CTATGTAGAC CGGTTCTATA AAACTCTAAG AGCCGAGCAA GCTTCACAGG AGGTAAAAAA 1750       1760       1770       1780       1790       1800
     CCGGACGACA GAAACCTTGT TGGTCCAAAA TGCGAACCCA GATTGTAAGA CTATTTTAAA 1810       1820       1830       1840       1850       1860
     AGCATTGGGA CCAGCAGCTA CACTAGAAGA AATGATGACA GCATGTCAGG GAGTGGGAGG 1870       1880       1890       1900       1910       1920
     ACCTGGTCAT AAAGCAAGAG TTTTGGCGGA AGCGATGAGC CAAGTAACAA ATTCAGCTAC 1930       1940       1950       1960       1970       1980
     CATAATGATG CAGAGAGGCA ATTTTAGGAA TCAAAGAAAG ATTATCAAGT GCTTCAATTG 1990       2000       2010       2020       2030       2040
     TGGCAAAGAA GGGCACATAG CCAAAAATTG CAGGGCCCCT AGGAAAAGGG GCTGTTGGAA 2050       2060       2070       2080       2090       2100
     ATGTGGAAAG GAAGGACACC AAATGAAAGA TTGTACTGAG AGACAGGCTA ATTTTTTAGG 2110       2120       2130       2140       2150       2160
     GAAGATCTGG CCTTCCTGCA AGGGAAGGCG GAATTTTCCT CAGAGCAGAA CAGAGCCAAC 2170       2180       2190       2200       2210       2220
     AGCCCCACCA GAAGAGAGCT TCAGGTTTGG GGAAGAGACA ACAACTCCCT ATCAGAAGCA 2230       2240       2250       2260       2270       2280
     GGAGAAGAAG CAGGAGACGA TAGACAAGGA CCTGTATCCT TTAGCTTCCC TCAAATCACT 2290       2300       2310       2320       2330       2340
     CTTTGGCAAC GACCCATTGT CACAATAAAG ATAGGGGGGC AACTAAAGGA AGCTCTATTA 2350       2360       2370       2380       2390       2400
     GATACAGGAG CAGATGATAC AGTATTAGGA GAAATGAATT TGCCAAGAAG ATGGAAACCA 2410       2420       2430       2440       2450       2460
     AAAATGATAG GGGGAATTGG AGGTTTTATC AAAGTAAGAC AGTATGATCA GATAACCATA 2470       2480       2490       2500       2510       2520
     GGAATCTGTG GACATAAAGC TATAGGTACA GTATTAGTAG GACCTACACC TGTCAACATA
```

Figure 2C

```
          2530       2540       2550       2560       2570       2580
     ATTGGAAGAA ATCTGTTGAC TCAGCTTGGG TGCACTTTAA ATTTTCCCAT TAGTCCTATT 2590       2600       2610       2620       2630       2640
     GAAACTGTAC CAGTAAAATT AAAGCCAGGA ATGGATGGCC CAAAAGTTAA ACAATGGCCA 2650       2660       2670       2680       2690       2700
     TTGACAGAAG AAAAAATAAA AGCATTAATA GAAATTTGTA CAGAAATGGA AAAGGAAGGG 2710       2720       2730       2740       2750       2760
     AAAATTTCAA AAATTGGGCC TGAAAATCCA TACAATACTC CAGTATTTGC CATAAAGAAA 2770       2780       2790       2800       2810       2820
     AAAGACAGTA CTAAATGGAG AAAATTAGTA GATTTCAGAG AACTTAATAA GAAAACTCAA 2830       2840       2850       2860       2870       2880
     GACTTCTGGG AAGTTCAATT AGGAATACCA CATCCTGCAG GGTTAAAAAA GAAAAAATCA 2890       2900       2910       2920       2930       2940
     GTAACAGTAC TGGATGTGGG TGATGCATAT TTTTCAGTTC CCTTAGATAA AGACTTCAGG 2950       2960       2970       2980       2990       3000
     AAGTATACTG CATTTACCAT ACCTAGTATA AACAATGAAA CACCAGGGAT TAGATATCAG 3010       3020       3030       3040       3050       3060
     TACAATGTGC TTCCACAGGG ATGGAAAGGA TCACCAGCAA TATTCCAAAG TAGCATGACA 3070       3080       3090       3100       3110       3120
     AAAATCTTAG AGCCTTTTAG AAAACAAAAT CCAGACATAG TTATCTATCA ATACATGGAT 3130       3140       3150       3160       3170       3180
     GATTTGTATG TAGGATCTGA CTTAGAAATA GGGCAGCATA GAGCAAAAAT AGAGGAACTG 3190       3200       3210       3220       3230       3240
     AGACGACATC TGTTGAGGTG GGGATTTACC ACACCAGACA AAAAACATCA GAAAGAACCT 3250       3260       3270       3280       3290       3300
     CCATTCCTTT GGATGGGTTA TGAACTCCAT CCTGATAAAT GGACAGTACA GCCTATAGTG 3310       3320       3330       3340       3350       3360
     CTACCAGAAA AAGACAGCTG GACTGTCAAT GACATACAGA AGTTAGTGGG AAAATTGAAT 3370       3380       3390       3400       3410       3420
     TGGGCAAGTC AGATTTACGC AGGGATTAAA GTAAAGCAAT TATGTAAACT CCTTAGAGGA 3430       3440       3450       3460       3470       3480
     ACCAAAGCAC TAACAGAAGT AATACCACTA ACAGAAGAAG CAGAGCTAGA ACTGGCAGAA 3490       3500       3510       3520       3530       3540
     AACAGGGAAA TTCTAAAAGA ACCAGTACAT GGAGTGTATT ATGACCCATC AAAAGACTTA 3550       3560       3570       3580       3590       3600
     ATAGCAGAAG TACAGAAGCA GGGGCAAGGC CAATGGACAT ATCAAATTTA TCAAGAGCCA 3610       3620       3630       3640       3650       3660
     TTTAAAAATC TGAAAACAGG CAAATATGCA AGAATGAGGG GTGCCCACAC TAATGATGTA 3670       3680       3690       3700       3710       3720
     AAACAATTAA CAGAGGCAGT GCAAAAAATA GCCACAGAAA GCATAGTAAT ATGGGGAAAG 3730       3740       3750       3760       3770       3780
     ACTCCTAAAT TTAGACTACC CATACAAAAA GAAACATGGG AAACATGGTG GACAGAGTAT
```

Figure 2D

```
        3790       3800       3810       3820       3830       3840
   ACGTAAGCCA CCTGGATTCC TGAGTGGGAG GTTGTCAATA CCCCTCCCTT AGTGAAATTA 3850       3860       3870       3880       3890       3900
   TGGTACCAGT TAGAGAAAGA ACCCATAGTA GGTGCAGAAA CTTTCTATGT AGATGGGGCA 3910       3920       3930       3940       3950       3960
   GCTAACAGGG AGACTAAAAA AGGAAAAGCA GGATATGTTA CTAACAGAGG AAGACAAAAG 3970       3980       3990       4000       4010       4020
   GTTGTCTCCC TAACTGACAC AACAAATCAG AAGACTGAGT TACAAGCAAT TCATCTAGCT 4030       4040       4050       4060       4070       4080
   TTGCAAGATT CAGGGTTAGA AGTAAACATA GTAACAGACT CACAATATGC ATTAGGAATC 4090       4100       4110       4120       4130       4140
   ATTCAAGCAC AACCAGATAA AAGTGAATCA GAGTTAGTCA GTCAAATAAT AGAGCAGTTA 4150       4160       4170       4180       4190       4200
   ATAAAAAAGG AAAAGGTCTA TCTGGCATGG GTACCAGCAC ACAAAGGAAT TGGAGGAAAT 4210       4220       4230       4240       4250       4260
   GAACAAGTAG ATAAATTAGT CAGTGCTGGA ATCAGGAAAG TACTATTTTT AGATGGAATA 4270       4280       4290       4300       4310       4320
   GATAAGGCCC AAGAAGACCA TGAGAAATAT CACAGTAATT GGAGAGCAAT GGCTAGTGAC 4330       4340       4350       4360       4370       4380
   TTTAACCTAC CACCTATAGT AGCAAAAGAA ATAGTAGCCA GCTGTGATAA ATGTCAGCTA 4390       4400       4410       4420       4430       4440
   AAAGGAGAAG CCATGCATGG ACAAGTAGAC TGTAGTCCAG GAATATGGCA ACTAGATTGT 4450       4460       4470       4480       4490       4500
   ACACATTTAG AAGGAAAAGT TATCCTGGTA GCAGTTCATG TAGCCAGTGG ATACATAGAA 4510       4520       4530       4540       4550       4560
   GCAGAAGTTA TTCCAGCAGA GACAGGGCAG GAGACAGCAT ACTTTCTCTT AAAATTAGCA 4570       4580       4590       4600       4610       4620
   GGAAGATGGC CAGTAAAAAC AATACATACA GACAATGGCC CCAATTTCAC CAGTACTACG 4630       4640       4650       4660       4670       4680
   GTTAAGGCCG CCTGTTGGTG GACGGGAATC AAGCAGGAAT TTGGCATTCC CTACAATCCC 4690       4700       4710       4720       4730       4740
   CAAAGTCAAG GAGTAATAGA ATCTATGAAT AAAGAATTAA AGAAAATTAT AGGACAGGTA 4750       4760       4770       4780       4790       4800
   AGAGATCAGG CTGAACATCT TAAGAGAGCA GTACAAATGG CAGTATTCAT CCACAATTTT 4810       4820       4830       4840       4850       4860
   AAAAGAAAAG GGGGGATTGG GGGGTACAGT GCAGGGGAAA GAATAGTAGG CATAATAGCA 4870       4880       4890       4900       4910       4920
   ACAGACATAC AAACTAAAGA ACTACAAAAA CAAATTACAA AAATTCAAAA TTTTCGGGTT 4930       4940       4950       4960       4970       4980
   TATTACAGGG ACAGCAGAGA TCCACTTTGG AAAGGACCAG CAAAGCTTCT CTGGAAAGGT 4990       5000       5010       5020       5030       5040
   GAAGGGGCAG TAGTAATACA AGATAATAAT GACATAAAAG TAGTGCCAAG AAGAAAAGCA
```

Figure 2E

```
          5050       5060       5070       5080       5090       5100
     AAGGTCATTA GGGATTATGG AAAACAGACG GCAGGTGATG ATTGTGTGGC AAGCAGACAG 5110       5120       5130       5140       5150       5160
     GATGAGGATT AGAACATGGA AAAGTTTAGT AAAACACCAT ATGTATATTT CAAAGAAAGC 5170       5180       5190       5200       5210       5220
     TAAAGGACGG TTTTATAGAC ATCACTATGA AAGCACTCAT CCAAGAATAA GTTCAGAAGT 5230       5240       5250       5260       5270       5280
     ACACATCCCA CTAGGGGATG CTAGATTGGT AATAACAACA TATTGGGGTC TGCATACAGG 5290       5300       5310       5320       5330       5340
     AGAAAGAGAC TGGCATTTAG GTCAGGGAGT CTCCATAGAA TGGAGGAAAA AGAGATATAG 5350       5360       5370       5380       5390       5400
     CACACAAGTA GACCCTGACC TAGCAGACCA CCTAATTCAT CTGCATTACT TTGATTGTTT 5410       5420       5430       5440       5450       5460
     TTCAGACTCT GCCATAAGAA AGGCCATATT AGGACATAGA GTTAGTCCTA TTTGTGAATT 5470       5480       5490       5500       5510       5520
     TCAAGCAGGA CATAACAAGG TAGGACCTCT ACAGTACTTG GCACTAACAG CATTAATAAC 5530       5540       5550       5560       5570       5580
     ACCAAAAAAG ATAAAGCCAC CTTTGCCTAG TGTTAAGAAA CTGACAGAGG ATAGATGGAA 5590       5600       5610       5620       5630       5640
     CAAGCCCCAG AAGACCAAGG GCCACAGAGG GAGCCATACA ATCAATGGGC ACTAGAGCTT 5650       5660       5670       5680       5690       5700
     TTAGAGGAGC TTAAGAATGA AGCTGTTAGA CATTTTCCTA GGATATGGCT CCATGGCTTA 5710       5720       5730       5740       5750       5760
     GGGCAACATA TCTATGAAAC TTATGGGGAT ACTTGGGCAG GAGTGGAAGC CATAATAAGA 5770       5780       5790       5800       5810       5820
     ATTCTACAAC AACTGCTGTT TATTCATTTC AGAATTGGGT GTCGACATAG CAGAATAGGC 5830       5840       5850       5860       5870       5880
     ATTATTCGAC AGAGGAGAGC AAGAAATGGA GCCAGTAGAT CCTAGACTAG AGCCCTGGAA 5890       5900       5910       5920       5930       5940
     GCATCCAGGA AGTCAGCCTA AGACTGCTTG TACCACTTGC TATTGTAAAA AGTGTTGCTT 5950       5960       5970       5980       5990       6000
     TCATTGCCAA GTTTGTTTCA CAAAAAAAGC CTTAGGCATC TCCTATGGCA GGAAGAAGCG 6010       6020       6030       6040       6050       6060
     GAGACAGCGA CGAAGAGCTC CTGAAGACAG TCAGACTCAT CAAGTTTCTC TACCAAAGCA 6070       6080       6090       6100       6110       6120
     GTAAGTAGTA CATGTAATGC AACCTTTAGT AATAGCAGCA ATAGTAGCAT TAGTAGTAGC 6130       6140       6150       6160       6170       6180
     AGGAATAATA GCAATAGTTG TGTGATCCAT AGTATTCATA GAATATAGGA AAATAAGAAG 6190       6200       6210       6220       6230       6240
     ACAAAGAAAA ATAGACAGGT TAATTGATAG AATAAGCGAA AGAGCAGAAG ACAGTGGCAA 6250       6260       6270       6280       6290       6300
     TGAGAGTGAA GGGGATCAGG AGGAATTATC AGCACTGGTG GGGATGGGGC ACGATGCTCC
```

Figure 2F

```
          6310       6320       6330       6340       6350       6360
     TTGGGTTATT AATGATCTGT AGTGCTACAG AAAAATTGTG GGTCACAGTC TATTATGGGG 6370       6380       6390       6400       6410       6420
     TACCTGTGTG GAAAGAAGCA ACCACCACTC TATTTTGTGC ATCAGATGCT AAAGCATATG 6430       6440       6450       6460       6470       6480
     ATACAGAGGT ACATAATGTT TGGGCCACAC AAGCCTGTGT ACCCACAGAC CCCAACCCAC 6490       6500       6510       6520       6530       6540
     AAGAAGTAGA ATTGGTAAAT GTGACAGAAA ATTTTAACAT GTGGAAAAAT AACATGGTAG 6550       6560       6570       6580       6590       6600
     AACAGATGCA TGAGGATATA ATCAGTTTAT GGGATCAAAG CCTAAAGCCA TGTGTAAAAT 6610       6620       6630       6640       6650       6660
     TAACCCCACT CTGTGTTACT TTAAATTGCA CTGATTTGAG GAATACTACT AATACCAATA 6670       6680       6690       6700       6710       6720
     ATAGTACTGC TAATAACAAT AGTAATAGCG AGGGAACAAT AAAGGGAGGA GAAATGAAAA 6730       6740       6750       6760       6770       6780
     ACTGCTCTTT CAATATCACC ACAAGCATAA GAGATAAGAT GCAGAAAGAA TATGCACTTC 6790       6800       6810       6820       6830       6840
     TTTATAAACT TGATATAGTA TCAATAGATA ATGATAGTAC CAGCTATAGG TTGATAAGTT 6850       6860       6870       6880       6890       6900
     GTAATACCTC AGTCATTACA CAAGCTTGTC CAAAGATATC CTTTGAGCCA ATTCCCATAC 6910       6920       6930       6940       6950       6960
     ACTATTGTGC CCCGGCTGGT TTTGCGATTC TAAAATGTAA CGATAAAAAG TTCAGTGGAA 6970       6980       6990       7000       7010       7020
     AAGGATCATG TAAAAATGTC AGCACAGTAC AATGTACACA TGGAATTAGG CCAGTAGTAT 7030       7040       7050       7060       7070       7080
     CAACTCAACT GCTGTTAAAT GGCAGTCTAG CAGAAGAAGA GGTAGTAATT AGATCTGAGA 7090       7100       7110       7120       7130       7140
     ATTTCACTGA TAATGCTAAA ACCATCATAG TACATCTGAA TGAATCTGTA CAAATTAATT 7150       7160       7170       7180       7190       7200
     GTACAAGACC CAACTACAAT AAAAGAAAAA GGATACATAT AGGACCAGGG AGAGCATTTT 7210       7220       7230       7240       7250       7260
     ATACAACAAA AAATATAATA GGAACTATAA GACAAGCACA TTGTAACATT AGTAGAGCAA 7270       7280       7290       7300       7310       7320
     AATGGAATGA CACTTTAAGA CAGATAGTTA GCAAATTAAA AGAACAATTT AAGAATAAAA 7330       7340       7350       7360       7370       7380
     CAATAGTCTT TAATCAATCC TCAGGAGGGG ACCCAGAAAT TGTAATGCAC AGTTTTAATT 7390       7400       7410       7420       7430       7440
     GTGGAGGGGA ATTTTTCTAC TGTAATACAT CACCACTGTT TAATAGTACT TGGAATGGTA 7450       7460       7470       7480       7490       7500
     ATAATACTTG GAATAATACT ACAGGGTCAA ATAACAATAT CACACTTCAA TGCAAAATAA 7510       7520       7530       7540       7550       7560
     AACAAATTAT AAACATGTGG CAGGAAGTAG GAAAAGCAAT GTATGCCCCT CCCATTGAAG
```

Figure 2G

```
            7570       7580       7590       7600       7610       7620
      GACAAATTAG ATGTTCATCA AATATTACAG GGCTACTATT AACAAGAGAT GGTGGTAAGG 7630       7640       7650       7660       7670       7680
      ACACGGACAC GAACGACACC GAGATCTTCA GACCTGGAGG AGGAGATATG AGGGACAATT 7690       7700       7710       7720       7730       7740
      GGAGAAGTGA ATTATATAAA TATAAAGTAG TAACAATTGA ACCATTAGGA GTAGCACCCA 7750       7760       7770       7780       7790       7800
      CCAAGGCAAA GAGAAGAGTG GTGCAGAGAG AAAAAAGAGC AGCGATAGGA GCTCTGTTCC 7810       7820       7830       7840       7850       7860
      TTGGGTTCTT AGGAGCAGCA GGAAGCACTA TGGGCGCAGC GTCAGTGACG CTGACGGTAC 7870       7880       7890       7900       7910       7920
      AGGCCAGACT ATTATTGTCT GGTATAGTGC AACAGCAGAA CAATTTGCTG AGGGCCATTG 7930       7940       7950       7960       7970       7980
      AGGCGCAACA GCATATGTTG CAACTCACAG TCTGGGGCAT CAAGCAGCTC CAGGCAAGAG 7990       8000       8010       8020       8030       8040
      TCCTGGCTGT GGAAAGATAC CTAAAGGATC AACAGCTCCT GGGGTTTTGG GGTTGCTCTG 8050       8060       8070       8080       8090       8100
      GAAAACTCAT TTGCACCACT ACTGTGCCTT GGAATGCTAG TTGGAGTAAT AAATCTCTGG 8110       8120       8130       8140       8150       8160
      ATGATATTTG GAATAACATG ACCTGGATGC AGTGGGAAAG AGAAATTGAC AATTACACAA 8170       8180       8190       8200       8210       8220
      GCTTAATATA CTCATTACTA GAAAAATCGC AAACCCAACA AGAAAAGAAT GAACAAGAAT 8230       8240       8250       8260       8270       8280
      TATTGGAATT GGATAAATGG GCAAGTTTGT GGAATTGGTT TGACATAACA AATTGGCTGT 8290       8300       8310       8320       8330       8340
      GGTATATAAA AATATTCATA ATGATAGTAG GAGGCTTGGT AGGTTTAAGA ATAGTTTTTG 8350       8360       8370       8380       8390       8400
      CTGTACTTTC TATAGTGAAT AGAGTTAGGC AGGGATACTC ACCATTGTCG TTGCAGACCC 8410       8420       8430       8440       8450       8460
      GCCCCCCAGT TCCGAGGGGA CCCGACAGGC CCGAAGGAAT CGAAGAAGAA GGTGGAGAGA 8470       8480       8490       8500       8510       8520
      GAGACAGAGA CACATCCGGT CGATTAGTGC ATGGATTCTT AGCAATTATC TGGGTCGACC 8530       8540       8550       8560       8570       8580
      TGCGGAGCCT GTTCCTCTTC AGCTACCACC ACAGAGACTT ACTCTTGATT GCAGCGAGGA 8590       8600       8610       8620       8630       8640
      TTGTGGAACT TCTGGGACGC AGGGGGTGGG AAGTCCTCAA ATATTGGTGG AATCTCCTAC 8650       8660       8670       8680       8690       8700
      AGTATTGGAG TCAGGAACTA AAGAGTAGTG CTGTTAGCTT GCTTAATGCC ACAGCTATAG 8710       8720       8730       8740       8750       8760
      CAGTAGCTGA GGGGACAGAT AGGGTTATAG AAGTACTGCA AAGAGCTGGT AGAGCTATTC 8770       8780       8790       8800       8810       8820
      TCCACATACC TACAAGAATA AGACAGGGCT TGGAAAGGGC TTTGCTATAA GATGGGTGGC
```

Figure 2H

```
         8830       8840       8850       8860       8870       8880
    AAATGGTCAA AACGTGTGAC TGGATGGCCT ACTGTAAGGG AAAGAATGAG ACGAGCTGAA 8890       8900       8910       8920       8930       8940
    CCAGCTGAGC TAGCAGCAGA TGGGGTGGGA GCAGCATCCC GAGACCTGGA AAAACATGGA 8950       8960       8970       8980       8990       9000
    GCACTCACAA GTAGCAATAC AGCAGCTACC AATGCTGATT GTGCCTGGCT AGAAGCACAA 9010       9020       9030       9040       9050       9060
    GAGGAGGAGG AAGTGGGTTT TCCAGTCAAA CCTCAGGTAC CTTTAAGACC AATGACTTAC 9070       9080       9090       9100       9110       9120
    AAAGCAGCTT TAGATCTTAG CCACTTTTTA AAAGAAAAGG GGGGACTGGA TGGGTTAATT 9130       9140       9150       9160       9170       9180
    TACTCCCAAA AGAGACAAGA CATCCTTGAT CTGTGGGTCT ACCACACACA AGGCTACTTC 9190       9200       9210       9220       9230       9240
    CCTGATTGGC AGAACTACAC ACCAGGGCCA GGGATCAGAT ATCCACTGAC CTTTGGATGG 9250       9260       9270       9280       9290       9300
    TGCTTCAAGC TAGTACCAGT TGAGCCAGAG AAGATAGAAG AGGCCAATAA AGGAGAGAAC 9310       9320       9330       9340       9350       9360
    AACTGCTTGT TACACCCTAT GAGCCAGCAT GGATGGATGA CCCGGAGAGA GAAGTGTTAG 9370       9380       9390       9400       9410       9420
    TGTGGAAGTC TGACAGCCAC CTAGCATTTC AGCATTATGC CCGAGAGCTG CATCCGGAGT 9430       9440       9450       9460       9470       9480
    ACTACAAGAA CTGCTGACAT CGAGCTATCT ACAAGGGACT TTCCGCTGGG GACTTTCCAG 9490       9500       9510       9520       9530       9540
    GGAGGTGTGG CCTGGGCGGG ACCGGGGAGT GGCGAGCCCT CAGATCGTGC ATATAAGCAG 9550       9560       9570       9580       9590       9600
    CTGCTTTCTG CCTGTACTGG GTCTCTCTGG TTAGACCAGA TCTGAGCCTG GGAGCTCTCT 9610       9620       9630       9640       9650       9660
    GGCTAACTAG GGAACCCACT GCTTAAGCCT CAATAAAGCT TGCCTTGAGT GCTTCAAGTA 9670       9680       9690       9700       9710       9720
    GTGTGTGCCC GTCTGTTATG TGACTCTGGT AGCTAGAGAT CCCTCAGATC CTTTTAGGCA

9730
    GTGTGGAAAA TCTCTAGCA
```

```
         10        20        30        40        50        60
TGGATGGGTTAATTTACTCCCAAAGAGACAAGACATCCTTGATCTGTGGGTCTACCACAC
 W  M  G  *  F  T  P  K  E  T  R  H  P  *  S  V  G  L  P  H
  G  W  V  N  L  L  P  K  R  Q  D  I  L  D  L  W  V  Y  H  T
   D  G  L  I  Y  S  Q  R  D  K  T  S  L  I  C  G  S  T  T 70        80        90       100       110       120
ACAAGGCTACTTCCCTGATTGGCAGAACTACACACCAGGGCCAGGGATCAGATATCCACT
 T  R  L  L  P  *  L  A  E  L  H  T  R  A  R  D  Q  I  S  T
  Q  G  Y  F  P  D  W  Q  N  Y  T  P  G  P  G  I  R  Y  P  L
   H  K  A  T  S  L  I  G  R  T  T  H  Q  G  Q  G  S  D  I  H 130       140       150       160       170       180
GACCTTTGGATGGTGCTTCAAGCTAGTACCAGTTGAGCCAGAGAAGATAGAAGAGGCCAA
 D  L  W  M  V  L  Q  A  S  T  S  *  A  R  E  D  R  R  G  Q
  T  F  G  W  C  F  K  L  V  P  V  E  P  E  K  I  E  E  A  N
   *  P  L  D  G  A  S  S  *  Y  Q  L  S  Q  R  R  *  K  R  P 190       200       210       220       230       240
TAAAGGAGAGAACAACTGCTTGTTACACCCTATGAGCCAGCATGGGATGGATGACCCGGA
 *  R  R  E  Q  L  L  V  T  P  Y  E  P  A  W  D  G  *  P  G
   K  G  E  N  N  C  L  L  H  P  M  S  Q  H  G  M  D  D  P  E
  I  K  E  R  T  T  A  C  Y  T  L  *  A  S  M  G  W  M  T  R 250       260       270       280       290       300
GAGAGAAGTGTTAGTGTGGAAGTCTGACAGCCACCTAGCATTTCAGCATTATGCCCGAGA
 E  R  S  V  S  V  E  V  *  Q  P  P  S  I  S  A  L  C  P  R
   R  E  V  L  V  W  K  S  D  S  H  L  A  F  Q  H  Y  A  R  E
  R  E  K  C  *  C  G  S  L  T  A  T  *  H  F  S  I  M  P  E 310       320       330       340       350       360
GCTGCATCCGGAGTACTACAAGAACTGCTGACATCGAGCTATCTACAAGGGACTTTCCGC
 A  A  S  G  V  L  Q  E  L  L  T  S  S  Y  L  Q  G  T  F  R
   L  H  P  E  Y  Y  K  N  C  *  H  R  A  I  Y  K  G  L  S  A
  S  C  I  R  S  T  T  R  T  A  D  I  E  L  S  T  R  D  F  P 370       380       390       400       410       420
TGGGGACTTTCCAGGGAGGTGTGGCCTGGGCGGGACCGGGGAGTGGCGAGCCCTCAGATG
 W  G  L  S  R  E  V  W  P  G  R  D  R  G  V  A  S  P  Q  M
   G  D  F  P  G  R  C  G  L  G  G  T  G  E  W  R  A  L  R  C
  L  G  T  F  Q  G  G  V  A  W  A  G  P  G  S  G  E  P  S  D 430       440       450       460       470       480
CTGCATATAAGCAGCTGCTTTCTGCCTGTACTGGGTCTCTCTGGTTAGACCAGATCTGAG
 L  H  I  S  S  C  F  L  P  V  L  G  L  S  G  *  T  R  S  E
   C  I  *  A  A  A  F  C  L  Y  W  V  S  L  V  R  P  D  L  S
  A  A  Y  K  Q  L  L  S  A  C  T  G  S  L  W  L  D  Q  I  *

490       500       510       520       530       540
CCTGGGAGCTCTCTGGCTAACTAGGGAACCCACTGCTTAAGCCTCAATAAAGCTTGCCTT
 P  G  S  S  L  A  N  *  G  T  H  C  L  S  L  N  K  A  C  L
   L  G  A  L  W  L  T  R  E  P  T  A  *  A  S  I  K  L  A  L
  A  W  E  L  S  G  *  L  G  N  P  L  L  K  P  Q  *  S  L  P
```

Figure 6B

```
         550       560       570       580       590       600
GAGTGCTTCAAGTAGTGTGTGCCCGTCTGTTATGTGACTCTGGTAGCTAGAGATCCCTCA
  E  C  F  K  *  C  V  P  V  C  Y  V  T  L  V  A  R  D  P  S
    S  A  S  S  S  V  C  P  S  V  M  *  L  W  *  L  E  I  P  Q
  *  V  L  Q  V  V  C  A  R  L  L  C  D  S  G  S  *  R  S  L 610       620       630       640       650       660
GATCCTTTTAGGCAGTGTGGAAAATCTCTAGCAGTGGCGCCCGAACAGGGACTTGAAAGC
  D  P  F  R  Q  C  G  K  S  L  A  V  A  P  E  Q  G  L  E  S
    I  L  L  G  S  V  E  N  L  *  Q  W  R  P  N  R  D  L  K  A
  R  S  F  *  A  V  W  K  I  S  S  S  G  A  R  T  G  T  *  K 670       680       690       700       710       720
GAAAGAGAAACCAGAGGAGCTCTCTCGACGCAGGACTCGGCTTGCTGAAGCGCGCACGGC
  E  R  E  T  R  G  A  L  S  T  Q  D  S  A  C  *  S  A  H  G
    K  E  K  P  E  E  L  S  R  R  R  T  R  L  A  E  A  R  T  A
  R  K  R  N  Q  R  S  S  L  D  A  G  L  G  L  L  K  R  A  R 730       740       750       760       770       780
AAGAGGCGAGGGGCGGCGACTGGTGAGTACGCCAAAATTCTTGACTAGCGGAGGCTAGAA
  K  R  R  G  A  A  T  G  E  Y  A  K  I  L  D  *  R  R  L  E
    R  G  E  G  R  R  L  V  S  T  P  K  F  L  T  S  G  G  *  K
  Q  E  A  R  G  G  D  W  *  V  R  Q  N  S  *  L  A  E  A  R 790       800       810       820       830       840
GGAGAGAGATGGGTGCGAGAGCGTCGGTATTAAGCGGGGGAGAATTAGATCGATGGGAAA
  G  E  R  W  V  R  E  R  R  Y  *  A  G  E  N  *  I  D  G  K
    E  R  D  G  C  E  S  V  G  I  K  R  G  R  I  R  S  M  G  K
  R  R  E  M  G  A  R  A  S  V  L  S  G  G  E  L  D  R  W  E 850       860       870       880       890       900
AAATTCGGTTAAGGCCAGGGGGAAAGAAAAAATATAAATTAAAACATGTAGTATGGGCAA
  K  F  G  *  G  Q  G  E  R  K  N  I  N  *  N  M  *  Y  G  Q
    N  S  V  K  A  R  G  K  E  K  I  *  I  K  T  C  S  M  G  K
  K  I  R  L  R  P  G  G  K  K  K  Y  K  L  K  H  V  V  W  A 910       920       930       940       950       960
GCAGGGAGCTAGAACGATTCGCAGTCAATCCTGGCCTGTTAGAAACATCAGAAGGCTGTA
  A  G  S  *  N  D  S  Q  S  I  L  A  C  *  K  H  Q  K  A  V
    Q  G  A  R  T  I  R  S  Q  S  W  P  V  R  N  I  R  R  L  *
  S  R  E  L  E  R  F  A  V  N  P  G  L  L  E  T  S  E  G  C 970       980       990      1000      1010      1020
GACAAATACTGGGACAGCTACAACCATCCCTTCAGACAGGATCAGAAGAACTTAAATCAT
  D  K  Y  W  D  S  Y  N  H  P  F  R  Q  D  Q  K  N  L  N  H
    T  N  T  G  T  A  T  T  I  P  S  D  R  I  R  R  T  *  I  I
  R  Q  I  L  G  Q  L  Q  P  S  L  Q  T  G  S  E  E  L  K  S 1030      1040      1050      1060      1070      1080
TATATAATACAGTAGCAACCCTCTATTGTGTGCATCAAAAGATAGAGATAAAAGACACCA
  Y  I  I  Q  *  Q  P  S  I  V  C  I  K  R  *  R  *  K  T  P
    I  *  Y  S  S  N  P  L  L  C  A  S  K  D  R  D  K  R  H  Q
  L  Y  N  T  V  A  T  L  Y  C  V  H  Q  K  I  E  I  K  D  T
```

Figure 6C

```
         1090       1100       1110       1120       1130       1140
    AGGAAGCTTTAGAGAAAATAGAGGAAGAGCAAAACAAAAGTAAGAAAAAAGCACAGCAAG
      R  K  L  *  R  K  *  R  K  S  K  T  K  V  R  K  K  H  S  K
       G  S  F  R  E  N  R  G  R  A  K  Q  K  *  E  K  S  T  A  S
     K  E  A  L  E  K  I  E  E  E  Q  N  K  S  K  K  K  A  Q  Q 1150       1160       1170       1180       1190       1200
    CAGTAGCTGACACAGGAAACAGAGGAAACAGCAGCCAAGTCAGCCAAAATTACCCCATAG
     Q  *  L  T  Q  E  T  E  E  T  A  A  K  S  A  K  I  T  P  *
       S  S  *  H  R  K  Q  R  K  Q  Q  P  S  Q  P  K  L  P  H  S
     A  V  A  D  T  G  N  R  G  N  S  S  Q  V  S  Q  N  Y  P  I 1210       1220       1230       1240       1250       1260
    TGCAGAACATCCAGGGGCAAATGGTACATCAGGCCATATCACCTAGAACTTTAAATGCAT
      C  R  T  S  R  G  K  W  Y  I  R  P  Y  H  L  E  L  *  M  H
       A  E  H  P  G  A  N  G  T  S  G  H  I  T  *  N  F  K  C  M
     V  Q  N  I  Q  G  Q  M  V  H  Q  A  I  S  P  R  T  L  N  A 1270       1280       1290       1300       1310       1320
    GGGTAAAAGTAGTAGAAGAGAAGGCTTTCAGCCCAGAAGTAATACCCATGTTTTCAGCAT
      G  *  K  *  *  K  R  R  L  S  A  Q  K  *  Y  P  C  F  Q  H
       G  K  S  S  R  R  E  G  F  Q  P  R  S  N  T  H  V  F  S  I
     W  V  K  V  V  E  E  K  A  F  S  P  E  V  I  P  M  F  S  A 1330       1340       1350       1360       1370       1380
    TATCAGAAGGAGCCACCCCACAAGATTTAAACACCATGCTAAACACAGTGGGGGGACATC
      Y  Q  K  E  P  P  H  K  I  *  T  P  C  *  T  Q  W  G  D  I
       I  R  R  S  H  P  T  R  F  K  H  H  A  K  H  S  G  G  T  S
     L  S  E  G  A  T  P  Q  D  L  N  T  M  L  N  T  V  G  G  H 1390       1400       1410       1420       1430       1440
    AAGCAGCCATGCAAATGTTAAAAGAGACCATCAATGAGGAAGCTGCAGAATGGGATAGAT
      K  Q  P  C  K  C  *  K  R  P  S  M  R  K  L  Q  N  G  I  D
       S  S  H  A  N  V  K  R  D  H  Q  *  G  S  C  R  M  G  *  I
     Q  A  A  M  Q  M  L  K  E  T  I  N  E  E  A  A  E  W  D  R 1450       1460       1470       1480       1490       1500
    TGCATCCAGTGCATGCAGGGCCTATTGCACCAGGCCAGATGAGAGAACCAAGGGGAAGTG
      C  I  Q  C  M  Q  G  L  L  H  Q  A  R  *  E  N  Q  G  E  V
       A  S  S  A  C  R  A  Y  C  T  R  P  D  E  R  T  K  G  K  *
     L  H  P  V  H  A  G  P  I  A  P  G  Q  M  R  E  P  R  G  S 1510       1520       1530       1540       1550       1560
    ACATAGCAGGAACTACTAGTACCCTTCAGGAACAAATAGGATGGATGACAAATAATCCAC
      T  *  Q  E  L  L  V  P  F  R  N  K  *  D  G  *  Q  I  I  H
       H  S  R  N  Y  *  Y  P  S  G  T  N  R  M  D  D  K  *  S  T
     D  I  A  G  T  T  S  T  L  Q  E  Q  I  G  W  M  T  N  N  P 1570       1580       1590       1600       1610       1620
    CTATCCCAGTAGGAGAAATCTATAAAAGATGGATAATCCTGGGATTAAATAAAATAGTAA
      L  S  Q  *  E  K  S  I  K  D  G  *  S  W  D  *  I  K  *  *
       Y  P  S  R  R  N  L  *  K  M  D  N  P  G  I  K  *  N  S  K
     P  I  P  V  G  E  I  Y  K  R  W  I  I  L  G  L  N  K  I  V
```

Figure 6D

```
        1630       1640       1650       1660       1670       1680
GGATGTATAGCCCTTCCAGCATTCTGGACATAAGACAAGGACCAAAGGAACCCTTTAGAG
  G  C  I  A  L  P  A  F  W  T  *  D  K  D  Q  R  N  P  L  E
   D  V  *  P  F  Q  H  S  G  H  K  T  R  T  K  G  T  L  *  R
 R  M  Y  S  P  S  S  I  L  D  I  R  Q  G  P  K  E  P  F  R 1690       1700       1710       1720       1730       1740
ACTATGTAGACCGGTTCTATAAAACTCTAAGAGCCGAGCAAGCTTCACAGGAGGTAAAAA
  T  M  *  T  G  S  I  K  L  *  E  P  S  K  L  H  R  R  *  K
   L  C  R  P  V  L  *  N  S  K  S  R  A  S  F  T  G  G  K  K
 D  Y  V  D  R  F  Y  K  T  L  R  A  E  Q  A  S  Q  E  V  K 1750       1760       1770       1780       1790       1800
ATTGGATGACAGAAACCTTGTTGGTCCAAAATGCGAACCCAGATTGTAAGACTATTTTAA
  I  G  *  Q  K  P  C  W  S  K  M  R  T  Q  I  V  R  L  F  *
   L  D  D  R  N  L  V  G  P  K  C  E  P  R  L  *  D  Y  F  K
 N  W  M  T  E  T  L  L  V  Q  N  A  N  P  D  C  K  T  I  L 1810       1820       1830       1840       1850       1860
AAGCATTGGGACCAGCAGCTACACTAGAAGAAATGATGACAGCATGTCAGGGAGTGGGAG
  K  H  W  D  Q  Q  L  H  *  K  K  *  *  Q  H  V  R  E  W  E
   S  I  G  T  S  S  Y  T  R  R  N  D  D  S  M  S  G  S  G  R
 K  A  L  G  P  A  A  T  L  E  E  M  M  T  A  C  Q  G  V  G 1870       1880       1890       1900       1910       1920
GACCTGGTCATAAAGCAAGAGTTTTGGCGGAAGCGATGAGCCAAGTAACAAATTCAGCTA
  D  L  V  I  K  Q  E  F  W  R  K  R  *  A  K  *  Q  I  Q  L
   T  W  S  *  S  K  S  F  G  G  S  D  E  P  S  N  K  F  S  Y
 G  P  G  H  K  A  R  V  L  A  E  A  M  S  Q  V  T  N  S  A 1930       1940       1950       1960       1970       1980
CCATAATGATGCAGAGAGGCAATTTTAGGAATCAAAGAAAGATTATCAAGTGCTTCAATT
  P  *  *  C  R  E  A  I  L  G  I  K  E  R  L  S  S  A  S  I
   H  N  D  A  E  R  Q  F  *  E  S  K  K  D  Y  Q  V  L  Q  L
 T  I  M  M  Q  R  G  N  F  R  N  Q  R  K  I  I  K  C  F  N 1990       2000       2010       2020       2030       2040
GTGGCAAAGAAGGGCACATAGCCAAAAATTGCAGGGCCCCTAGGAAAAGGGGCTGTTGGA
  V  A  K  K  G  T  *  P  K  I  A  G  P  L  G  K  G  A  V  G
   W  Q  R  R  A  H  S  Q  K  L  Q  G  P  *  E  K  G  L  L  E
 C  G  K  E  G  H  I  A  K  N  C  R  A  P  R  K  R  G  C  W 2050       2060       2070       2080       2090       2100
AATGTGGAAAGGAAGGACACCAAATGAAAGATTGTACTGAGAGACAGGCTAATTTTTTAG
  N  V  E  R  K  D  T  K  *  K  I  V  L  R  D  R  L  I  F  *
   M  W  K  G  R  T  P  N  E  R  L  Y  *  E  T  G  *  F  F  R
 K  C  G  K  E  G  H  Q  M  K  D  C  T  E  R  Q  A  N  F  L 2110       2120       2130       2140       2150       2160
GGAAGATCTGGCCTTCCTGCAAGGGAAGGCAGGGAATTTTCCTCAGAGCAGAACAGAGCC
  G  R  S  G  L  P  A  R  E  G  R  E  F  S  S  E  Q  N  R  A
   E  D  L  A  F  L  Q  G  K  A  G  N  F  P  Q  S  R  T  E  P
 G  K  I  W  P  S  C  K  G  R  Q  G  I  F  L  R  A  E  Q  S
```

Figure 6E

```
          2170       2180       2190       2200       2210       2220
    AACAGCCCCACCAGAAGAGAGCTTCAGGTTTGGGGAAGAGACAACAACTCCCTATCAGAA
      N  S  P  T  R  R  E  L  Q  V  W  G  R  D  N  N  S  L  S  E
       T  A  P  P  E  E  S  F  R  F  G  E  E  T  T  T  P  Y  Q  K
    Q  Q  P  H  Q  K  R  A  S  G  L  G  K  R  Q  Q  L  P  I  R 2230       2240       2250       2260       2270       2280
    GCAGGAGAAGAAGCAGGAGACGATAGACAAGGACCTGTATCCTTTAGCTTCCCTCAAATC
      A  G  E  E  A  G  D  D  R  Q  G  P  V  S  F  S  F  P  Q  I
       Q  E  K  K  Q  E  T  I  D  K  D  L  Y  P  L  A  S  L  K  S
    S  R  R  R  S  R  R  R  *  T  R  T  C  I  L  *  L  P  S  N 2290       2300       2310       2320       2330       2340
    ACTCTTTGGCAACGACCCATTGTCACAATAAAGATAGGGGGCAACTAAAGGAAGCTCTA
      T  L  W  Q  R  P  I  V  T  I  K  I  G  G  Q  L  K  E  A  L
       L  F  G  N  D  P  L  S  Q  *  R  *  G  G  N  *  R  K  L  Y
    H  S  L  A  T  T  H  C  H  N  K  D  R  G  A  T  K  G  S  S 2350       2360       2370       2380       2390       2400
    TTAGATACAGGAGCAGATGATACAGTATTAGAAGAAATGAATTTGCCAGGAAGATGGAAA
      L  D  T  G  A  D  D  T  V  L  E  E  M  N  L  P  G  R  W  K
       *  I  Q  E  Q  M  I  Q  Y  *  K  K  *  I  C  Q  E  D  G  N
    I  R  Y  R  S  R  *  Y  S  I  R  R  N  E  F  A  R  K  M  E 2410       2420       2430       2440       2450       2460
    CCAAAAATGATAGGGGGAATTGGAGGTTTTATCAAAGTAAGACAGTATGATCAGATAACC
      P  K  M  I  G  G  I  G  G  F  I  K  V  R  Q  Y  D  Q  I  T
       Q  K  *  *  G  E  L  E  V  L  S  K  *  D  S  M  I  R  *  P
    T  K  N  D  R  G  N  W  R  F  Y  Q  S  K  T  V  *  S  D  N 2470       2480       2490       2500       2510       2520
    ATAGAAATCTGTGGACATAAAGCTATAGGTACAGTATTAGTAGGACCTACACCTGTCAAC
      I  E  I  C  G  H  K  A  I  G  T  V  L  V  G  P  T  P  V  N
       *  K  S  V  D  I  K  L  *  V  Q  Y  *  *  D  L  H  L  S  T
    H  R  N  L  W  T  *  S  Y  R  Y  S  I  S  R  T  Y  T  C  Q 2530       2540       2550       2560       2570       2580
    ATAATTGGAAGAAATCTGTTGACTCAGCTTGGGTGCACTTTAAATTTTCCCATTAGTCCT
      I  I  G  R  N  L  L  T  Q  L  G  C  T  L  N  F  P  I  S  P
       *  L  E  E  I  C  *  L  S  L  G  A  L  *  I  F  P  L  V  L
    H  N  W  K  K  S  V  D  S  A  W  V  H  F  K  F  S  H  *  S 2590       2600       2610       2620       2630       2640
    ATTGAAACTGTACCAGTAAAATTAAAGCCAGGAATGGATGGCCCAAAAGTTAAACAATGG
      I  E  T  V  P  V  K  L  K  P  G  M  D  G  P  K  V  K  Q  W
       L  K  L  Y  Q  *  N  *  S  Q  E  W  M  A  Q  K  L  N  N  G
    Y  *  N  C  T  S  K  I  K  A  R  N  G  W  P  K  S  *  T  M 2650       2660       2670       2680       2690       2700
    CCATTGACAGAAGAAAAAATAAAAGCATTAATAGAAATTTGTACAGAAATGGAAAAGGAA
      P  L  T  E  E  K  I  K  A  L  I  E  I  C  T  E  M  E  K  E
       H  *  Q  K  K  K  *  K  H  *  *  K  F  V  Q  K  W  K  R  K
    A  I  D  R  R  K  N  K  S  I  N  R  N  L  Y  R  N  G  K  G
```

Figure 6F

```
          2710       2720       2730       2740       2750       2760
     GGGAAAATTTCAAAAATTGGGCCTGAAAATCCATACAATACTCCAGTATTTGCCATAAAG
      G  K  I  S  K  I  G  P  E  N  P  Y  N  T  P  V  F  A  I  K
        G  K  F  Q  K  L  G  L  K  I  H  T  I  L  Q  Y  L  P  *  R
     R  E  N  F  K  N  W  A  *  K  S  I  Q  Y  S  S  I  C  H  K 2770       2780       2790       2800       2810       2820
     AAAAAAGACAGTACTAAATGGAGAAAATTAGTAGATTTCAGAGAACTTAATAAGAAAACT
       K  K  D  S  T  K  W  R  K  L  V  D  F  R  E  L  N  K  K  T
         K  K  T  V  L  N  G  E  N  *  *  I  S  E  N  L  I  R  K  L
     E  K  R  Q  Y  *  M  E  K  I  S  R  F  Q  R  T  *  *  E  N 2830       2840       2850       2860       2870       2880
     CAAGACTTCTGGGAAGTTCAATTAGGAATACCACATCCTGCAGGGTTAAAAAAGAAAAAA
      Q  D  F  W  E  V  Q  L  G  I  P  H  P  A  G  L  K  K  K  K
        K  T  S  G  K  F  N  *  E  Y  H  I  L  Q  G  *  K  R  K  N
     S  R  L  L  G  S  S  I  R  N  T  T  S  C  R  V  K  K  E  K 2890       2900       2910       2920       2930       2940
     TCAGTAACAGTACTGGATGTGGGTGATGCATATTTTTCAGTTCCCTTAGATAAAGACTTC
      S  V  T  V  L  D  V  G  D  A  Y  F  S  V  P  L  D  K  D  F
        Q  *  Q  Y  W  M  W  V  M  H  I  F  Q  F  P  *  I  K  T  S
     I  S  N  S  T  G  C  G  *  C  I  F  F  S  S  L  R  *  R  L 2950       2960       2970       2980       2990       3000
     AGGAAGTATACTGCATTTACCATACCTAGTATAAACAATGAAACACCAGGGATTAGATAT
      R  K  Y  T  A  F  T  I  P  S  I  N  N  E  T  P  G  I  R  Y
        G  S  I  L  H  L  P  Y  L  V  *  T  M  K  H  Q  G  L  D  I
     Q  E  V  Y  C  I  Y  H  T  *  Y  K  Q  *  N  T  R  D  *  I 3010       3020       3030       3040       3050       3060
     CAGTACAATGTGCTTCCACAGGGATGGAAAGGATCACCAGCAATATTCCAAAGTAGCATG
      Q  Y  N  V  L  P  Q  G  W  K  G  S  P  A  I  F  Q  S  S  M
        S  T  M  C  F  H  R  D  G  K  D  H  Q  Q  Y  S  K  V  A  *
     S  V  Q  C  A  S  T  G  M  E  R  I  T  S  N  I  P  K  *  H 3070       3080       3090       3100       3110       3120
     ACAAAAATCTTAGAGCCTTTTAGAAAACAAAATCCAGACATAGTTATCTATCAATACATG
      T  K  I  L  E  P  F  R  K  Q  N  P  D  I  V  I  Y  Q  Y  M
        Q  K  S  *  S  L  L  E  N  K  I  Q  T  *  L  S  I  N  T  W
     D  K  N  L  R  A  F  *  K  T  K  S  R  H  S  Y  L  S  I  H 3130       3140       3150       3160       3170       3180
     GATGATTTGTATGTAGGATCTGACTTAGAAATAGGGCAGCATAGAGCAAAAATAGAGGAA
      D  D  L  Y  V  G  S  D  L  E  I  G  Q  H  R  A  K  I  E  E
        M  I  C  M  *  D  L  T  *  K  *  G  S  I  E  Q  K  *  R  N
     G  *  F  V  C  R  I  *  L  R  N  R  A  A  *  S  K  N  R  G 3190       3200       3210       3220       3230       3240
     CTGAGACGACATCTGTTGAGGTGGGGATTTACCACACCAGACAAAAAACATCAGAAAGAA
      L  R  R  H  L  L  R  W  G  F  T  T  P  D  K  K  H  Q  K  E
        *  D  D  I  C  *  G  G  D  L  P  H  Q  T  K  N  I  R  K  N
     T  E  T  T  S  V  E  V  G  I  Y  H  T  R  Q  K  T  S  E  R
```

Figure 6G

```
          3250      3260      3270      3280      3290      3300
     CCTCCATTCCTTTGGATGGGTTATGAACTCCATCCTGATAAATGGACAGTACAGCCTATA
      P  P  F  L  W  M  G  Y  E  L  H  P  D  K  W  T  V  Q  P  I
       L  H  S  F  G  W  V  M  N  S  I  L  I  N  G  Q  Y  S  L  *
     T  S  I  P  L  D  G  L  *  T  P  S  *  *  M  D  S  T  A  Y 3310      3320      3330      3340      3350      3360
     GTGCTGCCAGAAAAAGACAGCTGGACTGTCAATGACATACAGAAGTTAGTGGGAAAATTG
      V  L  P  E  K  D  S  W  T  V  N  D  I  Q  K  L  V  G  K  L
       C  C  Q  K  K  T  A  G  L  S  M  T  Y  R  S  *  W  E  N  *
     S  A  A  R  K  R  Q  L  D  C  Q  *  H  T  E  V  S  G  K  I 3370      3380      3390      3400      3410      3420
     AATTGGGCAAGTCAAATTTACGCAGGGATTAAAGTAAAGCAATTATGTAAACTCCTTAGA
      N  W  A  S  Q  I  Y  A  G  I  K  V  K  Q  L  C  K  L  L  R
       I  G  Q  V  K  F  T  Q  G  L  K  *  S  N  Y  V  N  S  L  E
     E  L  G  K  S  N  L  R  R  D  *  S  K  A  I  M  *  T  P  *

3430      3440      3450      3460      3470      3480
     GGAACCAAAGCACTAACAGAAGTAATACCACTAACAGAAGAAGCAGAGCTAGAACTGGCA
      G  T  K  A  L  T  E  V  I  P  L  T  E  E  A  E  L  E  L  A
       E  P  K  H  *  Q  K  *  Y  H  *  Q  K  K  Q  S  *  N  W  Q
     R  N  Q  S  T  N  R  S  N  T  T  N  R  R  S  R  A  R  T  G 3490      3500      3510      3520      3530      3540
     GAAAACAGGGAAATTCTAAAAGAACCAGTACATGGAGTGTATTATGACCCATCAAAAGAC
      E  N  R  E  I  L  K  E  P  V  H  G  V  Y  Y  D  P  S  K  D
       K  T  G  K  F  *  K  N  Q  Y  M  E  C  I  M  T  H  Q  K  T
     R  K  Q  G  N  S  K  R  T  S  T  W  S  V  L  *  P  I  K  R 3550      3560      3570      3580      3590      3600
     TTAATAGCAGAAGTACAGAAGCAGGGGCAAGGCCAATGGACATATCAAATTTATCAAGAG
      L  I  A  E  V  Q  K  Q  G  Q  G  Q  W  T  Y  Q  I  Y  Q  E
       *  *  Q  K  Y  R  S  R  G  K  A  N  G  H  I  K  F  I  K  S
     L  N  S  R  S  T  E  A  G  A  R  P  M  D  I  S  N  L  S  R 3610      3620      3630      3640      3650      3660
     CCATTTAAAAATCTGAAAACAGGCAAATATGCAAGAATGAGGGGTGCCCACACTAATGAT
      P  F  K  N  L  K  T  G  K  Y  A  R  M  R  G  A  H  T  N  D
       H  L  K  I  *  K  Q  A  N  M  Q  E  *  G  V  P  T  L  M  M
     A  I  *  K  S  E  N  R  Q  I  C  K  N  E  G  C  P  H  *  *

3670      3680      3690      3700      3710      3720
     GTAAAACAATTAACAGAGGCAGTGCAAAAAATAGCCACAGAAAGCATAGTAATATGGGGA
      V  K  Q  L  T  E  A  V  Q  K  I  A  T  E  S  I  V  I  W  G
       *  N  N  *  Q  R  Q  C  K  K  *  P  Q  K  A  *  *  Y  G  E
     C  K  T  I  N  R  G  S  A  K  N  S  H  R  K  H  S  N  M  G 3730      3740      3750      3760      3770      3780
     AAGACTCCTAAATTTAGACTACCCATACAAAAAGAAACATGGGAAACATGGTGGACAGAG
      K  T  P  K  F  R  L  P  I  Q  K  E  T  W  E  T  W  W  T  E
       R  L  L  N  L  D  Y  P  Y  K  K  K  H  G  K  H  G  G  Q  S
     K  D  S  *  I  *  T  T  H  T  K  R  N  M  G  N  M  V  D  R
```

Figure 6H

```
        3790      3800      3810      3820      3830      3840
TATTGGCAAGCCACCTGGATTCCTGAGTGGGAGTTTGTCAATACCCCTCCCTTAGTGAAA
  Y  W  Q  A  T  W  I  P  E  W  E  F  V  N  T  P  P  L  V  K
   I  G  K  P  P  G  F  L  S  G  S  L  S  I  P  L  P  *  *  N
 V  L  A  S  H  L  D  S  *  V  G  V  C  Q  Y  P  S  L  S  E 3850      3860      3870      3880      3890      3900
TTATGGTACCAGTTAGAGAAAGAACCCATAGTAGGAGCAGAAACTTTCTATGTAGATGGG
  L  W  Y  Q  L  E  K  E  P  I  V  G  A  E  T  F  Y  V  D  G
   Y  G  T  S  *  R  K  N  P  *  *  E  Q  K  L  S  M  *  M  G
 I  M  V  P  V  R  E  R  T  H  S  R  S  R  N  F  L  C  R  W 3910      3920      3930      3940      3950      3960
GCAGCTAACAGGGAGACTAAAAAAGGAAAAGCAGGATATGTTACTAACAGAGGAAGACAA
  A  A  N  R  E  T  K  K  G  K  A  G  Y  V  T  N  R  G  R  Q
   Q  L  T  G  R  L  K  K  E  K  Q  D  M  L  L  T  E  E  D  K
 G  S  *  Q  G  D  *  K  R  K  S  R  I  C  Y  *  Q  R  K  T 3970      3980      3990      4000      4010      4020
AAGGTTGTCTCCCTAACTGACACAACAAATCAGAAGACTGAGTTACAAGCAATTCATCTA
  K  V  V  S  L  T  D  T  T  N  Q  K  T  E  L  Q  A  I  H  L
   R  L  S  P  *  L  T  Q  Q  I  R  R  L  S  Y  K  Q  F  I  *
 K  G  C  L  P  N  *  H  N  K  S  E  D  *  V  T  S  N  S  S 4030      4040      4050      4060      4070      4080
GCTTTGCAAGATTCAGGGTTAGAAGTAAACATAGTAACAGACTCACAATATGCATTAGGA
  A  L  Q  D  S  G  L  E  V  N  I  V  T  D  S  Q  Y  A  L  G
   L  C  K  I  Q  G  *  K  *  T  *  *  Q  T  H  N  M  H  *  E
 S  F  A  R  F  R  V  R  S  K  H  S  N  R  L  T  I  C  I  R 4090      4100      4110      4120      4130      4140
ATCATTCAAGCACAACCAGATAAAAGTGAATCAGAGTTAGTCAGTCAAATAATAGAGCAG
  I  I  Q  A  Q  P  D  K  S  E  S  E  L  V  S  Q  I  I  E  Q
   S  F  K  H  N  Q  I  K  V  N  Q  S  *  S  V  K  *  *  S  S
 N  H  S  S  T  T  R  *  K  *  I  R  V  S  Q  S  N  N  R  A 4150      4160      4170      4180      4190      4200
TTAATAAAAAAGGAAAAGGTCTATCTGGCATGGGTACCAGCACACAAAGGAATTGGAGGA
  L  I  K  K  E  K  V  Y  L  A  W  V  P  A  H  K  G  I  G  G
   *  *  K  R  K  R  S  I  W  H  G  Y  Q  H  T  K  E  L  E  E
 V  N  K  K  G  K  G  L  S  G  M  G  T  S  T  Q  R  N  W  R 4210      4220      4230      4240      4250      4260
AATGAACAAGTAGATAAATTAGTCAGTGCTGGAATCAGGAAAGTACTATTTTTAGATGGA
  N  E  Q  V  D  K  L  V  S  A  G  I  R  K  V  L  F  L  D  G
   M  N  K  *  I  N  *  S  V  L  E  S  G  K  Y  Y  F  *  M  E
 K  *  T  S  R  *  I  S  Q  C  W  N  Q  E  S  T  I  F  R  W 4270      4280      4290      4300      4310      4320
ATAGATAAGGCCCAAGAAGACCATGAGAAATATCACAGTAATTGGAGAGCAATGGCTAGT
  I  D  K  A  Q  E  D  H  E  K  Y  H  S  N  W  R  A  M  A  S
   *  I  R  P  K  K  T  M  R  N  I  T  V  I  G  E  Q  W  L  V
 N  R  *  G  P  R  R  P  *  E  I  S  Q  *  L  E  S  N  G  *
```

Figure 6I

```
          4330      4340      4350      4360      4370      4380
GACTTTAACCTACCACCTATAGTAGCAAAAGAAATAGTAGCCAGCTGTGATAAATGTCAG
  D  F  N  L  P  P  I  V  A  K  E  I  V  A  S  C  D  K  C  Q
   T  L  T  Y  H  L  *  *  Q  K  K  *  *  P  A  V  I  N  V  S
 *  L  *  P  T  T  Y  S  S  K  R  N  S  S  Q  L  *  *  M  S 4390      4400      4410      4420      4430      4440
CTAAAAGGAGAAGCCATGCATGGACAAGTAGACTGTAGTCCAGGAATATGGCAACTAGAT
  L  K  G  E  A  M  H  G  Q  V  D  C  S  P  G  I  W  Q  L  D
   *  K  E  K  P  C  M  D  K  *  T  V  V  Q  E  Y  G  N  *  I
 A  K  R  R  S  H  A  W  T  S  R  L  *  S  R  N  M  A  T  R 4450      4460      4470      4480      4490      4500
TGTACACATTTAGAAGGAAAAGTTATCCTGGTAGCAGTTCATGTAGCCAGTGGATACATA
  C  T  H  L  E  G  K  V  I  L  V  A  V  H  V  A  S  G  Y  I
   V  H  I  *  K  E  K  L  S  W  *  Q  F  M  *  P  V  D  T  *
 L  Y  T  F  R  R  K  S  Y  P  G  S  S  S  C  S  Q  W  I  H 4510      4520      4530      4540      4550      4560
GAAGCAGAAGTTATTCCAGCAGAGACAGGGCAGGAGACAGCATACTTTCTCTTAAAATTA
  E  A  E  V  I  P  A  E  T  G  Q  E  T  A  Y  F  L  L  K  L
   K  Q  K  L  F  Q  Q  R  Q  G  R  R  Q  H  T  F  S  *  N  *
 R  S  R  S  Y  S  S  R  D  R  A  G  D  S  I  L  S  L  K  I 4570      4580      4590      4600      4610      4620
GCAGGAAGATGGCCAGTAAAAACAATACATACAGACAATGGCCCCAATTTCACCAGTACT
  A  G  R  W  P  V  K  T  I  H  T  D  N  G  P  N  F  T  S  T
   Q  E  D  G  Q  *  K  Q  Y  I  Q  T  M  A  P  I  S  P  V  L
 S  R  K  M  A  S  K  N  N  T  Y  R  Q  W  P  Q  F  H  Q  Y 4630      4640      4650      4660      4670      4680
ACGGTTAAGGCCGCCTGTTGGTGGGCGGGGATCAAGCAGGAATTTGGCATTCCCTACAAT
  T  V  K  A  A  C  W  W  A  G  I  K  Q  E  F  G  I  P  Y  N
   R  L  R  P  P  V  G  G  R  G  S  S  R  N  L  A  F  P  T  I
 Y  G  *  G  R  L  L  V  G  G  D  Q  A  G  I  W  H  S  L  Q 4690      4700      4710      4720      4730      4740
CCCCAAAGTCAAGGAGTAATAGAATCTATGAATAAAGAATTAAAGAAAATTATAGGACAG
  P  Q  S  Q  G  V  I  E  S  M  N  K  E  L  K  K  I  I  G  Q
   P  K  V  K  E  *  *  N  L  *  I  K  N  *  R  K  L  *  D  R
 S  P  K  S  R  S  N  R  I  Y  E  *  R  I  K  E  N  Y  R  T 4750      4760      4770      4780      4790      4800
GTAAGAGATCAGGCTGAACATCTTAAGACAGCAGTACAAATGGCAGTATTCATCCACAAT
  V  R  D  Q  A  E  H  L  K  T  A  V  Q  M  A  V  F  I  H  N
   *  E  I  R  L  N  I  L  R  Q  Q  Y  K  W  Q  Y  S  S  T  I
 G  K  R  S  G  *  T  S  *  D  S  S  T  N  G  S  I  H  P  Q 4810      4820      4830      4840      4850      4860
TTTAAAAGAAAAGGGGGGATTGGGGGGTACAGTGCAGGGGAAAGAATAGTAGACATAATA
  F  K  R  K  G  G  I  G  G  Y  S  A  G  E  R  I  V  D  I  I
   L  K  E  K  G  G  L  G  G  T  V  Q  G  K  E  *  *  T  *  *
 F  *  K  K  R  G  D  W  G  V  Q  C  R  G  K  N  S  R  H  N
```

Figure 6J

```
         4870      4880      4890      4900      4910      4920
       GCAACAGACATACAAACTAAAGAACTACAAAAACAAATTACAAAAAATTCAAAATTTTCGG
        A  T  D  I  Q  T  K  E  L  Q  K  Q  I  T  K  I  Q  N  F  R
         Q  Q  T  Y  K  L  K  N  Y  K  N  K  L  Q  K  F  K  I  F  G
        S  N  R  H  T  N  *  R  T  T  K  T  N  Y  K  N  S  K  F  S 4930      4940      4950      4960      4970      4980
       GTTTATTACAGGGACAGCAGAGATCCACTTTGGAAAGGACCAGCAAAGCTTCTCTGGAAA
        V  Y  Y  R  D  S  R  D  P  L  W  K  G  P  A  K  L  L  W  K
         F  I  T  G  T  A  E  I  H  F  G  K  D  Q  Q  S  F  S  G  K
        G  L  L  Q  G  Q  Q  R  S  T  L  E  R  T  S  K  A  S  L  E 4990      5000      5010      5020      5030      5040
       GGTGAAGGGGCAGTAGTAATACAAGATAATAGTGACATAAAAGTAGTGCCAAGAAGAAAA
        G  E  G  A  V  V  I  Q  D  N  S  D  I  K  V  V  P  R  R  K
         V  K  G  Q  *  *  Y  K  I  I  V  T  *  K  *  C  Q  E  E  K
        R  *  R  G  S  S  N  T  R  *  *  *  H  K  S  S  A  K  K  K 5050      5060      5070      5080      5090      5100
       GCAAAGATCATTAGGGATTATGGAAAACAGATGGCAGGTGATGATTGTGTGGCAAGTAGA
        A  K  I  I  R  D  Y  G  K  Q  M  A  G  D  D  C  V  A  S  R
         Q  R  S  L  G  I  M  E  N  R  W  Q  V  M  I  V  W  Q  V  D
        S  K  D  H  *  G  L  W  K  T  D  G  R  *  *  L  C  G  K  *

5110      5120      5130      5140      5150      5160
       CAGGATGAGGATTAGAACATGGAAAAGTTTAGTAAAACACCATATGTATATTTCAAAGAA
        Q  D  E  D  *  N  M  E  K  F  S  K  T  P  Y  V  Y  F  K  E
         R  M  R  I  R  T  W  K  S  L  V  K  H  H  M  Y  I  S  K  K
        T  G  *  G  L  E  H  G  K  V  *  *  N  T  I  C  I  F  Q  R 5170      5180      5190      5200      5210      5220
       AGCTAAAGGATGGTTTTATAGACATCACTATGAAAGCACTCATCCAAGAATAAGTTCAGA
        S  *  R  M  V  L  *  T  S  L  *  K  H  S  S  K  N  K  F  R
         A  K  G  W  F  Y  R  H  H  Y  E  S  T  H  P  R  I  S  S  E
        K  L  K  D  G  F  I  D  I  T  M  K  A  L  I  Q  E  *  V  Q 5230      5240      5250      5260      5270      5280
       AGTACACATCCCACTAGGGGATGCTAGATTGGTAATAACAACATATTGGGGTCTGCATAC
        S  T  H  P  T  R  G  C  *  I  G  N  N  N  I  L  G  S  A  Y
         V  H  I  P  L  G  D  A  R  L  V  I  T  T  Y  W  G  L  H  T
        K  Y  T  S  H  *  G  M  L  D  W  *  *  Q  H  I  G  V  C  I 5290      5300      5310      5320      5330      5340
       AGGAGAAAGAGACTGGCATTTAGGTCAGGGAGTCTCCATAGAATGGAGGAAAAAGAGATA
        R  R  K  R  L  A  F  R  S  G  S  L  H  R  M  E  E  K  E  I
         G  E  R  D  W  H  L  G  Q  G  V  S  I  E  W  R  K  K  R  Y
        Q  E  K  E  T  G  I  *  V  R  E  S  P  *  N  G  G  K  R  D 5350      5360      5370      5380      5390      5400
       TAGCACACAAGTAGACCCTGACCTAGCAGACCACCTAATTCATCTGCATTACTTTGATTG
        *  H  T  S  R  P  *  P  S  R  P  P  N  S  S  A  L  L  *  L
         S  T  Q  V  D  P  D  L  A  D  H  L  I  H  L  H  Y  F  D  C
        I  A  H  K  *  T  L  T  *  Q  T  T  *  F  I  C  I  T  L  I
```

Figure 6K

```
        5410      5420      5430      5440      5450      5460
TTTTTCAGACTCTGCCATAAGAAAGGCCATATTAGGACATAGAGTTAGTCCTATTTGTGA
  F  F  R  L  C  H  K  K  G  H  I  R  T  *  S  *  S  Y  L  *
   F  S  D  S  A  I  R  K  A  I  L  G  H  R  V  S  P  I  C  E
 V  F  Q  T  L  P  *  E  R  P  Y  *  D  I  E  L  V  L  F  V 5470      5480      5490      5500      5510      5520
ATTTCAAGCAGGACATAACAAGGTAGGATCTCTACAGTACTTGGCACTAACAGCATTAAT
  I  S  S  R  T  *  Q  G  R  I  S  T  V  L  G  T  N  S  I  N
   F  Q  A  G  H  N  K  V  G  S  L  Q  Y  L  A  L  T  A  L  I
 N  F  K  Q  D  I  T  R  *  D  L  Y  S  T  W  H  *  Q  H  *

5530      5540      5550      5560      5570      5580
AACACCAAAAAAGATAAAGCCACCTTTGCCTAGTGTTAAGAAACTGACAGAGGATAGATG
  N  T  K  K  D  K  A  T  F  A  *  C  *  E  T  D  R  G  *  M
   T  P  K  K  I  K  P  P  L  P  S  V  K  K  L  T  E  D  R  W
 *  H  Q  K  R  *  S  H  L  C  L  V  L  R  N  *  Q  R  I  D 5590      5600      5610      5620      5630      5640
GAACAAGCCCCAGAAGACCAAGGGCCACAGAGGGAGCCATACAATCAATGGGCATTAGAG
  E  Q  A  P  E  D  Q  G  P  Q  R  E  P  Y  N  Q  W  A  L  E
   N  K  P  Q  K  T  K  G  H  R  G  S  H  T  I  N  G  H  *  S
 G  T  S  P  R  R  P  R  A  T  E  G  A  I  Q  S  M  G  I  R 5650      5660      5670      5680      5690      5700
CTTTTAGAGGAGCTTAAGAATGAAGCTGTTAGACATTTTCCTAGGATATGGCTCCATGGC
  L  L  E  E  L  K  N  E  A  V  R  H  F  P  R  I  W  L  H  G
   F  *  R  S  L  R  M  K  L  L  D  I  F  L  G  Y  G  S  M  A
 A  F  R  G  A  *  E  *  S  C  *  T  F  S  *  D  M  A  P  W 5710      5720      5730      5740      5750      5760
TTAGGGCAACATATCTATGAAACTTATGGGGATACTTGGGCAGGAGTGGAAGCCATAATA
  L  G  Q  H  I  Y  E  T  Y  G  D  T  W  A  G  V  E  A  I  I
   *  G  N  I  S  M  K  L  M  G  I  L  G  Q  E  W  K  P  *  *
 L  R  A  T  Y  L  *  N  L  W  G  Y  L  G  R  S  G  S  H  N 5770      5780      5790      5800      5810      5820
AGAATTCTACAACAACTGCTGTTTATTCATTTCAGAATTGGGTGTCGACATAGCAGAATA
  R  I  L  Q  Q  L  L  F  I  H  F  R  I  G  C  R  H  S  R  I
   E  F  Y  N  N  C  C  L  F  I  S  E  L  G  V  D  I  A  E  *
 K  N  S  T  T  T  A  V  Y  S  F  Q  N  W  V  S  T  *  Q  N 5830      5840      5850      5860      5870      5880
GGCATTATTCGACAGAGGAGAGCAAGAAATGGAGCCAGTAGATCCTAGACTAGAGCCCTG
  G  I  I  R  Q  R  R  A  R  N  G  A  S  R  S  *  T  R  A  L
   A  L  F  D  R  G  E  Q  E  M  E  P  V  D  P  R  L  E  P  W
 R  H  Y  S  T  E  E  S  K  K  W  S  Q  *  I  L  D  *  S  P 5890      5900      5910      5920      5930      5940
GAAGCATCCAGGAAGTCAGCCTAAGACTGCTTGTACCACTTGCTATTGTAAAAAGTGTTG
  E  A  S  R  K  S  A  *  D  C  L  Y  H  L  L  L  *  K  V  L
   K  H  P  G  S  Q  P  K  T  A  C  T  T  C  Y  C  K  K  C  C
 G  S  I  Q  E  V  S  L  R  L  L  V  P  L  A  I  V  K  S  V
```

Figure 6L

```
         5950        5960        5970        5980        5990        6000
   CTTTCATTGCCAAGTTTGTTTCACAAAAAAAGCCTTAGGCATCTCCTATGGCAGGAAGAA
    L  S  L  P  S  L  F  H  K  K  S  L  R  H  L  L  W  Q  E  E
     F  H  C  Q  V  C  F  T  K  K  A  L  G  I  S  Y  G  R  K  K
   A  F  I  A  K  F  V  S  Q  K  K  P  *  A  S  P  M  A  G  R 6010        6020        6030        6040        6050        6060
   GCGGAGACAGCGACGAAGAGCTCCTGAAGACAGTCAGACTCATCAAGTTTCTCTACCAAA
    A  E  T  A  T  K  S  S  *  R  Q  S  D  S  S  S  F  S  T  K
     R  R  Q  R  R  R  A  P  E  D  S  Q  T  H  Q  V  S  L  P  K
   S  G  D  S  D  E  E  L  L  K  T  V  R  L  I  K  F  L  Y  Q 6070        6080        6090        6100        6110        6120
   GCAGTAAGTAGTACATGTAATGCAACCTTTAGTAATAGCAGCAATAGTAGCATTAGTAGT
    A  V  S  S  T  C  N  A  T  F  S  N  S  S  N  S  S  I  S  S
     Q  *  V  V  H  V  M  Q  P  L  V  I  A  A  I  V  A  L  V  V
   S  S  K  *  Y  M  *  C  N  L  *  *  *  Q  Q  *  *  H  *  *

6130        6140        6150        6160        6170        6180
   AGCAGGAATAATAGCAATAGTTGTGTGATCCATAGTATTCATAGAATATAGGAAAATAAG
    S  R  N  N  S  N  S  C  V  I  H  S  I  H  R  I  *  E  N  K
     A  G  I  I  A  I  V  V  *  S  I  V  F  I  E  Y  R  K  I  R
   *  Q  E  *  *  Q  *  L  C  D  P  *  Y  S  *  N  I  G  K  *

6190        6200        6210        6220        6230        6240
   AAGACAAAGAAAAATAGACAGGGTAATTGACAGAATAAGCGAAAGAGCAGAAGACAGTGG
    K  T  K  K  N  R  Q  G  N  *  Q  N  K  R  K  S  R  R  Q  W
     R  Q  R  K  I  D  R  V  I  D  R  I  S  E  R  A  E  D  S  G
   E  D  K  E  K  *  T  G  *  L  T  E  *  A  K  E  Q  K  T  V 6250        6260        6270        6280        6290        6300
   CAATGAGAGTGAAGGGGATCAGGAGGAATTATCAGCACTGGTGGGGATGGGGCACGATGC
    Q  *  E  *  R  G  S  G  G  I  I  S  T  G  G  D  G  A  R  C
     N  E  S  E  G  D  Q  E  E  L  S  A  L  V  G  M  G  H  D  A
   A  M  R  V  K  G  I  R  R  N  Y  Q  H  W  W  G  W  G  T  M 6310        6320        6330        6340        6350        6360
   TCCTTGGGTTATTAATGATCTGTAGTGCTACAGAAAAATTGTGGGTCACAGTCTATTATG
    S  L  G  Y  *  *  S  V  V  L  Q  K  N  C  G  S  Q  S  I  M
     P  W  V  I  N  D  L  *  C  Y  R  K  I  V  G  H  S  L  L  W
   L  L  G  L  L  M  I  C  S  A  T  E  K  L  W  V  T  V  Y  Y 6370        6380        6390        6400        6410        6420
   GGGTACCTGTGTGGAAAGAAGCAACCACCACTCTATTTTGTGCATCAGATGCTAAAGCAT
    G  Y  L  C  G  K  K  Q  P  P  L  Y  F  V  H  Q  M  L  K  H
     G  T  C  V  E  R  S  N  H  H  S  I  L  C  I  R  C  *  S  I
   G  V  P  V  W  K  E  A  T  T  T  L  F  C  A  S  D  A  K  A 6430        6440        6450        6460        6470        6480
   ATGATACAGAGGTACATAATGTTTGGGCCACACATGCCTGTGTACCCACAGACCCCAACC
    M  I  Q  R  Y  I  M  F  G  P  H  M  P  V  Y  P  Q  T  P  T
     *  Y  R  G  T  *  C  L  G  H  T  C  L  C  T  H  R  P  Q  P
   Y  D  T  E  V  H  N  V  W  A  T  H  A  C  V  P  T  D  P  N
```

Figure 6M

```
         6490        6500        6510        6520        6530        6540
    CACAAGAAGTAGAATTGGTAAATGTGACAGAAAATTTTAACATGTGGAAAAATAACATGG
      H  K  K  *  N  W  *  M  *  Q  K  I  L  T  C  G  K  I  T  W
        T  R  S  R  I  G  K  C  D  R  K  F  *  H  V  E  K  *  H  G
      P  Q  E  V  E  L  V  N  V  T  E  N  F  N  M  W  K  N  N  M 6550        6560        6570        6580        6590        6600
    TAGAACAGATGCATGAGGATATAATCAGTTTATGGATCAAAGCCTAAAGCCATGTGTAA
      *  N  R  C  M  R  I  *  S  V  Y  G  I  K  A  *  S  H  V  *
        R  T  D  A  *  G  Y  N  Q  F  M  G  S  K  P  K  A  M  C  K
      V  E  Q  M  H  E  D  I  I  S  L  W  D  Q  S  L  K  P  C  V 6610        6620        6630        6640        6650        6660
    AATTAACCCCACTCTGTGTTACTTTAAATTGCACTGATTTGAGGAATACTACTAATACCA
      N  *  P  H  S  V  L  L  *  I  A  L  I  *  G  I  L  L  I  P
        I  N  P  T  L  C  Y  F  K  L  H  *  F  E  E  Y  Y  *  Y  Q
      K  L  T  P  L  C  V  T  L  N  C  T  D  L  R  N  T  T  N  T 6670        6680        6690        6700        6710        6720
    ATAATAGTACTGCTAATAACAATAGTAATAGCGAGGGAACAATAAAGGGAGGAGAAATGA
      I  I  V  L  L  I  T  I  V  I  A  R  E  Q  *  R  E  E  K  *
        *  *  Y  C  *  *  Q  *  *  *  R  G  N  N  K  G  R  R  N  E
      N  N  S  T  A  N  N  N  S  N  S  E  G  T  I  K  G  G  E  M 6730        6740        6750        6760        6770        6780
    AAAACTGCTCTTTCAATATCACCACAAGCATAAGAGATAAGATGCAGAAAGAATATGCAC
      K  T  A  L  S  I  S  P  Q  A  *  E  I  R  C  R  K  N  M  H
        K  L  L  F  Q  Y  H  H  K  H  K  R  *  D  A  E  R  I  C  T
      K  N  C  S  F  N  I  T  T  S  I  R  D  K  M  Q  K  E  Y  A 6790        6800        6810        6820        6830        6840
    TTCTTTATAAACTTGATATAGTATCAATAAATAATGATAGTACCAGCTATAGGTTGATAA
      F  F  I  N  L  I  *  Y  Q  *  I  M  I  V  P  A  I  G  *  *
        S  L  *  T  *  Y  S  I  N  K  *  *  *  Y  Q  L  *  V  D  K
      L  L  Y  K  L  D  I  V  S  I  N  N  D  S  T  S  Y  R  L  I 6850        6860        6870        6880        6890        6900
    GTTGTAATACCTCAGTCATTACACAAGCTTGTCCAAAGATATCCTTTGAGCCAATTCCCA
      V  V  I  P  Q  S  L  H  K  L  V  Q  R  Y  P  L  S  Q  F  P
        L  *  Y  L  S  H  Y  T  S  L  S  K  D  I  L  *  A  N  S  H
      S  C  N  T  S  V  I  T  Q  A  C  P  K  I  S  F  E  P  I  P 6910        6920        6930        6940        6950        6960
    TACACTATTGTGCCCCGGCTGGTTTTGCGATTCTAAAGTGTAACGATAAAAAGTTCAGTG
      Y  T  I  V  P  R  L  V  L  R  F  *  S  V  T  I  K  S  S  V
        T  L  L  C  P  G  W  F  C  D  S  K  V  *  R  *  K  V  Q  W
      I  H  Y  C  A  P  A  G  F  A  I  L  K  C  N  D  K  K  F  S 6970        6980        6990        7000        7010        7020
    GAAAAGGATCATGTAAAAATGTCAGCACAGTACAATGTACACATGGAATTAGGCCAGTAG
      E  K  D  H  V  K  M  S  A  Q  Y  N  V  H  M  E  L  G  Q  *
        K  R  I  M  *  K  C  Q  H  S  T  M  Y  T  W  N  *  A  S  S
      G  K  G  S  C  K  N  V  S  T  V  Q  C  T  H  G  I  R  P  V
```

Figure 6N

```
          7030      7040      7050      7060      7070      7080
TATCAACTCAACTGCTGTTAAATGGCAGTCTAGCAGAAGAAGAGGTAGTAATTAGATCTG
  Y  Q  L  N  C  C  *  M  A  V  *  Q  K  K  R  *  *  L  D  L
   I  N  S  T  A  V  K  W  Q  S  S  R  R  R  G  S  N  *  I  *
 V  S  T  Q  L  L  L  N  G  S  L  A  E  E  E  V  V  I  R  S 7090      7100      7110      7120      7130      7140
AGAATTTCAATGATAATGCTAAAACCATCATAGTACATCTGAATGAATCTGTACAAATTA
  R  I  S  M  I  M  L  K  P  S  *  Y  I  *  M  N  L  Y  K  L
   E  F  Q  *  *  C  *  N  H  H  S  T  S  E  *  I  C  T  N  *
 E  N  F  N  D  N  A  K  T  I  I  V  H  L  N  E  S  V  Q  I 7150      7160      7170      7180      7190      7200
ATTGTACAAGACCCAACTACAATAAAAGAAAAAGGATACATATAGGACCAGGGAGAGCAT
  I  V  Q  D  P  T  T  I  K  E  K  G  Y  I  *  D  Q  G  E  H
   L  Y  K  T  Q  L  Q  *  K  K  K  D  T  Y  R  T  R  E  S  I
 N  C  T  R  P  N  Y  N  K  R  K  R  I  H  I  G  P  G  R  A 7210      7220      7230      7240      7250      7260
TTTATACAACAAAAAATATAATAGGAACTATAAGACAAGCACATTGTAACATTAGTAGAG
  F  I  Q  Q  K  I  *  *  E  L  *  D  K  H  I  V  T  L  V  E
   L  Y  N  K  K  Y  N  R  N  Y  K  T  S  T  L  *  H  *  *  S
 F  Y  T  T  K  N  I  I  G  T  I  R  Q  A  H  C  N  I  S  R 7270      7280      7290      7300      7310      7320
CAAAATGGAATGACACTTTAAGACAGATAGTTAGCAAATTAAAAGAACAATTTAAGAATA
  Q  N  G  M  T  L  *  D  R  *  L  A  N  *  K  N  N  L  R  I
   K  M  E  *  H  F  K  T  D  S  *  Q  I  K  R  T  I  *  E  *
 A  K  W  N  D  T  L  R  Q  I  V  S  K  L  K  E  Q  F  K  N 7330      7340      7350      7360      7370      7380
AAACAATAGTCTTTAATCAATCCTCAGGAGGGGACCCAGAAATTGTAATGCACAGTTTTA
  K  Q  *  S  L  I  N  P  Q  E  G  T  Q  K  L  *  C  T  V  L
   N  N  S  L  *  S  I  L  R  R  G  P  R  N  C  N  A  Q  F  *
 K  T  I  V  F  N  Q  S  S  G  G  D  P  E  I  V  M  H  S  F 7390      7400      7410      7420      7430      7440
ATTGTGGAGGGGAATTTTTCTACTGTAATACATCACCACTGTTTAATAGTACTTGGAATG
  I  V  E  G  N  F  S  T  V  I  H  H  H  C  L  I  V  L  G  M
   L  W  R  G  I  F  L  L  *  Y  I  T  T  V  *  *  Y  L  E  W
 N  C  G  G  E  F  F  Y  C  N  T  S  P  L  F  N  S  T  W  N 7450      7460      7470      7480      7490      7500
GTAATAATACTTGGAATAATACTACAGGGTCAAATAACAATATCACACTTCAATGCAAAA
  V  I  I  L  G  I  I  L  Q  G  Q  I  T  I  S  H  F  N  A  K
   *  *  Y  L  E  *  Y  Y  R  V  K  *  Q  Y  H  T  S  M  Q  N
 G  N  N  T  W  N  N  T  T  G  S  N  N  N  I  T  L  Q  C  K 7510      7520      7530      7540      7550      7560
TAAAACAAATTATAAACATGTGGCAGGAAGTAGGAAAAGCAATATATGCCCCTCCCATTG
  *  N  K  L  *  T  C  G  R  K  *  E  K  Q  Y  M  P  L  P  L
   K  T  N  Y  K  H  V  A  G  S  R  K  S  N  I  C  P  S  H  *
 I  K  Q  I  I  N  M  W  Q  E  V  G  K  A  I  Y  A  P  P  I
```

Figure 6O

```
          7570        7580        7590        7600        7610        7620
    AAGGACAAATTAGATGTTCATCAAATATTACAGGGCTACTATTAACAAGAGATGGTGGTA
      K  D  K  L  D  V  H  Q  I  L  Q  G  Y  Y  *  Q  E  M  V  V
       R  T  N  *  M  F  I  K  Y  Y  R  A  T  I  N  K  R  W  W  *
    E  G  Q  I  R  C  S  S  N  I  T  G  L  L  L  T  R  D  G  G 7630        7640        7650        7660        7670        7680
    AGGACACGGACACGAACGACACCGAGATCTTCAGACCTGGAGGAGGAGATATGAGGGACA
      R  T  R  T  R  T  T  P  R  S  S  D  L  E  E  E  I  *  G  T
       G  H  G  H  E  R  H  R  D  L  Q  T  W  R  R  R  Y  E  G  Q
    K  D  T  D  T  N  D  T  E  I  F  R  P  G  G  G  D  M  R  D 7690        7700        7710        7720        7730        7740
    ATTGGAGAAGTGAATTATATAAATATAAAGTAGTAACAATTGAACCATTAGGAGTAGCAC
      I  G  E  V  N  Y  I  N  I  K  *  *  Q  L  N  H  *  E  *  H
       L  E  K  *  I  I  *  I  *  S  S  N  N  *  T  I  R  S  S  T
    N  W  R  S  E  L  Y  K  Y  K  V  V  T  I  E  P  L  G  V  A 7750        7760        7770        7780        7790        7800
    CCACCAAGGCAAAGAGAAGAGTGGTGCAGAGAGAAAAAAGAGCAGCGATAGGAGCTCTGT
      P  P  R  Q  R  E  E  W  C  R  E  K  K  E  Q  R  *  E  L  C
       H  Q  G  K  E  K  S  G  A  E  R  K  K  S  S  D  R  S  S  V
    S  T  K  A  K  R  R  V  V  Q  R  E  K  R  A  A  I  G  A  L 7810        7820        7830        7840        7850        7860
    TCCTTGGGTTCTTAGGAGCAGCAGGAAGCACTATGGGCGCAGCGTCAGTGACGCTGACGG
      S  L  G  S  *  E  Q  Q  E  A  L  W  A  Q  R  Q  *  R  *  R
       P  W  V  L  R  S  S  R  K  H  Y  G  R  S  V  S  D  A  D  G
    F  L  G  F  L  G  A  A  G  S  T  M  G  A  A  S  V  T  L  T 7870        7880        7890        7900        7910        7920
    TACAGGCCAGACTATTATTGTCTGGTATAGTGCAACAGCAGAACAATTTGCTGAGGGCCA
      Y  R  P  D  Y  Y  C  L  V  *  C  N  S  R  T  I  C  *  G  P
       T  G  Q  T  I  I  V  W  Y  S  A  T  A  E  Q  F  A  E  G  H
    V  Q  A  R  L  L  L  S  G  I  V  Q  Q  Q  N  N  L  L  R  A 7930        7940        7950        7960        7970        7980
    TTGAGGCGCAACAGCATATGTTGCAACTCACAGTCTGGGGCATCAAGCAGCTCCAGGCAA
      L  R  R  N  S  I  C  C  N  S  Q  S  G  A  S  S  S  R  Q
       *  G  A  T  A  Y  V  A  T  H  S  L  G  H  Q  A  A  P  G  K
    I  E  A  Q  Q  H  M  L  Q  L  T  V  W  G  I  K  Q  L  Q  A 7990        8000        8010        8020        8030        8040
    GAATCCTGGCTGTGGAAAGATACCTAAAGGATCAACAGCTCCTGGGGATTTGGGGTTGCT
      E  S  W  L  W  K  D  T  *  R  I  N  S  S  W  G  F  G  V  A
       N  P  G  C  G  K  I  P  K  G  S  T  A  P  G  D  L  G  L  L
    R  I  L  A  V  E  R  Y  L  K  D  Q  Q  L  L  G  I  W  G  C 8050        8060        8070        8080        8090        8100
    CTGGAAAAACTCATTTGCACCACTACTGTGCCTTGGAATGCTAGTTGGAGTAATAAATCTC
      L  E  N  S  F  A  P  L  L  C  L  G  M  L  V  G  V  I  N  L
       W  K  T  H  L  H  H  Y  C  A  L  E  C  *  L  E  *  *  I  S
    S  G  K  L  I  C  T  T  T  V  P  W  N  A  S  W  S  N  K  S
```

Figure 6P

```
         8110       8120       8130       8140       8150       8160
      TGGATGATATTTGGAATAACATGACCTGGATGCAGTGGGAAAGAGAAATTGACAATTACA
       W  M  I  F  G  I  T  *  P  G  C  S  G  K  E  K  L  T  I  T
        G  *  Y  L  E  *  H  D  L  D  A  V  G  K  R  N  *  Q  L  H
       L  D  D  I  W  N  N  M  T  W  M  Q  W  E  R  E  I  D  N  Y 8170       8180       8190       8200       8210       8220
      CAAGCTTAATATACTCATTACTAGAAAAATCGCAAACCCAACAAGAAATGAATGAACAAG
       Q  A  *  Y  T  H  Y  *  K  N  R  K  P  N  K  K  *  M  N  K
        K  L  N  I  L  I  T  R  K  I  A  N  P  T  R  N  E  *  T  R
       T  S  L  I  Y  S  L  L  E  K  S  Q  T  Q  Q  E  M  N  E  Q 8230       8240       8250       8260       8270       8280
      AATTATTGGAATTGGATAAATGGGCAAGTTTGTGGAATTGGTTTGACATAACAAATTGGC
       N  Y  W  N  W  I  N  G  Q  V  C  G  I  G  L  T  *  Q  I  G
        I  I  G  I  G  *  M  G  K  F  V  E  L  V  *  H  N  K  L  A
       E  L  L  E  L  D  K  W  A  S  L  W  N  W  F  D  I  T  N  W 8290       8300       8310       8320       8330       8340
      TGTGGTATATAAAAATATTCATAATGATAGTAGGAGGCTTGGTAGGTTTAAGAATAGTTT
       C  G  I  *  K  Y  S  *  *  *  *  E  A  W  *  V  *  E  *  F
        V  V  Y  K  N  I  H  N  D  S  R  R  L  G  R  F  K  N  S  F
       L  W  Y  I  K  I  F  I  M  I  V  G  G  L  V  G  L  R  I  V 8350       8360       8370       8380       8390       8400
      TTGCTGTACTTTCTATAGTGAATAGAGTTAGGCAGGGATACTCACCATTGTCGTTGCAGA
       L  L  Y  F  L  *  *  I  E  L  G  R  D  T  H  H  C  R  C  R
        C  C  T  F  Y  S  E  *  S  *  A  G  I  L  T  I  V  V  A  D
       F  A  V  L  S  I  V  N  R  V  R  Q  G  Y  S  P  L  S  L  Q 8410       8420       8430       8440       8450       8460
      CCCGCCCCCCAGTTCCGAGGGGACCCGACAGGCCCGAAGGAATCGAAGAAGAAGGTGGAG
       P  A  P  Q  F  R  G  D  P  T  G  P  K  E  S  K  K  K  V  E
        P  P  P  S  S  E  G  T  R  Q  A  R  R  N  R  R  R  R  W  R
       T  R  P  P  V  P  R  G  P  D  R  P  E  G  I  E  E  E  G  G 8470       8480       8490       8500       8510       8520
      AGAGAGACAGAGACACATCCGGTCGATTAGTGCATGGATTCTTAGCAATTATCTGGGTCG
       R  E  T  E  T  H  P  V  D  *  C  M  D  S  *  Q  L  S  G  S
        E  R  Q  R  H  I  R  S  I  S  A  W  I  L  S  N  Y  L  G  R
       E  R  D  R  D  T  S  G  R  L  V  H  G  F  L  A  I  I  W  V 8530       8540       8550       8560       8570       8580
      ACCTGCGGAGCCTGTTCCTCTTCAGCTACCACCACTTGAGAGACTTACTCTTGATTGCAG
       T  C  G  A  C  S  S  S  A  T  T  T  *  E  T  Y  S  *  L  Q
        P  A  E  P  V  P  L  Q  L  P  P  L  E  R  L  T  L  D  C  S
       D  L  R  S  L  F  L  F  S  Y  H  H  L  R  D  L  L  L  I  A 8590       8600       8610       8620       8630       8640
      CGAGGATTGTGGAACTTCTGGGACGCAGGGGGTGGGAAGTCCTCAAATATTGGTGGAATC
       R  G  L  W  N  F  W  D  A  G  G  G  K  S  S  N  I  G  G  I
        E  D  C  G  T  S  G  T  Q  G  V  G  S  P  Q  I  L  V  E  S
       A  R  I  V  E  L  L  G  R  R  G  W  E  V  L  K  Y  W  W  N
```

Figure 6Q

```
        8650        8660        8670        8680        8690        8700
TCCTACAGTATTGGAGTCAGGAACTAAAGAGTAGTGCTGTTAGCTTGCTTAATGCCACAG
  S  Y  S  I  G  V  R  N  *  R  V  V  L  L  A  C  L  M  P  Q
   P  T  V  L  E  S  G  T  K  E  *  C  C  *  L  A  *  C  H  R
 L  L  Q  Y  W  S  Q  E  L  K  S  S  A  V  S  L  L  N  A  T 8710        8720        8730        8740        8750        8760
ATATAGCAGTAGCTGAGGGGACAGATAGGGTTATAGAAGTACTGCAAAGAGCTGGTAGAG
  I  *  Q  *  L  R  G  Q  I  G  L  *  K  Y  C  K  E  L  V  E
   Y  S  S  S  *  G  D  R  *  G  Y  R  S  T  A  K  S  W  *  S
 D  I  A  V  A  E  G  T  D  R  V  I  E  V  L  Q  R  A  G  R 8770        8780        8790        8800        8810        8820
CTATTCTCCACATACCTACAAGAATAAGACAGGGCTTGGAAAGGGCTTTGCTATAAGATG
  L  F  S  T  Y  L  Q  E  *  D  R  A  W  K  G  L  C  Y  K  M
   Y  S  P  H  T  Y  K  N  K  T  G  L  G  K  G  F  A  I  R  W
 A  I  L  H  I  P  T  R  I  R  Q  G  L  E  R  A  L  L  *  D 8830        8840        8850        8860        8870        8880
GGTGGCAAATGGTCAAAACGTGTGACTGGATGGCCTACTGTAAGGGAAAAAATGAGACGA
  G  G  K  W  S  K  R  V  T  G  W  P  T  V  R  E  K  M  R  R
   V  A  N  G  Q  N  V  *  L  D  G  L  L  *  G  K  K  *  D  E
 G  W  Q  M  V  K  T  C  D  W  M  A  Y  C  K  G  K  N  E  T 8890        8900        8910        8920        8930        8940
GCTGAACCAGCTGAGCCAGCAGCAGATGGGGTGGGAGCAGCATCCCGAGACCTGGAAAAA
  A  E  P  A  E  P  A  A  D  G  V  G  A  A  S  R  D  L  E  K
   L  N  Q  L  S  Q  Q  Q  M  G  W  E  Q  H  P  E  T  W  K  N
 S  *  T  S  *  A  S  S  R  W  G  G  S  S  I  P  R  P  G  K 8950        8960        8970        8980        8990        9000
CATGGAGCACTCACAAGTAGCAATACAGCAGCTACCAATGCTGATTGTGCCTGGCTAGAA
  H  G  A  L  T  S  S  N  T  A  A  T  N  A  D  C  A  W  L  E
   M  E  H  S  Q  V  A  I  Q  Q  L  P  M  L  I  V  P  G  *  K
 T  W  S  T  H  K  *  Q  Y  S  S  Y  Q  C  *  L  C  L  A  R 9010        9020        9030        9040        9050        9060
GCACAAGAGGAGGAGGAAGTGGGTTTTCCAGTCAGACCTCAGGTACCTTTAAGACCAATG
  A  Q  E  E  E  E  V  G  F  P  V  R  P  Q  V  P  L  R  P  M
   H  K  R  R  R  K  W  V  F  Q  S  D  L  R  Y  L  *  D  Q  *
 S  T  R  G  G  G  S  G  F  S  S  Q  T  S  G  T  F  K  T  N 9070        9080        9090        9100        9110        9120
ACTTACAAAGCAGCTTTAGATCTTAGCCACTTTTTAAAAGAAAAGGGGGGACTGGATGGG
  T  Y  K  A  A  L  D  L  S  H  F  L  K  E  K  G  G  L  D  G
   L  T  K  Q  L  *  I  L  A  T  F  *  K  K  R  G  D  W  M  G
 D  L  Q  S  S  F  R  S  *  P  L  F  K  R  K  G  G  T  G  W 9130        9140        9150        9160        9170        9180
TTAATTTACTCCCAAAAGAGACAAGACATCCTTGATCTGTGGGTCTACCACACACAAGGC
  L  I  Y  S  Q  K  R  Q  D  I  L  D  L  W  V  Y  H  T  Q  G
   *  F  T  P  K  R  D  K  T  S  L  I  C  G  S  T  T  H  K  A
 V  N  L  L  P  K  E  T  R  H  P  *  S  V  G  L  P  H  T  R
```

Figure 6R

```
         9190        9200        9210        9220        9230        9240
    TACTTCCCTGATTGGCAGAACTACACACCAGGGCCAGGGATCAGATATCCACTGACCTTT
     Y  F  P  D  W  Q  N  Y  T  P  G  P  G  I  R  Y  P  L  T  F
       T  S  L  I  G  R  T  T  H  Q  G  Q  G  S  D  I  H  *  P  L
     L  L  P  *  L  A  E  L  H  T  R  A  R  D  Q  I  S  T  D  L 9250        9260        9270        9280        9290        9300
    GGATGGTGCTTCAAGCTAGTACCAGTTGAGCCAGAGAAGATAGAAGAGGCCAATAAAGGA
     G  W  C  F  K  L  V  P  V  E  P  E  K  I  E  E  A  N  K  G
       D  G  A  S  S  *  Y  Q  L  S  Q  R  R  *  K  R  P  I  K  E
     W  M  V  L  Q  A  S  T  S  *  A  R  E  D  R  R  G  Q  *  R 9310        9320        9330        9340        9350        9360
    GAGAACAACTGCTTGTTACACCCTATGAGCCAGCATGGGATGGATGACCCGGAGAGAGAA
     E  N  N  C  L  L  H  P  M  S  Q  H  G  M  D  D  P  E  R  E
       R  T  T  A  C  Y  T  L  *  A  S  M  G  W  M  T  R  R  E  K
     R  E  Q  L  L  V  T  P  Y  E  P  A  W  D  G  *  P  G  E  R 9370        9380        9390        9400        9410        9420
    GTGTTAGTGTGGAAGTCTGACAGCCACCTAGCATTTCAGCATTATGCCCGAGAGCTGCAT
     V  L  V  W  K  S  D  S  H  L  A  F  Q  H  Y  A  R  E  L  H
       C  *  C  G  S  L  T  A  T  *  H  F  S  I  M  P  E  S  C  I
     S  V  S  V  E  V  *  Q  P  P  S  I  S  A  L  C  P  R  A  A 9430        9440        9450        9460        9470        9480
    CCGGAGTACTACAAGAACTGCTGACATCGAGCTATCTACAAGGGACTTTCCGCTGGGGAC
     P  E  Y  Y  K  N  C  *  H  R  A  I  Y  K  G  L  S  A  G  D
       R  S  T  T  R  T  A  D  I  E  L  S  T  R  D  F  P  L  G  T
     S  G  V  L  Q  E  L  L  T  S  S  Y  L  Q  G  T  F  R  W  G 9490        9500        9510        9520        9530        9540
    TTTCCAGGGAGGTGTGGCCTGGGCGGGACCGGGGAGTGGCGAGCCCTCAGATGCTGCATA
     F  P  G  R  C  G  L  G  G  T  G  E  W  R  A  L  R  C  C  I
       F  Q  G  G  V  A  W  A  G  P  G  S  G  E  P  S  D  A  A  Y
     L  S  R  E  V  W  P  G  R  D  R  G  V  A  S  P  Q  M  L  H 9550        9560        9570        9580        9590        9600
    TAAGCAGCTGCTTTCTGCCTGTACTGGGTCTCTCTGGTTAGACCAGATCTGAGCCTGGGA
     *  A  A  A  F  C  L  Y  W  V  S  L  V  R  P  D  L  S  L  G
       K  Q  L  L  S  A  C  T  G  S  L  W  L  D  Q  I  *  A  W  E
     I  S  S  C  F  L  P  V  L  G  L  S  G  *  T  R  S  E  P  G 9610        9620        9630        9640        9650        9660
    GCTCTCTGGCTAACTAGGGAACCCACTGCTTAAGCCTCAATAAAGCTTGCCTTGAGTGCT
     A  L  W  L  T  R  E  P  T  A  *  A  S  I  K  L  A  L  S  A
       L  S  G  *  L  G  N  P  L  L  K  P  Q  *  S  L  P  *  V  L
     S  S  L  A  N  *  G  T  H  C  L  S  L  N  K  A  C  L  E  C 9670        9680        9690        9700        9710        9720
    TCAAGTAGTGTGTGCCCGTCTGTTATGTGACTCTGGTAGCTAGAGATCCCTCAGATCCTT
     S  S  S  V  C  P  S  V  M  *  L  W  *  L  E  I  P  Q  I  L
       Q  V  V  C  A  R  L  L  C  D  S  G  S  *  R  S  L  R  S  F
     F  K  *  C  V  P  V  C  Y  V  T  L  V  A  R  D  P  S  D  P
```

Figure 6S

```
       9730           9740
TTAGGCAGTGTGGAAAATCTCTAGCA
  L   G   S   V   E   N   L   *
    *   A   V   W   K   I   S   S
  F   R   Q   C   G   K   S   L   A
```

Figure 8A

```
         10        20        30        40        50        60
GATCAAGGGCCACAGAGGGAGCCACACAATGAATGGACACTAGAGCTTTTAGAGGAGCTT
  D  Q  G  P  Q  R  E  P  H  N  E  W  T  L  E  L  L  E  E  L
   I  K  G  H  R  G  S  H  T  M  N  G  H  *  S  F  *  R  S  L
    S  R  A  T  E  G  A  T  Q  *  M  D  T  R  A  F  R  G  A 70        80        90       100       110       120
AAGAGTGAAGCTGTTAGACACTTTCCTAGGATATGGCTTCATGGCTTAGGGCAACATATC
  K  S  E  A  V  R  H  F  P  R  I  W  L  H  G  L  G  Q  H  I
   R  V  K  L  L  D  T  F  L  G  Y  G  F  M  A  *  G  N  I  S
    *  E  *  S  C  *  T  L  S  *  D  M  A  S  W  L  R  A  T  Y 130       140       150       160       170       180
TATGAAACTTATGGGGATACTTGGGCAGGAGTGGAAGCCATAATAAGAATTCTGCAACAA
  Y  E  T  Y  G  D  T  W  A  G  V  E  A  I  I  R  I  L  Q  Q
   M  K  L  M  G  I  L  G  Q  E  W  K  P  *  *  E  F  C  N  N
  L  *  N  L  W  G  Y  L  G  R  S  G  S  H  N  K  N  S  A  T 190       200       210       220       230       240
CTGCTGTTTATCCATTTCAGGATTGGGTGCCAACATAGCAGAATAGGTATTATTCAACAG
  L  L  F  I  H  F  R  I  G  C  Q  H  S  R  I  G  I  I  Q  Q
   C  C  L  S  I  S  G  L  G  A  N  I  A  E  *  V  L  F  N  R
    T  A  V  Y  P  F  Q  D  W  V  P  T  *  Q  N  R  Y  Y  S  T 250       260       270       280       290       300
AGGAGAGCAAGAAATGGAGCCAGTAGATCCTAAACTAGAGCCCTGGAAGCATCCAGGAAG
  R  R  A  R  N  G  A  S  R  S  *  T  R  A  L  E  A  S  R  K
   G  E  Q  E  M  E  P  V  D  P  K  L  E  P  W  K  H  P  G  S
    E  E  S  K  K  W  S  Q  *  I  L  N  *  S  P  G  S  I  Q  E 310       320       330       340       350       360
TCAGCCTAAGACTGCTTGTACCACTTGCTATTGTAAAAAGTGTTGCTTTCATTGCCAAGT
  S  A  *  D  C  L  Y  H  L  L  *  K  V  L  L  S  L  P  S
   Q  P  K  T  A  C  T  T  C  Y  C  K  K  C  C  F  H  C  Q  V
    V  S  L  R  L  L  V  P  L  A  I  V  K  S  V  A  F  I  A  K 370       380       390       400       410       420
TTGCTTCATAACAAAAGGCTTAGGCATCTCCTATGGCAGGAAGAAGCGGAGACAGCGACG
  L  L  H  N  K  R  L  R  H  L  L  W  Q  E  E  A  E  T  A  T
   C  F  I  T  K  G  L  G  I  S  Y  G  R  K  K  R  R  Q  R  R
    F  A  S  *  Q  K  A  *  A  S  P  M  A  G  R  S  G  D  S  D
                                         (Rev)
        430       440       450       460       470       480
AAGAGCTCCTCAAGACAGTGAGACTCATCAAGTTTCTCTATCAAAGCAGTAAGTAGTACA
  K  S  S  S  R  Q  *  D  S  S  S  F  S  I  K  A  V  S  S  T
   R  A  P  Q  D  S  E  T  H  Q  V  S  L  S  K  Q  *  V  V  H
    E  E  L  L  K  T  V  R  L  I  K  F  L  Y  Q  S  S  K  *  Y 490       500       510       520       530       540
TGTAATGCAAGCTTTACAAATATCAGCTATAGTAGGATTAGTAGTAGCAGCAATAATAGC
  C  N  A  S  F  T  N  I  S  Y  S  R  I  S  S  S  N  N  S
   V  M  Q  A  L  Q  I  S  A  I  V  G  L  V  V  A  A  I  I  A
    M  *  C  K  L  Y  K  Y  Q  L  *  *  D  *  *  *  Q  Q  *  *
```

Figure 8B

```
          550       560       570       580       590       600
      AATAGTTGTGTGGACCATAGTATTCATAGAATATAGGAAAATATTAAGGCAAAGAAAAAT
        N  S  C  V  D  H  S  I  H  R  I  *  E  N  I  K  A  K  K  N
         I  V  V  W  T  I  V  F  I  E  Y  R  K  I  L  R  Q  R  K  I
       Q  *  L  C  G  P  *  Y  S  *  N  I  G  K  Y  *  G  K  E  K 610       620       630       640       650       660
      AGACAGGTTAATTGATAGAATAACAGAAAGAGCAGAAGACAGTGGCAATGAGAGTGACGG
        R  Q  V  N  *  *  N  N  R  K  S  R  R  Q  W  Q  *  E  *  R
         D  R  L  I  D  R  I  T  E  R  A  E  D  S  G  N  E  S  D  G
       *  T  G  *  L  I  E  *  Q  K  E  Q  K  T  V  A  M  R  V  T
                                                         (Env)
          670       680       690       700       710       720
      AGATCAGGAAGAGTTATCAGCACTGGTGGAGATGGGGCATCATGCTCCTTGGGATATTAA
        R  S  G  R  V  I  S  T  G  G  D  G  A  S  C  S  L  G  Y  *
         D  Q  E  E  L  S  A  L  V  E  M  G  H  H  A  P  W  D  I  N
       E  I  R  K  S  Y  Q  H  W  W  R  W  G  I  M  L  L  G  I  L 730       740       750       760       770       780
      TGATCTGTAATGCTGAAGAAAAATTGTGGGTCACAGTCTATTATGGGGTACCTGTGTGGA
        *  S  V  M  L  K  K  N  C  G  S  Q  S  I  M  G  Y  L  C  G
         D  L  *  C  *  R  K  I  V  G  H  S  L  L  W  G  T  C  V  E
       M  I  C  N  A  E  E  K  L  W  V  T  V  Y  Y  G  V  P  V  W 790       800       810       820       830       840
      AAGAAGCAACCACCACTCTATTTTGTGCATCAGATCGTAAAGCATATGATACAGAGGTAC
        K  K  Q  P  P  L  Y  F  V  H  Q  I  V  K  H  M  I  Q  R  Y
         R  S  N  H  H  S  I  L  C  I  R  S  *  S  I  *  Y  R  G  T
       K  E  A  T  T  T  L  F  C  A  S  D  R  K  A  Y  D  T  E  V 850       860       870       880       890       900
      ATAATGTTTGGGCCACACATGCCTGTGTACCCACAGACCCCAACCCACAAGAAGTAGAAT
        I  M  F  G  P  H  M  P  V  Y  P  Q  T  P  T  H  K  K  *  N
         *  C  L  G  H  T  C  L  C  T  H  R  P  Q  P  T  R  S  R  I
       H  N  V  W  A  T  H  A  C  V  P  T  D  P  N  P  Q  E  V  E 910       920       930       940       950       960
      TGAAAAATGTGACAGAAAATTTTAACATGTGGAAAAATAACATGGTAGAACAAATGCATG
        *  K  M  *  Q  K  I  L  T  C  G  K  I  T  W  *  N  K  C  M
         E  K  C  D  R  K  F  *  H  V  E  K  *  H  G  R  T  N  A  *
       L  K  N  V  T  E  N  F  N  M  W  K  N  N  M  V  E  Q  M  H 970       980       990      1000      1010      1020
      AGGATATAATCAGTTTATGGGATCAAAGCCTAAAGCCATGTGTAAAATTAACCCCACTCT
        R  I  *  S  V  Y  G  I  K  A  *  S  H  V  *  N  *  P  H  S
         G  Y  N  Q  F  M  G  S  K  P  K  A  M  C  K  I  N  P  T  L
       E  D  I  I  S  L  W  D  Q  S  L  K  P  C  V  K  L  T  P  L 1030      1040      1050      1060      1070      1080
      GTGTTACTTTAAATTGCACTGATTTGAGGAATGCTACTAATGGGAATGACACTAATACCA
        V  L  L  *  I  A  L  I  *  G  M  L  L  M  G  M  T  L  I  P
         C  Y  F  K  L  H  *  F  E  E  C  Y  *  W  E  *  H  *  Y  H
       C  V  T  L  N  C  T  D  L  R  N  A  T  N  G  N  D  T  N  T
```

Figure 8C

```
         1090        1100       1110       1120       1130       1140
    CTAGTAGTAGCAGGGGAATGGTGGGGGGAGGAGAAATGAAAAATTGCTCTTTCAATATCA
      L  V  V  A  G  E  W  W  G  E  E  K  *  K  I  A  L  S  I  S
        *  *  *  Q  G  N  G  G  G  R  R  N  E  K  L  L  F  Q  Y  H
      T  S  S  S  R  G  M  V  G  G  G  E  M  K  N  C  S  F  N  I 1150        1160       1170       1180       1190       1200
    CCACAAACATAAGAGGTAAGGTGCAGAAAGAATATGCACTTTTTTATAAACTTGATATAG
      P  Q  T  *  E  V  R  C  R  K  N  M  H  F  F  I  N  L  I  *
        H  K  H  K  R  *  G  A  E  R  I  C  T  F  L  *  T  *  Y  S
      T  T  N  I  R  G  K  V  Q  K  E  Y  A  L  F  Y  K  L  D  I 1210        1220       1230       1240       1250       1260
    CACCAATAGATAATAATAGTAATAATAGATATAGGTTGATAAGTTGTAACACCTCAGTCA
      H  Q  *  I  I  I  V  I  I  D  I  G  *  *  V  V  T  P  Q  S
        T  N  R  *  *  *  *  *  *  *  I  *  V  D  K  L  *  H  L  S  H
      A  P  I  D  N  N  S  N  N  R  Y  R  L  I  S  C  N  T  S  V 1270        1280       1290       1300       1310       1320
    TTACACAGGCCTGTCCAAAGGTATCCTTTGAGCCAATTCCCATACATTATTGTGCCCCGG
      L  H  R  P  V  Q  R  Y  P  L  S  Q  F  P  Y  I  I  V  P  R
        Y  T  G  L  S  K  G  I  L  *  A  N  S  H  T  L  L  C  P  G
      I  T  Q  A  C  P  K  V  S  F  E  P  I  P  I  H  Y  C  A  P 1330        1340       1350       1360       1370       1380
    CTGGTTTTGCGATTCTAAAGTGTAAAGATAAGAAGTTCAATGGAAAAGGACCATGTACAA
      L  V  L  R  F  *  S  V  K  I  R  S  S  M  E  K  D  H  V  Q
        W  F  C  D  S  K  V  *  R  *  E  V  Q  W  K  R  T  M  Y  K
      A  G  F  A  I  L  K  C  K  D  K  K  F  N  G  K  G  P  C  T 1390        1400       1410       1420       1430       1440
    ATGTCAGCACAGTACAATGTACACATGGAATTAGGCCAGTAGTATCAACTCAACTGCTGT
      M  S  A  Q  Y  N  V  H  M  E  L  G  Q  *  Y  Q  L  N  C  C
        C  Q  H  S  T  M  Y  T  W  N  *  A  S  S  I  N  S  T  A  V
      N  V  S  T  V  Q  C  T  H  G  I  R  P  V  V  S  T  Q  L  L 1450        1460       1470       1480       1490       1500
    TAAATGGCAGTCTAGCAGAAGAAGAGGTAGTAATTAGATCCGCCAATTTCGCGGACAATG
      *  M  A  V  *  Q  K  K  R  *  *  L  D  P  P  I  S  R  T  M
        K  W  Q  S  S  R  R  R  G  S  N  *  I  R  Q  F  R  G  Q  C
      L  N  G  S  L  A  E  E  E  V  V  I  R  S  A  N  F  A  D  N 1510        1520       1530       1540       1550       1560
    CTAAAGTCATAATAGTACAGCTGAATGAATCTGTAGAAATTAATTGTACAAGACCCAACA
      L  K  S  *  *  Y  S  *  M  N  L  *  K  L  I  V  Q  D  P  T
        *  S  H  N  S  T  A  E  *  I  C  R  N  *  L  Y  K  T  Q  Q
      A  K  V  I  I  V  Q  L  N  E  S  V  E  I  N  C  T  R  P  N 1570        1580       1590       1600       1610       1620
    ACAATACAAGAAAAAGTATACATATAGGACCAGGCAGAGCATTTTATACAACAGGAGAAA
      T  I  Q  E  K  V  Y  I  *  D  Q  A  E  H  F  I  Q  Q  E  K
        Q  Y  K  K  K  Y  T  Y  R  T  R  Q  S  I  L  Y  N  R  R  N
      N  N  T  R  K  S  I  H  I  G  P  G  R  A  F  Y  T  T  G  E
```

Figure 8D

```
          1630        1640        1650        1660        1670        1680
       TAATAGGAGATATAAGACAAGCACATTGTAACCTTAGTAGAGCAAAATGGAATGACACTT
         *  *  E  I  *  D  K  H  I  V  T  L  V  E  Q  N  G  M  T  L
          N  R  R  Y  K  T  S  T  L  *  P  *  *  S  K  M  E  *  H  F
       I  I  G  D  I  R  Q  A  H  C  N  L  S  R  A  K  W  N  D  T 1690        1700        1710        1720        1730        1740
       TAAATAAGATAGTTATAAAATTAAGAGAACAATTTGGGAATAAAACAATAGTCTTTAAGC
         *  I  R  *  L  *  N  *  E  N  N  L  G  I  K  Q  *  S  L  S
          K  *  D  S  Y  K  I  K  R  T  I  W  E  *  N  N  S  L  *  A
       L  N  K  I  V  I  K  L  R  E  Q  F  G  N  K  T  I  V  F  K 1750        1760        1770        1780        1790        1800
       ACTCCTCAGGAGGGGACCCAGAAATTGTGACGCACAGTTTTAATTGTGGAGGGGAATTTT
          T  P  Q  E  G  T  Q  K  L  *  R  T  V  L  I  V  E  G  N  F
           L  L  R  R  G  P  R  N  C  D  A  Q  F  *  L  W  R  G  I  F
       H  S  S  G  G  D  P  E  I  V  T  H  S  F  N  C  G  G  E  F 1810        1820        1830        1840        1850        1860
       TCTACTGTAATTCAACACAACTGTTTAATAGTACTTGGAATGTTACTGAAGAGTCAAATA
          S  T  V  I  Q  H  N  C  L  I  V  L  G  M  L  L  K  S  Q  I
           L  L  *  F  N  T  T  V  *  *  Y  L  E  C  Y  *  R  V  K  *
       F  Y  C  N  S  T  Q  L  F  N  S  T  W  N  V  T  E  E  S  N 1870        1880        1890        1900        1910        1920
       ACACTGTAGAAAATAACACAATCACACTCCCATGCAGAATAAAACAAATTATAAACATGT
          T  L  *  K  I  T  Q  S  H  S  H  A  E  *  N  K  L  *  T  C
            H  C  R  K  *  H  N  H  T  P  M  Q  N  K  T  N  Y  K  H  V
       N  T  V  E  N  N  T  I  T  L  P  C  R  I  K  Q  I  I  N  M 1930        1940        1950        1960        1970        1980
       GGCAGGAAGTAGGAAGAGCAATGTATGCCCCTCCCATCAGAGGACAAATTAGATGTTCAT
          G  R  K  *  E  E  Q  C  M  P  L  P  S  E  D  K  L  D  V  H
           A  G  S  R  K  S  N  V  C  P  S  H  Q  R  T  N  *  M  F  I
       W  Q  E  V  G  R  A  M  Y  A  P  P  I  R  G  Q  I  R  C  S 1990        2000        2010        2020        2030        2040
       CAAATATTACAGGGCTGCTATTAACAAGAGATGGTGGTCCTGAGGACAACAAGACCGAGG
          Q  I  L  Q  G  C  Y  *  Q  E  M  V  V  L  R  T  T  R  P  R
           K  Y  Y  R  A  A  I  N  K  R  W  W  S  *  G  Q  Q  D  R  G
       S  N  I  T  G  L  L  L  T  R  D  G  G  P  E  D  N  K  T  E 2050        2060        2070        2080        2090        2100
       TCTTCAGACCTGGAGGAGGAGATATGAGGGATAATTGGAGAAGTGAATTATATAAATATA
          S  S  D  L  E  E  E  I  *  G  I  I  G  E  V  N  Y  I  N  I
           L  Q  T  W  R  R  R  Y  E  G  *  L  E  K  *  I  I  *  I  *
       V  F  R  P  G  G  G  D  M  R  D  N  W  R  S  E  L  Y  K  Y 2110        2120        2130        2140        2150        2160
       AAGTAGTAAAAATTGAACCATTAGGAGTAGCACCCACCAAGGCAAAGAGAAGAGTGGTGC
          K  *  *  K  L  N  H  *  E  *  H  P  P  R  Q  R  E  E  W  C
           S  S  K  N  *  T  I  R  S  S  T  H  Q  G  K  E  K  S  G  A
       K  V  V  K  I  E  P  L  G  V  A  P  T  K  A  K  R  R  V  V
```

Figure 8E

```
        2170      2180      2190      2200      2210      2220
AGAGAGAAAAAAGAGCAGTGGGAATAGGAGCTGTGTTCCTTGGGTTCTTGGGAGCAGCAG
  R  E  K  K  E  Q  W  E  *  E  L  C  S  L  G  S  W  E  Q  Q
   E  R  K  K  S  S  G  N  R  S  C  V  P  W  V  L  G  S  S  R
 Q  R  E  K  R  A  V  G  I  G  A  V  F  L  G  F  L  G  A  A 2230      2240      2250      2260      2270      2280
GAAGCACTATGGGCGCAGCGGCAATGACGCTGACGGTACAGGCCAGACTATTATTGTCTG
  E  A  L  W  A  Q  R  Q  *  R  *  R  Y  R  P  D  Y  Y  C  L
   K  H  Y  G  R  S  G  N  D  A  D  G  T  G  Q  T  I  I  V
 G  S  T  M  G  A  A  A  M  T  L  T  V  Q  A  R  L  L  L  S 2290      2300      2310      2320      2330      2340
GTATAGTGCAACAGCAGAACAATCTGCTGAGGGCTATTGAGGCGCAACAGCATCTGTTGC
  V  *  C  N  S  R  T  I  C  *  G  L  L  R  R  N  S  I  C  C
   Y  S  A  T  A  E  Q  S  A  E  G  Y  *  G  A  T  A  S  V  A
 G  I  V  Q  Q  Q  N  N  L  L  R  A  I  E  A  Q  Q  H  L  L 2350      2360      2370      2380      2390      2400
AACTCACAGTCTGGGGCATCAAGCAGCTCCAGGCAAGAGTCCTGGCTGTGGAAAGATACC
  N  S  Q  S  G  A  S  S  S  S  R  Q  E  S  W  L  W  K  D  T
   T  H  S  L  G  H  Q  A  A  P  G  K  S  P  G  C  G  K  I  P
 Q  L  T  V  W  G  I  K  Q  L  Q  A  R  V  L  A  V  E  R  Y 2410      2420      2430      2440      2450      2460
TAAGGGATCAACAGCTCCTGGGGATTTGGGGTTGCTCTGGAAAACTCATCTGCACCACTG
  *  G  I  N  S  S  W  G  F  G  V  A  L  E  N  S  S  A  P  L
   K  G  S  T  A  P  G  D  L  G  L  L  W  K  T  H  L  H  H  C
 L  R  D  Q  Q  L  L  G  I  W  G  C  S  G  K  L  I  C  T  T 2470      2480      2490      2500      2510      2520
CTGTGCCTTGGAATGCTAGTTGGAGTAATAAATCTCTGAATAAGATTTGGGATAACATGA
  L  C  L  G  M  L  V  G  V  I  N  L  *  I  R  F  G  I  T  *
   C  A  L  E  C  *  L  E  *  *  I  S  E  *  D  L  G  *  H  D
 A  V  P  W  N  A  S  W  S  N  K  S  L  N  K  I  W  D  N  M 2530      2540      2550      2560      2570      2580
CCTGGATAGAGTGGGACAGAGAAATTAACAATTACACAAGCATAATATACAGCTTAATTG
  P  G  *  S  G  T  E  K  L  T  I  T  Q  A  *  Y  T  A  *  L
   L  D  R  V  G  Q  R  N  *  Q  L  H  K  H  N  I  Q  L  N  *
 T  W  I  E  W  D  R  E  I  N  N  Y  T  S  I  I  Y  S  L  I 2590      2600      2610      2620      2630      2640
AAGAATCGCAGAACCAACAAGAAAAGAATGAACAAGAATTATTAGAATTAGATAAATGGG
  K  N  R  R  T  N  K  K  R  M  N  K  N  Y  *  N  *  I  N  G
   R  I  A  E  P  T  R  K  E  *  T  R  I  I  R  I  R  *  M  G
 E  E  S  Q  N  Q  Q  E  K  N  E  Q  E  L  L  E  L  D  K  W 2650      2660      2670      2680      2690      2700
CAAGTTTGTGGAATTGGTTTGACATAACAAAATGGCTGTGGTATATAAAAATATTCATAA
  Q  V  C  G  I  G  L  T  *  Q  N  G  C  G  I  *  K  Y  S  *
   K  F  V  E  L  V  *  H  N  K  M  A  V  V  Y  K  N  I  H  N
 A  S  L  W  N  W  F  D  I  T  K  W  L  W  Y  I  K  I  F  I
```

Figure 8F

```
         2710      2720      2730      2740      2750      2760
     TGATAGTAGGAGGCTTGATAGGTTTAAGAATAGTTTTTTCTGTACTTTCTATAGTGAATA
      *  *  *  E  A  *  *  V  *  E  *  F  F  L  Y  F  L  *  *  I
       D  S  R  R  L  D  R  F  K  N  S  F  F  C  T  F  Y  S  E  *
      M  I  V  G  G  L  I  G  L  R  I  V  F  S  V  L  S  I  V  N 2770      2780      2790      2800      2810      2820
     GAGTTAGGCAGGGATACTCACCATTATCGTTTCAGACCCACCTCCCATCCTCGAGGGGAC
       E  L  G  R  D  T  H  H  Y  R  F  R  P  T  S  H  P  R  G  D
        S  *  A  G  I  L  T  I  I  V  S  D  P  P  P  I  L  E  G  T  (Rev)
      R  V  R  Q  G  Y  S  P  L  S  F  Q  T  H  L  P  S  S  R  G   (Env)

2830      2840      2850      2860      2870      2880
     CCGACAGGCCCGGAGGAATCGAAGAAGAAGGTGGAGAGAGAGACAGAGACAGATCCGGTC
       P  T  G  P  E  E  S  K  K  K  V  E  R  E  T  E  T  D  P  V
        R  Q  A  R  R  N  R  R  R  R  W  R  E  R  Q  R  Q  I  R  S
      P  D  R  P  G  G  I  E  E  E  G  G  E  R  D  R  D  R  S  G 2890      2900      2910      2920      2930      2940
     CATTAGTGAACGGATTCTTGGCGCTTATCTGGGTCGATCTGCGGAGCCTGTTCCTCTTCA
       H  *  *  T  D  S  W  R  L  S  G  S  I  C  G  A  C  S  S  S
        I  S  E  R  I  L  G  A  Y  L  G  R  S  A  E  P  V  P  L  Q
      P  L  V  N  G  F  L  A  L  I  W  V  D  L  R  S  L  F  L  F 2950      2960      2970      2980      2990      3000
     GCTACCACCGCTTGAGAGACTTACTCTTGATTGTGATGAGGATTGTGGAACTTCTGGGAC
       A  T  T  A  *  E  T  Y  S  *  L  *  *  G  L  W  N  F  W  D
        L  P  P  L  E  R  L  T  L  D  C  D  E  D  C  G  T  S  G  T
      S  Y  H  R  L  R  D  L  L  L  I  V  M  R  I  V  E  L  L  G 3010      3020      3030      3040      3050      3060
     TAGCAGGGGGGTGGGAAGTCCTCAAATATTGGTGGAATCTCCTACAGTATTGGAGTCAGG
       *  Q  G  G  G  K  S  S  N  I  G  G  I  S  Y  S  I  G  V  R
        S  R  G  V  G  S  P  Q  I  L  V  E  S  P  T  V  L  E  S  G
      L  A  G  G  W  E  V  L  K  Y  W  W  N  L  L  Q  Y  W  S  Q 3070      3080      3090      3100      3110      3120
     AACTAAAGAATAGTGCTGTTAGCTTGCTCAATGCCACAGCTGTAGCAGTAGCTGAAGGGA
       N  *  R  I  V  L  L  A  C  S  M  P  Q  L  *  Q  *  L  K  G
        T  K  E  *  C  C  *  L  A  Q  C  H  S  C  S  S  S  *  R  D
      E  L  K  N  S  A  V  S  L  L  N  A  T  A  V  A  V  A  E  G 3130      3140      3150      3160      3170      3180
     CAGATAGGGTTATAGAAGTATTACAGAGAGCTGTTAGAGCTATTCTCCACATACCTAGAA
       Q  I  G  L  *  K  Y  Y  R  E  L  L  E  L  F  S  T  Y  L  E
        R  *  G  Y  R  S  I  T  E  S  C  *  S  Y  S  P  H  T  *  K
      T  D  R  V  I  E  V  L  Q  R  A  V  R  A  I  L  H  I  P  R 3190      3200      3210      3220      3230      3240
     GAATAAGACAGGGCTTGGAAAGGGCTTTGCTATAAGATGGGTGGCAAGTGGTCAAAAAGT
       E  *  D  R  A  W  K  G  L  C  Y  K  M  G  G  K  W  S  K  S
        N  K  T  G  L  G  K  G  F  A  I  R  W  V  A  S  G  Q  K  V
      R  I  R  Q  G  L  E  R  A  L  L  *  D  G  W  Q  V  V  K  K
```

Figure 8G

```
        3250       3260       3270       3280       3290       3300
AGTATAGTCGTATGGCCTGCTGTAAGGAAAAGAATGAGAAGAACTGAGCCAGCAGCAGAT
  S  I  V  V  W  P  A  V  R  K  R  M  R  R  T  E  P  A  A  D
   V  *  S  Y  G  L  L  *  G  K  E  *  E  E  L  S  Q  Q  Q  M
 *  Y  S  R  M  A  C  C  K  E  K  N  E  K  N  *  A  S  S  R 3310       3320       3330       3340       3350       3360
GGAGTAGGAGCAGTATCTAGAGACCTGGAAAAACATGGAGCAATCACAAGTAGCAATACA
  G  V  G  A  V  S  R  D  L  E  K  H  G  A  I  T  S  S  N  T
   E  *  E  Q  Y  L  E  T  W  K  N  M  E  Q  S  Q  V  A  I  Q
 W  S  R  S  S  I  *  R  P  G  K  T  W  S  N  H  K  *  Q  Y 3370       3380       3390       3400       3410       3420
GCAGCTAACAATGCTGATTGTGCCTGGCTAGAAGCACAAGAGGATGAAGAAGTGGGTTTT
  A  A  N  N  A  D  C  A  W  L  E  A  Q  E  D  E  E  V  G  F
   Q  L  T  M  L  I  V  P  G  *  K  H  K  R  M  K  K  W  V  F
 S  S  *  Q  C  *  L  C  L  A  R  S  T  R  G  *  R  S  G  F 3430       3440       3450       3460       3470       3480
CCAGTCAGACCTCAGGTACCTTTTAAGACCAATGACTCGCAGTGCAGCTATAGATCTTAGC
  P  V  R  P  Q  V  P  L  R  P  M  T  R  S  A  A  I  D  L  S
   Q  S  D  L  R  Y  L  *  D  Q  *  L  A  V  Q  L  *  I  L  A
 S  S  Q  T  S  G  T  F  K  T  N  D  S  Q  C  S  Y  R  S  *

3490       3500       3510       3520       3530       3540
CACTTTTTTAAGAAAAAGGGGGGACTGGAAGGGCTAATTCACTCCCAAAAAAGACAAGAT
  H  F  F  K  K  K  G  G  L  E  G  L  I  H  S  Q  K  R  Q  D
   T  F  L  R  K  R  G  D  W  K  G  *  F  T  P  K  K  D  K  I
 P  L  F  *  E  K  G  G  T  G  R  A  N  S  L  P  K  K  T  R 3550       3560       3570       3580       3590       3600
ATCCTTGATTTGTGGGTCTACCACACACAAGGCTACTTCCCTGATTGGCAGAACTACACA
  I  L  D  L  W  V  Y  H  T  Q  G  Y  F  P  D  W  Q  N  Y  T
   S  L  I  C  G  S  T  T  H  K  A  T  S  L  I  G  R  T  T  H
 Y  P  *  F  V  G  L  P  H  T  R  L  L  P  *  L  A  E  L  H 3610       3620       3630       3640       3650       3660
CCAGGGCCAGGGACCAGATTTCCACTGACCTTTGGATGGTGCTTCAAGCTAGTACCAGTT
  P  G  P  G  T  R  F  P  L  T  F  G  W  C  F  K  L  V  P  V
   Q  G  Q  G  P  D  F  H  *  P  L  D  G  A  S  S  *  Y  Q  L
 T  R  A  R  D  Q  I  S  T  D  L  W  M  V  L  Q  A  S  T  S 3670       3680       3690       3700       3710       3720
GAGCCAGAGAAGGTAGAAGAGGCCAATGAAGGAGAGAACAACTGCTTGTCACACCCTATG
  E  P  E  K  V  E  E  A  N  E  G  E  N  N  C  L  S  H  P  M
   S  Q  R  R  *  K  R  P  M  K  E  R  T  T  A  C  H  T  L  *
 *  A  R  E  G  R  R  G  Q  *  R  R  E  Q  L  L  V  T  P  Y 3730       3740       3750       3760       3770       3780
AGCCTGCATGGGATGGATGACCCGGAGAAAGAAGTGTTAGCATGGAAGTTTGACAGCAGC
  S  L  H  G  M  D  D  P  E  K  E  V  L  A  W  K  F  D  S  S
   A  C  M  G  W  M  T  R  R  K  K  C  *  H  G  S  L  T  A  A
 E  P  A  W  D  G  *  P  G  E  R  S  V  S  M  E  V  *  Q  Q
```

Figure 8H

```
        3790         3800
CTAGCATTCCATCACGTGGCCCGAGAA
  L   A   F   H   H   V   A   R   E
    *   H   S   I   T   W   P   E
  P   S   I   P   S   R   G   P   R
```

MOLECULAR CLONES OF HIV-1 VIRAL STRAINS MH-ST1 AND BA-L, AND USES THEREOF

This is a divisional of application Ser. No. 08/022,835 filed Feb. 25, 1993, now U.S. Pat. No. 5,420,030 which is a continuation of application Ser. No. 07/599,491, filed Oct. 17, 1990, now abandoned.

BACKGROUND OF THE INVENTION

HIV-1 has been identified as the etiologic agent of the acquired immunodeficiency syndrome (AIDS) (Barre-Sinoussi et al., Science 220, 868–871, 1983; Popovic et al, Science 224, 497–500, 1984; Gallo et al., Science 224, 500–503, 1984). Infected individuals generally develop antibodies to the virus within several months of exposure (Sarngadharan et al., Science 224, 506–508, 1984), which has made possible the development of immunologically based tests which can identify most of blood samples from infected individuals. This is a great advantage in diagnosis, and is vital to maintaining the maximum possible safety of samples from blood banks.

An important aspect of HIV-1 is its genetic variability (Hahn et al., Proc. Natl. Acad. Sci. U.S.A. 82, 4813–4817, 1985). This is particularly evident in the gene for the outer envelope glycoprotein (Starcich et al., Cell 45, 637–648, 1986; Alizon et al., Cell 46, 63–74, 1986; Gurgo et al., Virology 164, 531–536, 1988). Since the outer envelope glycoprotein is on the surface of the virus particle and the infected cell, it is potentially one of the primary targets of the immune system, including the target of neutralizing antibodies and cytotoxic T cells. This variability may also lead to differences in the ability of antigens from different strains of HIV-1 to be recognized by antibodies from a given individual, as well as to differences in the ability of proteins from different strains of virus to elicit an immune response which would be protective against the mixture of virus strains that exists in the at risk populations.

Several biologically active complete molecular clones of various strains of HIV-1 have been obtained and sequenced. These clones, however, seem to represent viral genotypes which are relatively atypical of United States HIV-1 isolates. In addition, several of the translational reading frames for non-structural viral proteins are not complete. Further, viruses derived from these clones do not grow in macrophages, in contrast to many HIV-1 field isolates and, perhaps, because of this lack of ability to infect macrophage efficiently, these clones do not replicate well in chimpanzees. This latter ability is important for testing candidate vaccines in animal systems. In addition, the ability to infect macrophages is critical in evaluating the possible protective efficacy of an elicited immune response since neutralization of infectivity on macrophages may differ from the better studied neutralization on T cells.

Neutralizing antibodies (Robert-Guroff et al., Nature 316, 72–74, 1985; Weiss et al., Nature 316, 69–72, 1985) have been demonstrated in infected individuals, as have cytotoxic T cell responses (Walker et al, Nature 328, 345–348, 1988). Although these do not appear to be protective, it is likely that if they were present prior to infection, they would prevent infection, especially by related strains of virus. This is supported by the finding that macaques can be protected by immunization with inactivated simian immunodeficiency virus (SIV) from infection with the homologous live virus (Murphy-Corb et al., Science 246, 1293–1297, 1989). Chimps also have been passively protected against challenge by live virus by prior administration of neutralizing antibodies to the same virus (Emini et al., J. Virol. 64, 3674–3678, 1989). One problem, however, is that at least some of the neutralizing antibodies studied depend on recognition of a variable region on the envelope (Matsushita et al., J. Virol. 62, 2107–2114, 1988; Rusche et al., Proc. Natl. Acad. Sci. U.S.A. 85, 3198–3202, 1988; Skinner et al., AIDS Res. Hum. Retroviruses 4, 187–197, 1988) called the V3 region (Starcich et al., Cell 45, 637–648, 1986).

An at least partial solution to the problem of viral heterogeneity is to identify prototypical HIV-1 strains, that is, those that are most similar by DNA sequence data or serologic reactivity to strains present in the population at risk. The inclusion of a limited number of such prototype strains in a polyvalent vaccine cocktail might then result in elicitation of an immune response protective against most naturally occurring viruses within a given population. Such a mixture should also provide the maximum possible sensitivity in diagnostic tests for antibodies in infected individuals.

Components of highly representative isolates of a geographical area provide the maximum possible sensitivity in diagnostic tests and vaccines. Production of viral proteins from molecular clones by recombinant DNA techniques is the preferred and safest means to provide such proteins. Molecular clones of prototype HIV-1 strains can serve as the material from which such recombinant proteins can be made. The use of recombinant DNA avoids any possibility of the presence of live virus and affords the opportunity of genetically modifying viral gene products. The use of biological active clones ensures that the gene products are functional and hence, maximizes their potential relevance.

Infectious clones, that is, those which after transfection into recipient cells produce complete virus, are desirable for several reasons. One reason is that the gene products are by definition functional; this maximizes their potential relevance to what is occurring in vivo. A second reason is that genetically altered complete virus is easy to obtain. Consequently, the biological consequences of variability can be easily assessed. For example, the effect of changes in the envelope gene on the ability of the virus to be neutralized by antibody can be easily addressed. Using this technique, a single point mutation in the envelope gene has been shown to confer resistance to neutralizing antibody (Reitz et al., Cell 54, 57–63, 1988). A third reason is that a clonal virus population provides the greatest possible definition for challenge virus in animals receiving candidate vaccines, especially those including components of the same molecularly cloned virus.

SUMMARY OF THE INVENTION

It is an object of the present invention to provide vaccine components for an anti HIV-1 vaccine which would represent a typical United States isolate HIV-1.

It is another object of the present invention to provide diagnostic tests for the detection of HIV-1.

Various other objects and advantages of the present invention will become apparent from the drawings and the following description of the invention.

BRIEF DESCRIPTION OF THE DRAWINGS

FIG. 1 shows the structure and restriction map of the lambda MN-PH1 clone.

FIGS. 2A–2H shows the DNA sequence representing the MN-PH1 genome (SEQ ID NO:1).

FIGS. 3A–3C shows the predicted amino acid sequence of the MN-PH1 envelope (env) protein (SEQ ID NO:2).

FIGS. 6A–6S shows the DNA sequence representing the MN-ST1 genome (SEQ ID NO:3) and the predicted amino acid sequence of the MN-ST1 genome and env protein (SEQ ID NO:4).

FIGS. 8A–8H shows the DNA sequence of the env gene of BA-L (SEQ ID NO:5).

FIGS. 9A–9C shows the predicted amino acid sequence of the BA-L env protein (SEQ ID NO:6).

DETAILED DISCLOSURE OF THE INVENTION

Figure 1:
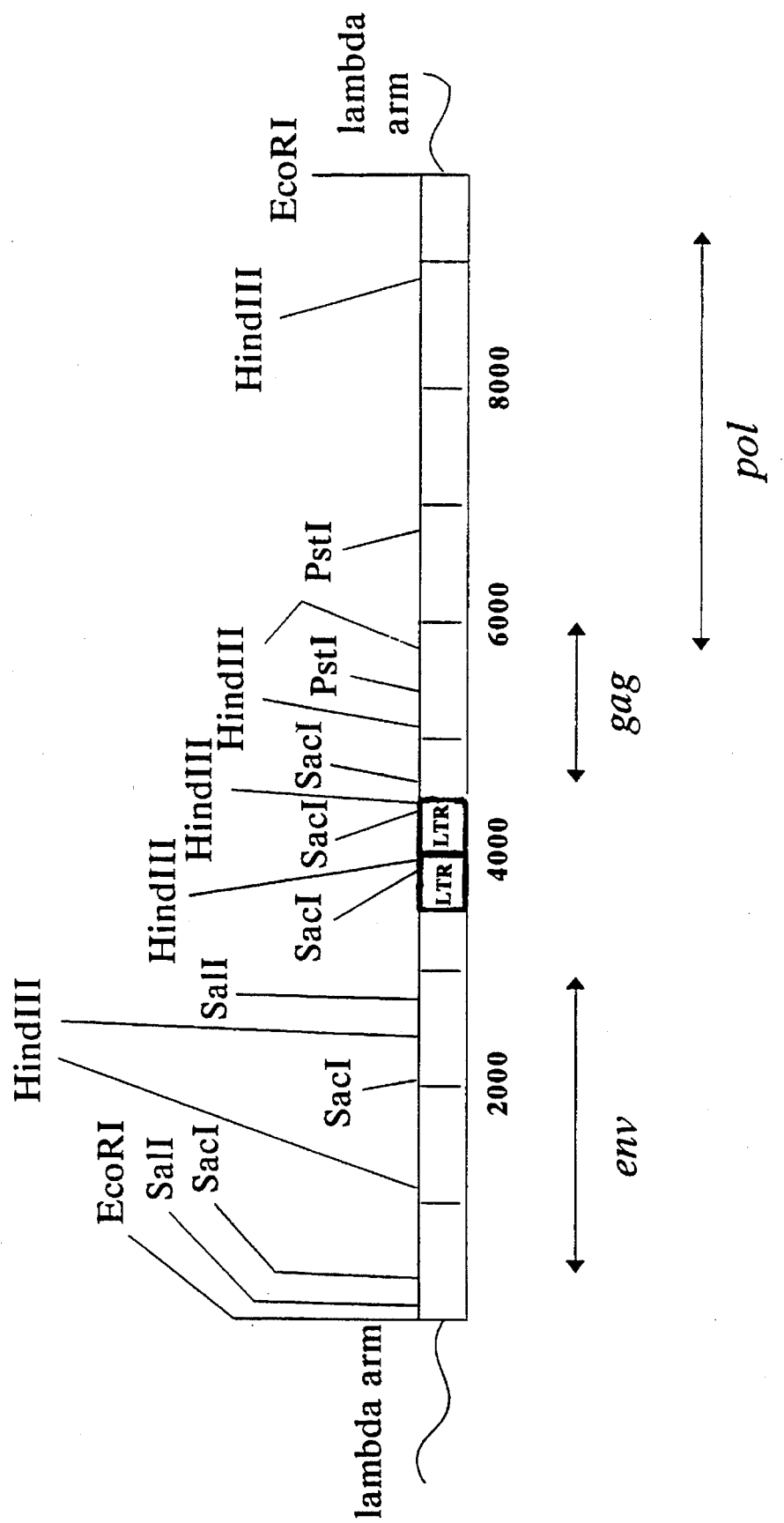

The present invention relates to the HIV-1 virus strains, MN-ST1 and BA-L, which are more typical of the HIV-1 isolates found in the United States than previously known HIV-1 strains. Local isolates provide better material for vaccine and for the detection of the virus in biological samples, such as blood bank samples.

The present invention relates to DNA segments encoding the env protein of MN-ST1 or BA-L (the DNA sequence given in FIGS. 6A–6S and FIGS. 8A–8H, and shown in SEQ ID NO:3 and SEQ ID NO:5, respectively being two such examples) and to nucleotide sequences complementary to the segments referenced above as well as to other genes and nucleotide sequences contained in these clones. The present invention also relates to DNA segments encoding a unique portion of the MN-ST1 env protein or the BA-L env protein. (A "unique portion" consists of to at least five (or six) amino acids or corresponding to at least 15 (or 18) nucleotides.)

The invention further relates to the HIV-1virus strains MN-ST1 and BA-L themselves. The HIV-1 virus strains of the present invention are biologically active and can easily be isolated by one skilled in the art using known methodologies.

The above-described DNA segments of the present invention can be placed in DNA constructs which are then used in the transformation of host cells for generation of recombinantly produced viral proteins. DNA constructs of the present invention comprise a DNA segment encoding the env protein and the flanking region of MN-ST1 (or BA-L) or a portion thereof and a vector. The constructs can further comprise a second DNA segment encoding both a rev protein and a rev-responsive region of the env gene operably linked to the first DNA segment encoding the env protein. The rev protein facilitates efficient expression of the env protein in eucaryotic cells. Suitable vectors for use in the present invention include, but are not limited to, pSP72, lambda EMBL3 and SP65gpt.

Host cells to which the present invention relates are stably transformed with the above-described DNA constructs. The cells are transformed under conditions such that the viral protein encoded in the transforming construct is expressed. The host cell can be procaryotic (such as bacterial), lower eucaryotic (such as fungal, including yeast) or higher eucaryotic (such as mammalian). The host cells can be used to generate recombinantly produced MN-ST1 (or BA-L) env protein by culturing the cells in a manner allowing expression of the viral protein encoded in the construct. The recombinantly produced protein is easily isolated from the host cells using standard protein isolation protocols.

Since HIV-1 strains MN-ST1 and BA-L represent relatively typical United States genotypes, non-infectious MN-ST1 or BA-L proteins (for example, the env protein), peptides or unique portions of MN-ST1 or BA-L proteins (for example, a unique portion of the env protein), and even whole inactivated MN-ST1 or BA-L can be used as an immunogen in mammals, such as primates, to generate antibodies capable of neutralization and T cells capable of killing infected cells. The protein can be isolated from the virus or made recombinantly from a cloned envelope gene. Accordingly, the virus and viral proteins of the present invention are of value as either a vaccine or a component thereof, or an agent in immunotherapeutic treatment of individuals already infected with HIV-1.

As is customary for vaccines, a non-infectious antigenic portion of MN-ST1 or BA-L, for example, the env protein, can be delivered to a mammal in a pharmacologically acceptable carrier. The present invention relates to vaccines comprising non-infectious antigenic portions of either MN-ST1 or BA-L and vaccines comprising non-infectious antigenic portions of both MN-ST1 and BA-L. Vaccines of the present invention can include effective amounts of immunological adjuvants known to enhance an immune response. The viral protein or polypeptide is present in the vaccine in an amount sufficient to induce an immune response against the antigenic protein and thus to protect against HIV-1 infection. Protective antibodies are usually best elicited by a series of 2–3 doses given about 2 to 3 weeks apart. The series can be repeated when circulating antibody concentration in the patient drops.

Virus derived from the infectious HIV-1(MN) clones, MN-ST1, may also be used for reproducible challenge experiments in chimpanzees treated with candidate HIV-1 vaccines or in vitro with human antiserum from individuals treated with candidate vaccines. A candidate vaccine can be administered to a test mammal, such as a chimpanzee prior to or simultaneously with the infectious MN-ST1 virus of the present invention. Effectiveness of the vaccine can be determined by detecting the presence or absence of HIV-1 infection in the test mammals. Side-by-side comparative tests can be run by further administering to a second set of test mammals the virus alone and comparing the number of infections which develop in the two sets of test mammals. Alternatively, candidate vaccines can be evaluated in humans by administering the vaccine to a patient and then testing the ability of the MN-ST1 virus to infect blood cells from the patient.

The present invention also relates to the detection of HIV-1 virus in a biological sample. For detection of an HIV-1 infection the presence of the virus, proteins encoded in the viral genome, or antibodies to HIV-1 is determined. Many types of tests, as one skilled in the art will recognize, can be used for detection. Such tests include, but are not limited to, ELISA and RIA.

In one bioassay of the present invention all, or a unique portion, of the env protein is coated on a surface and contacted with the biological sample. The presence of a resulting complex formed between the protein and antibodies specific therefor in the serum can be detected by any of the known methods commonly used in the art, such as, for example, fluorescent antibody spectroscopy or colorimetry.

The following non-limiting examples are given to further demonstrate the present invention without being deemed limitative thereof.

EXAMPLES

MN-PH1 Clone

Figure 3A:
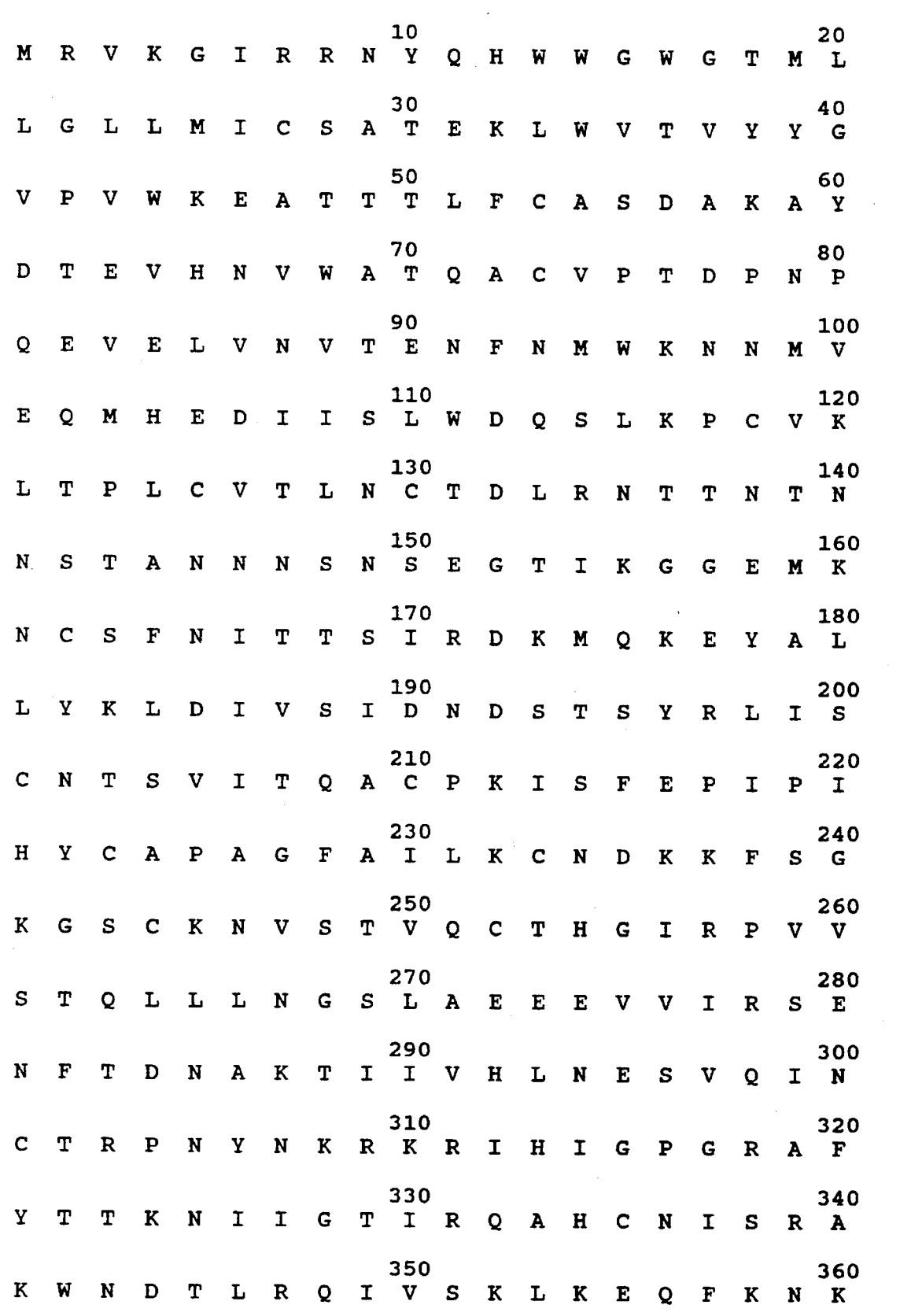
Figure 3B:
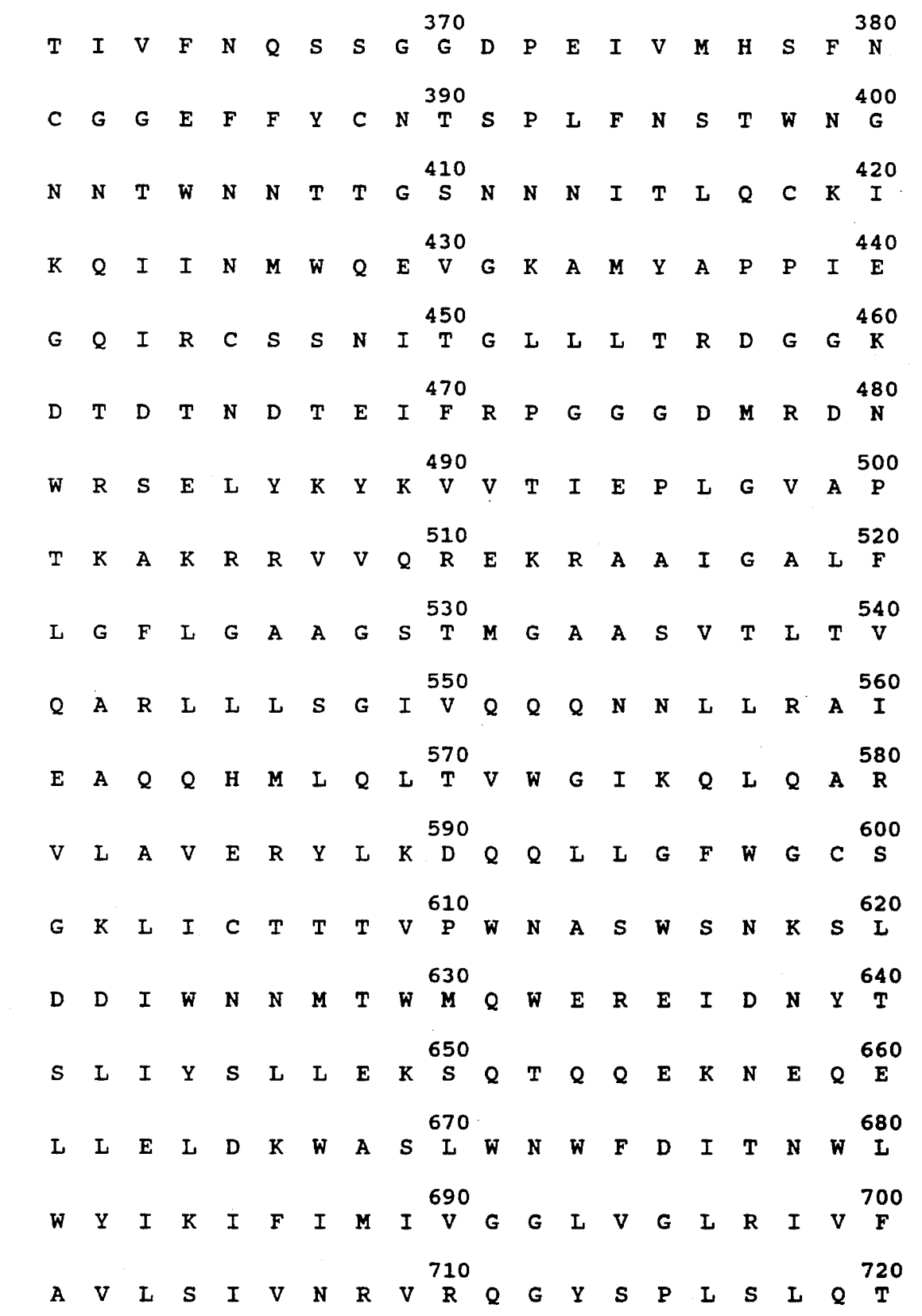
Figure 3C:
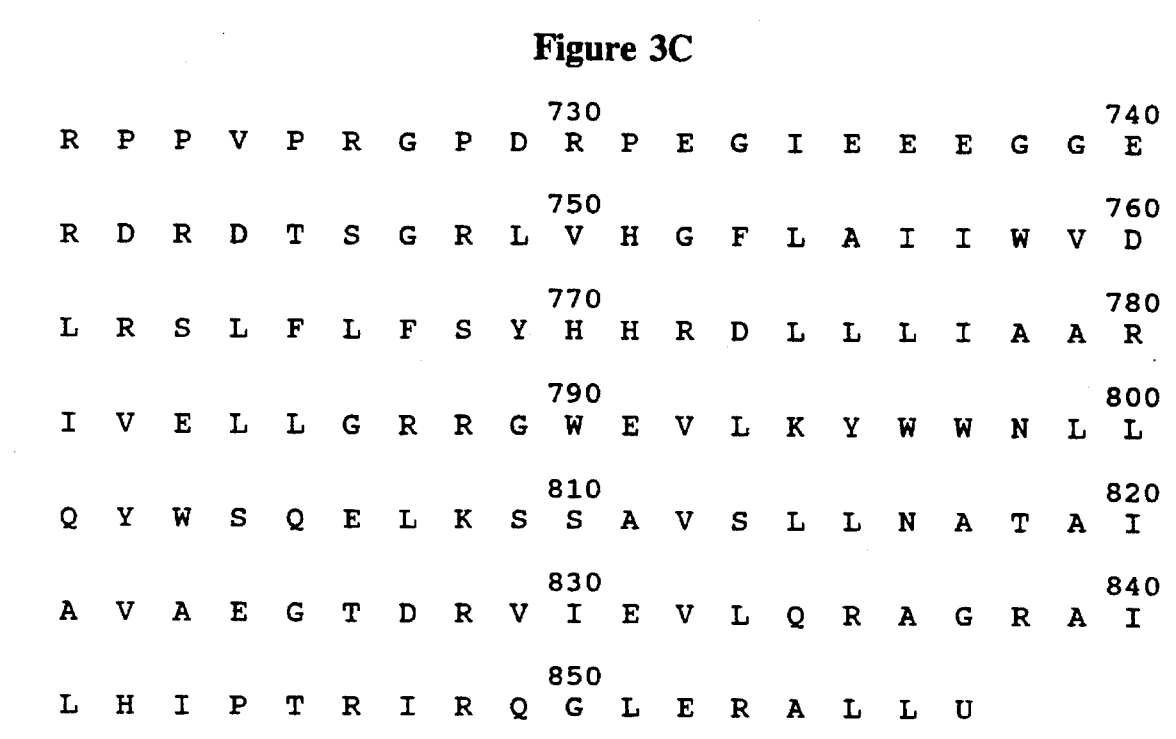
Figure 4:
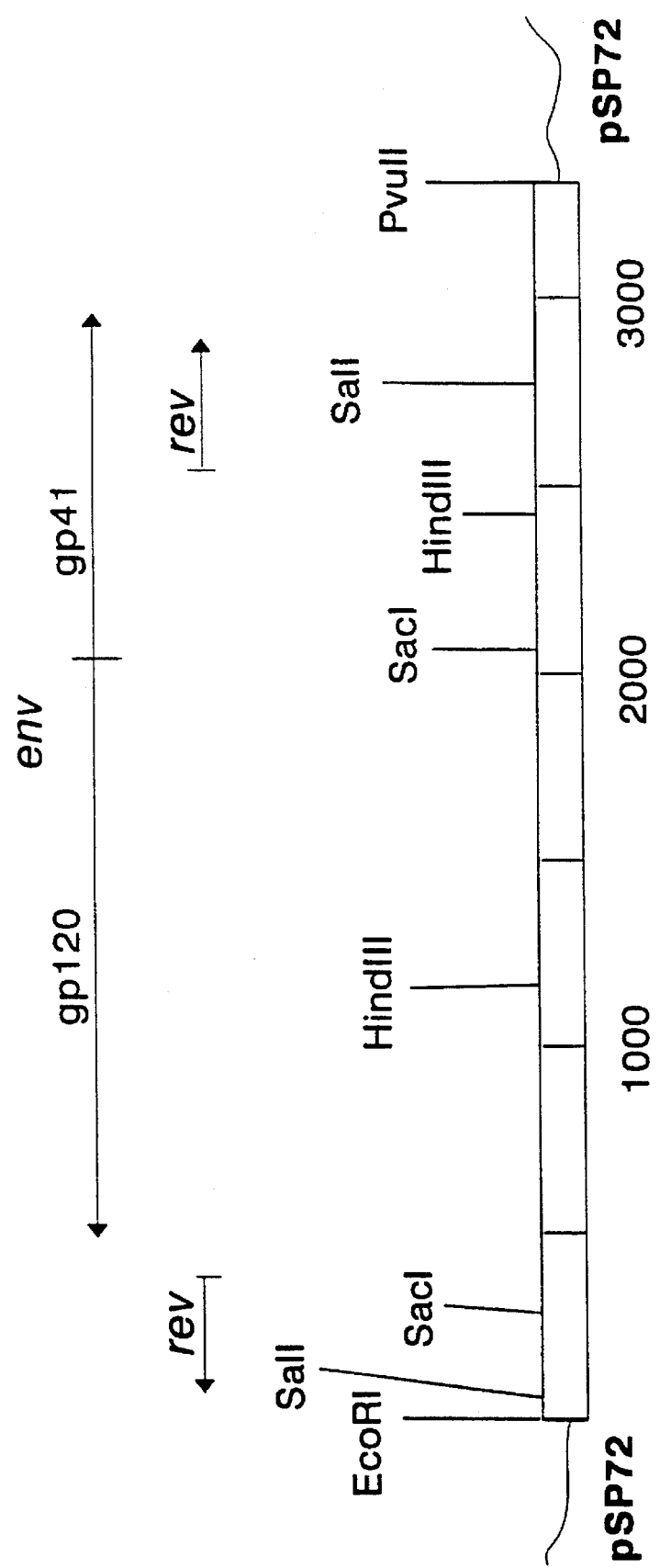
FIG. 4 shows the restriction map of the MN-PH1 envelope plasmid clone.

The permuted circular unintegrated viral DNA representing the complete HIV-1(MN) genome was cloned by standard techniques (Sambrook et al., 1989, Molecular Cloning. Cold Spring Harbor, N.Y.: Cold Spring Harbor Laboratory Press) into the Eco RI site of lambda gtWES.lambda B DNA from total DNA of H9 cells producing HIV-1(MN). This clone is designated lambda MN-PH1, and its structure and restriction map are shown in FIG. 1. The clone was subcloned into M13mp18 and M13mp19, and the DNA sequence of the entire clone, given in FIGS. 2A–2H, and as shown in SEQ ID NO:1, was obtained by the dideoxy chain termination method (Sanger et al., Proc. Natl. Acad. Sci. U.S.A. 74, 5463–5467, 1977). The amino acid sequence of the envelope protein (see FIGS. 3A–3C, and as shown in SEQ ID NO:2) was inferred from the DNA sequence. A restriction map of the cloned unintegrated viral DNA (see FIG. 1) was also obtained from the DNA sequence of lambda PH1 and used in conjunction with the inferred amino acid sequence of the vital proteins to subclone the envelope (env) gene into the commercially available plasmid pSP72 (Promega Biological Research Products, Madison, Wis.), as shown in FIG. 4. This plasmid (pMN-PH1env) contains, in addition to the coding regions for the envelope proteins, the coding region for the rev protein (Feinberg et al., Cell 46, 807–817, 1986) and the portion of the env gene which contains the rex-responsive region (Dayton et al., J. Acquir. Immune. Defic. Syndr. 1, 441–452, 1988), since both are necessary for efficient expression of the envelope protein in eucaryotic cells. This plasmid thus contains all the elements required for production of envelope protein following placement into appropriate expression vectors and introduction into recipient cells, all by standard techniques known to molecular biologists.

MN-ST1 Clone

Figure 5:
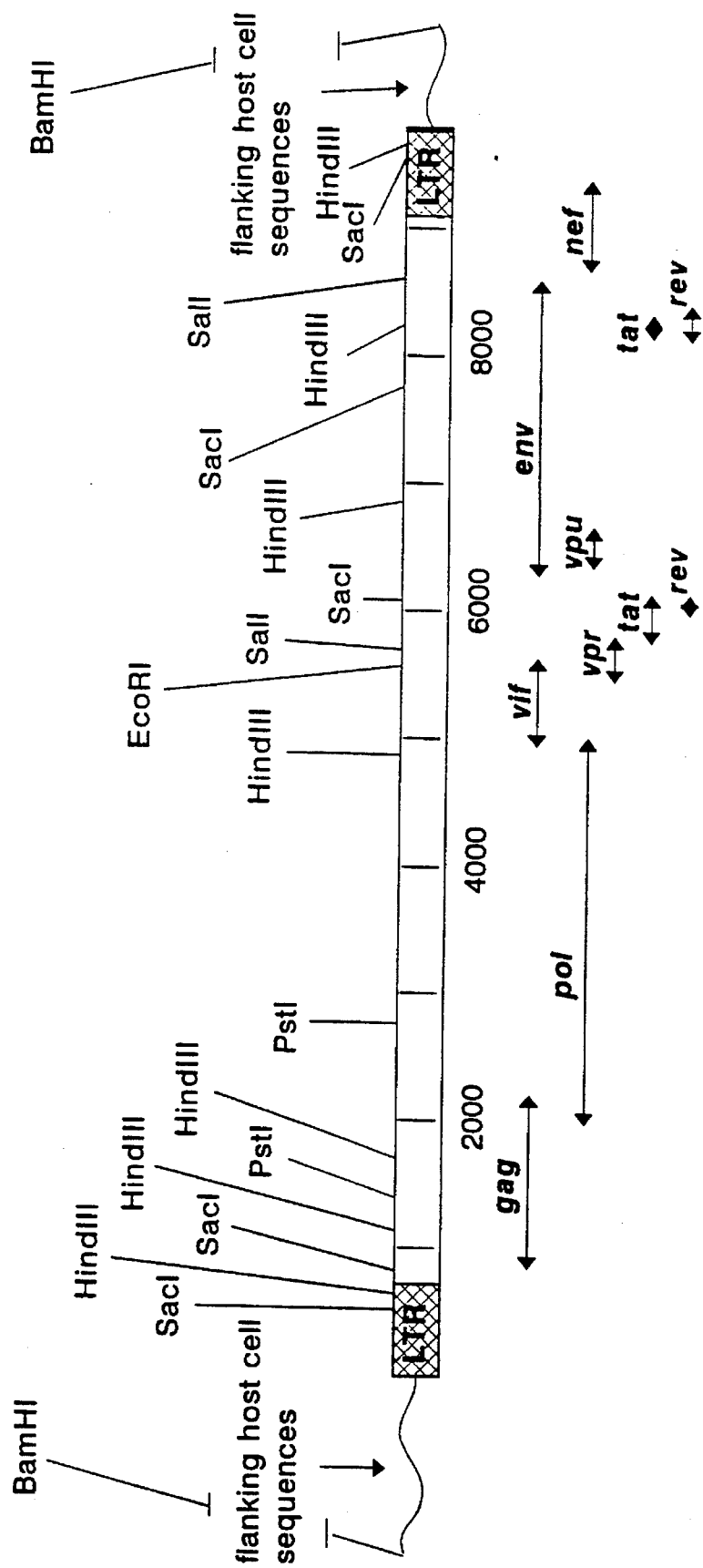
FIG. 5 shows the restriction map and structure of the lambda MN-ST1 clone.

The infectious molecular clone, lambda MN-ST1, was obtained by cloning integrated provirus from DNA purified from peripheral blood lymphocytes infected with HIV-1(MN) and maintained in culture for a short time (one month). The integrated proviral DNA was partially digested with the restriction enzyme Sau3A under conditions which gave a maximum yield of DNA fragments of from 15–20 kilobases (kb). This was cloned into the compatible BamHI site of lambda EMBL3, as shown in FIG. 5. FIG. 5 also shows the restriction map of clone lambda MN-ST1. The DNA sequence of the entire clone, given in FIGS. 6A–6S, and shown in SEQ ID NO:3, was obtained by the dideoxy chain termination method (Sanger et al., Proc. Natl. Acad. Sci. U.S.A. 74, 5463–5467, 1977). The amino acid sequence was predicted from the DNA sequence (see FIGS. 6A–6S, and SEQ ID NO:4). This clone can be transfected into recipient cells by standard techniques. After transfection, the cloned proviral DNA is expressed into biologically active virus particles, which can be used as a source for virus stocks. The proviral DNA whose restriction map is shown in FIG. 4, was removed from the lambda phage vector by digestion with BamHI and inserted into a plasmid, SP65gpt (Feinberg et al., Cell 46, 807–817, 1986). This plasmid, pMN-ST1, contains an SV40 origin of replication. Consequently, transfection into COS-1 cells (Gluzman, Y. Cell 23, 175–182, 1981), which produce a SV40 gene product which interacts with the cognate origin of replication, results in a transient high plasmid copy number with a concomitant production of a large amount of replication competent, infectious virus (Feinberg et al., Cell 46, 807–817, 1986). This provides a convenient source of genetically homogeneous virus, as well as a way to introduce desired mutations using standard methods.

The envelope gene was excised from the lambda phage clone and cloned into plasmid as described above for lambda MN-PH1. This clone (pMN-ST1env), is similar to pMN-PH1env, described above, except that it derives from a biologically active cloned provirus. Like pMN-PH1env, it can be placed in a suitable vector and host to produce the envelope protein of HIV-1(MN) by well known techniques.

BA-L Clone

Figure 7:
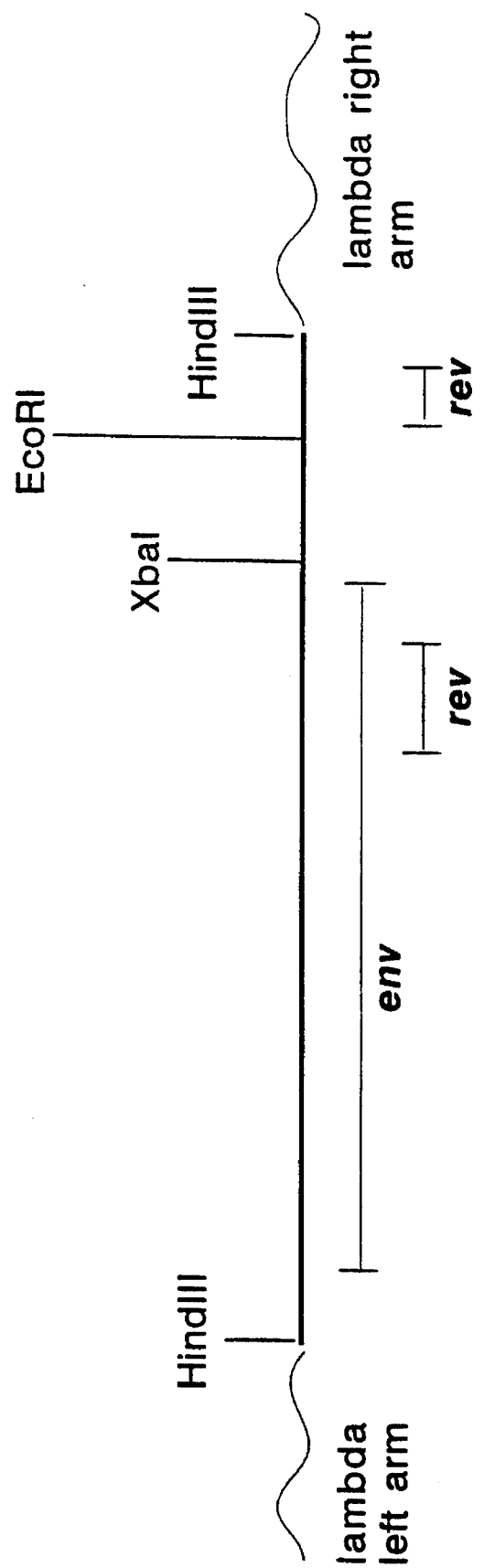
FIG. 7 shows the structure of the lambda BA-L clone.
Figure 10A:
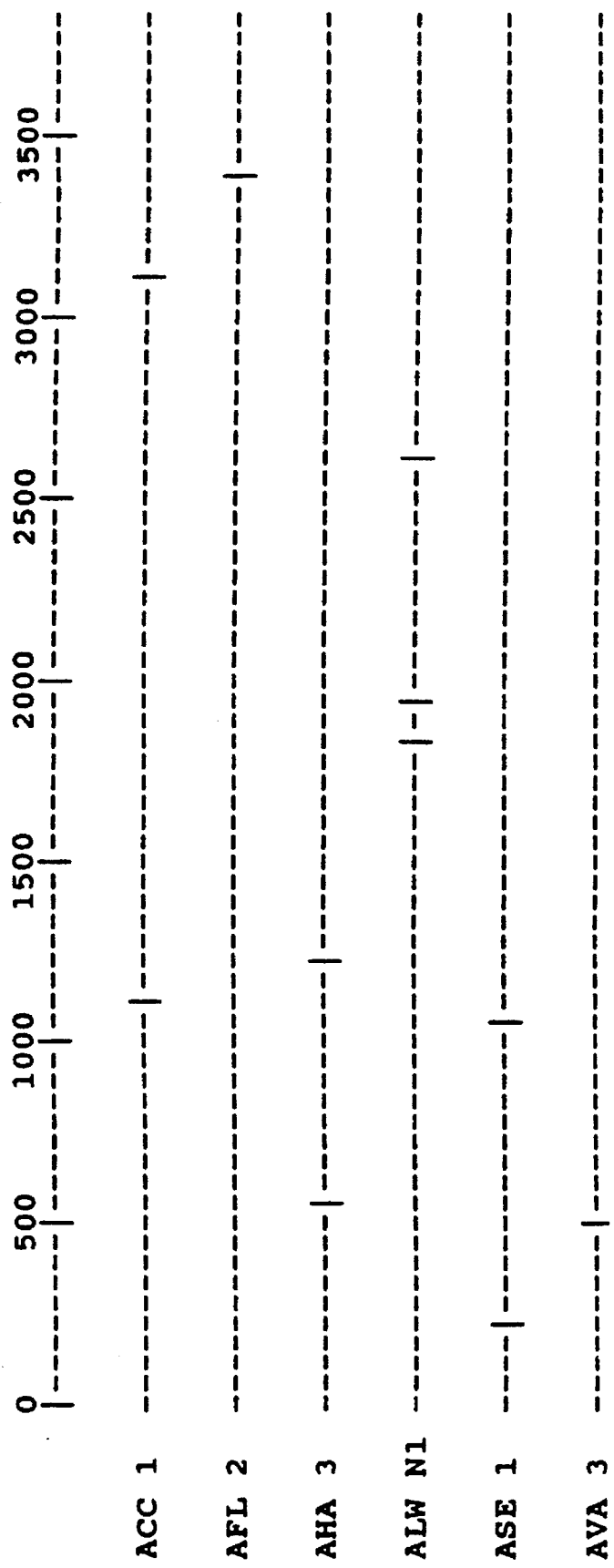
FIGS. 10A–10I shows the restriction map of the clone BA-L1.
Figure 10B:
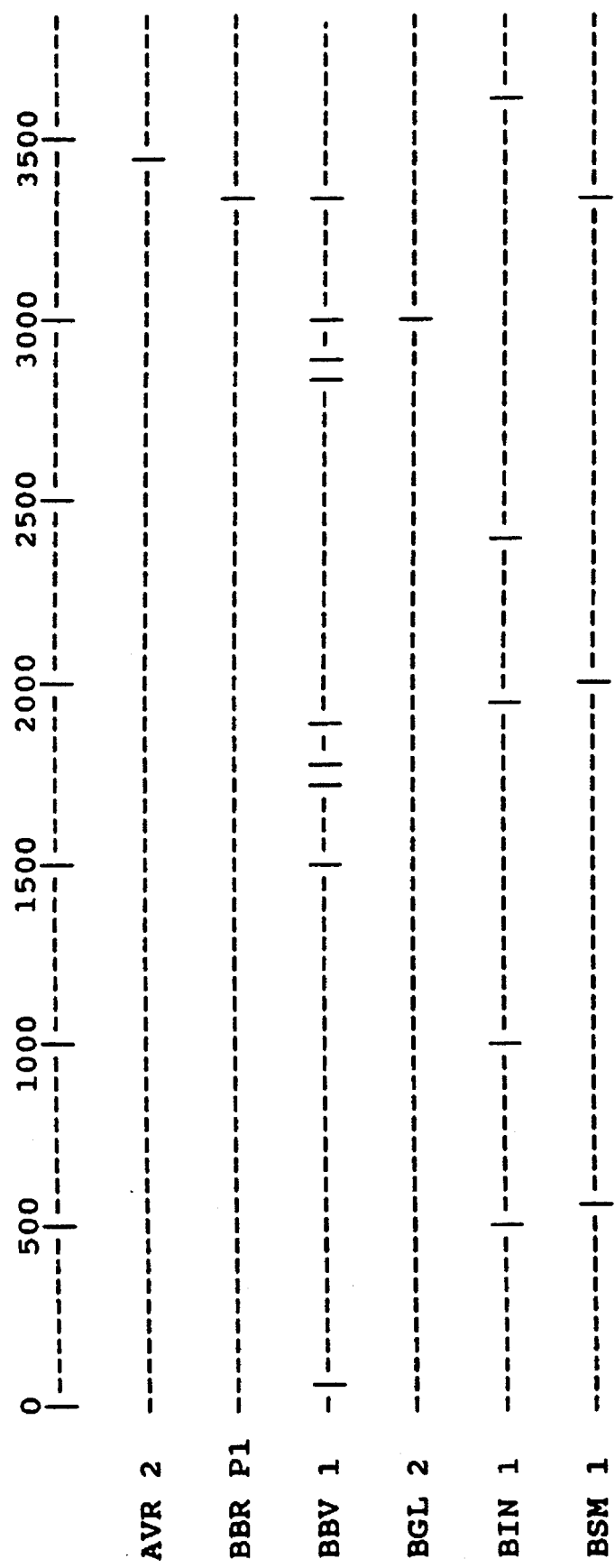
Figure 10C:
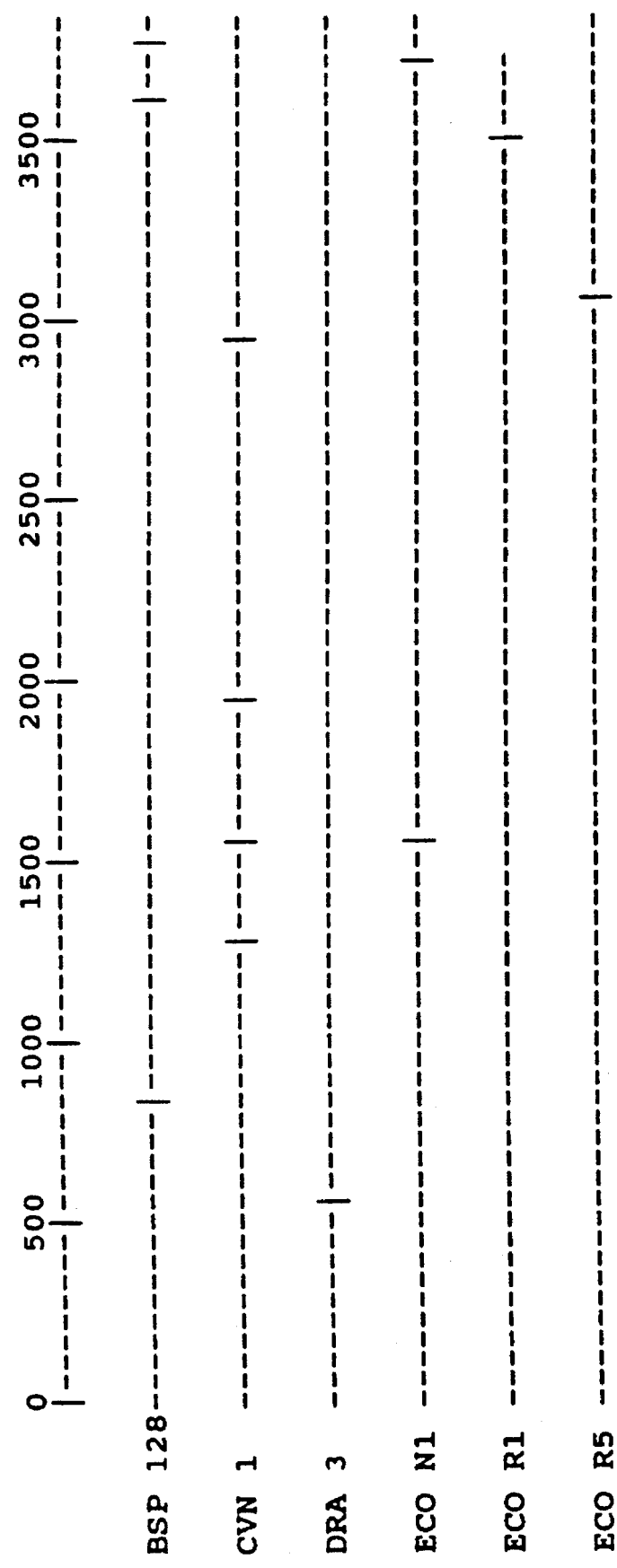
Figure 10D:
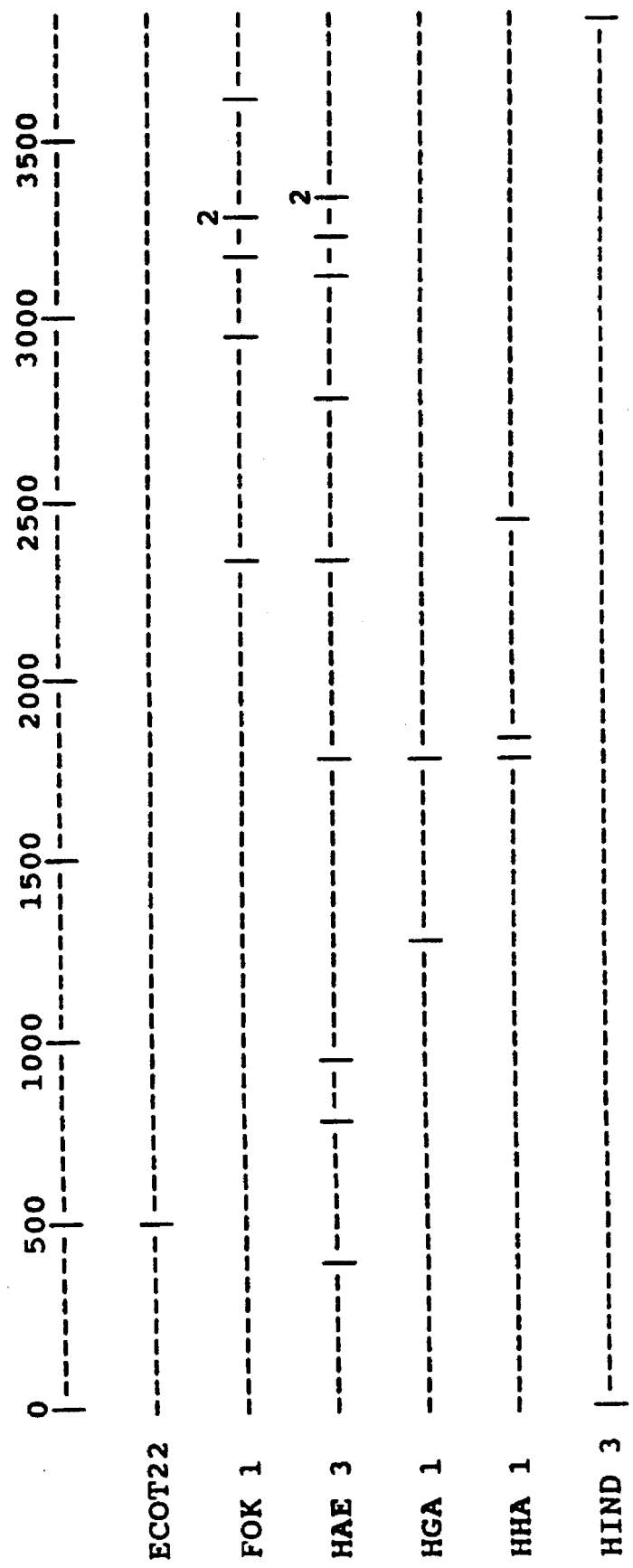
Figure 10E:
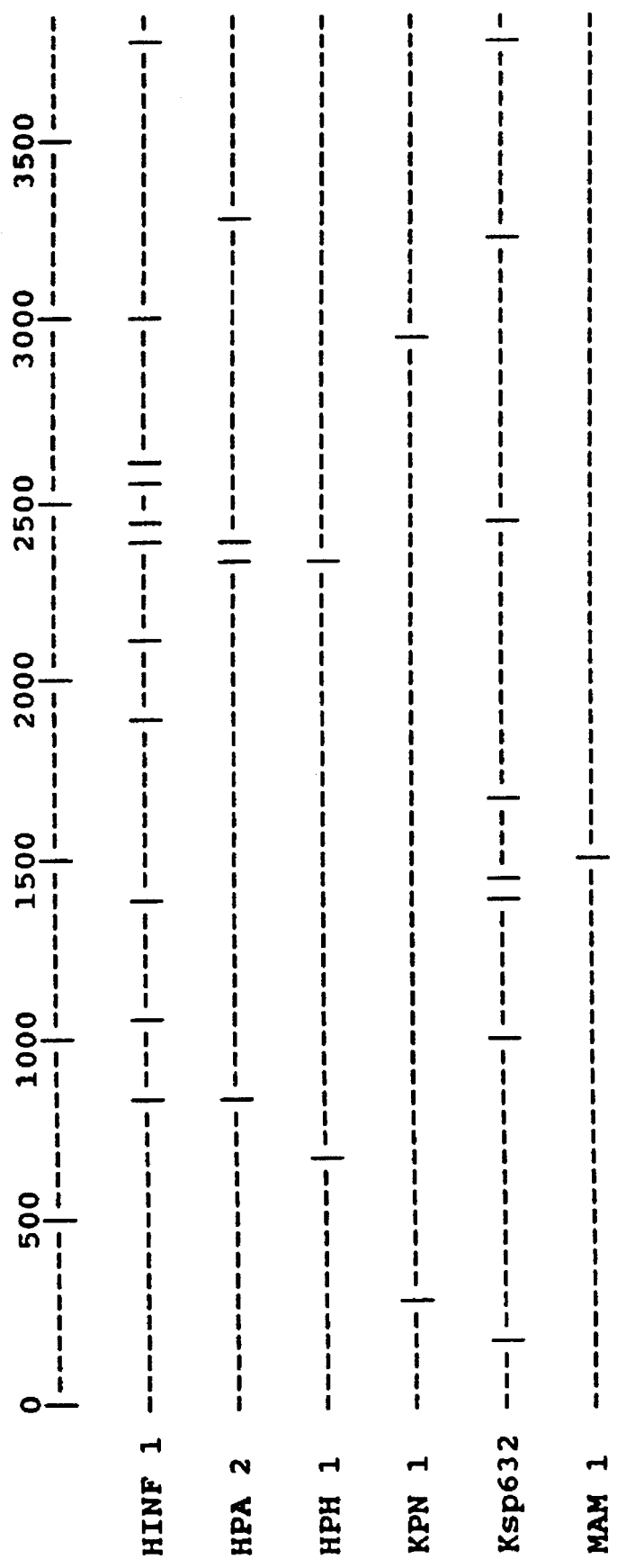
Figure 10F:
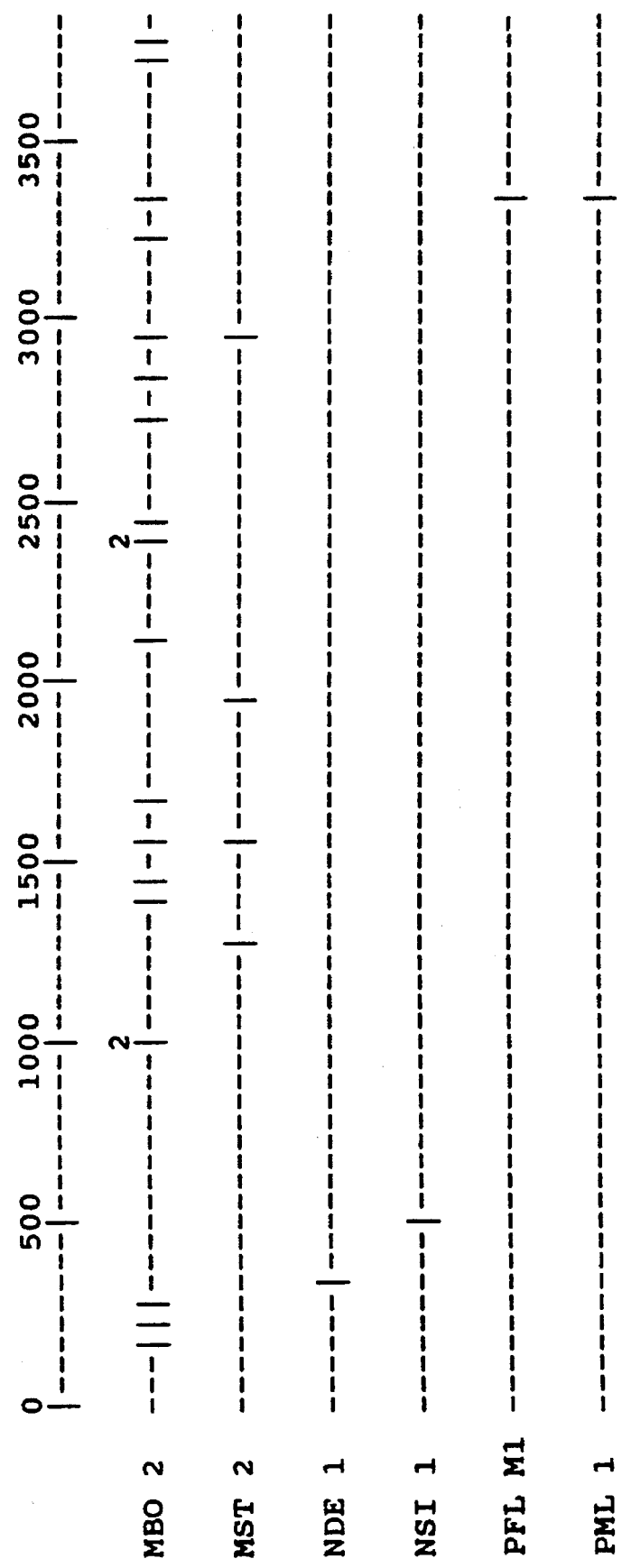
Figure 10G:
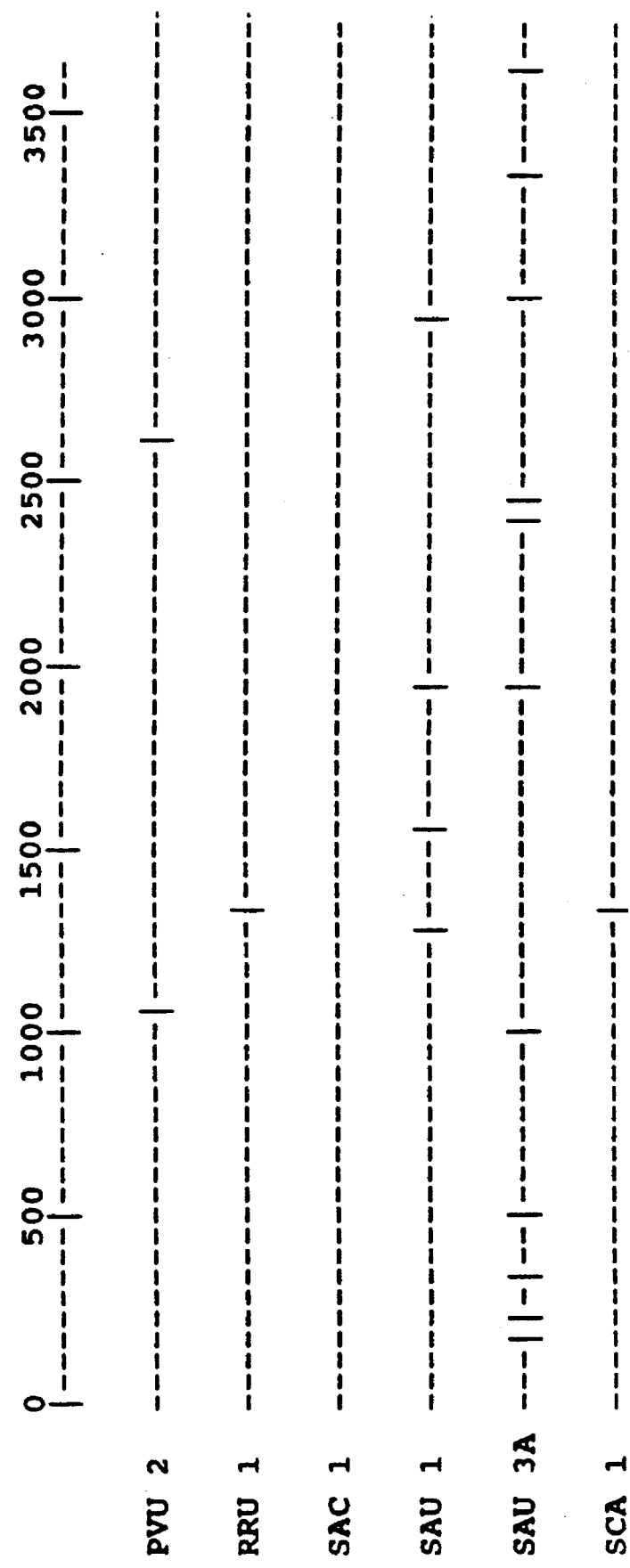
Figure 10H:
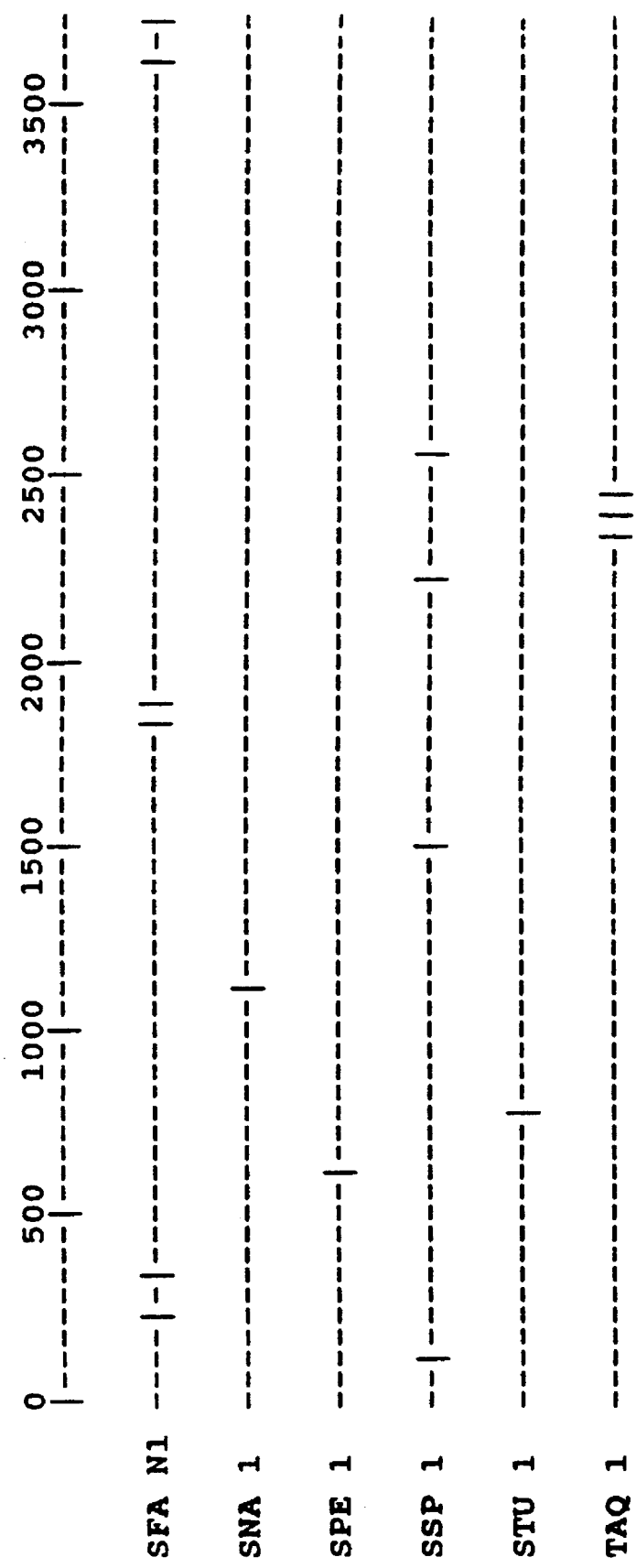
Figure 10I:
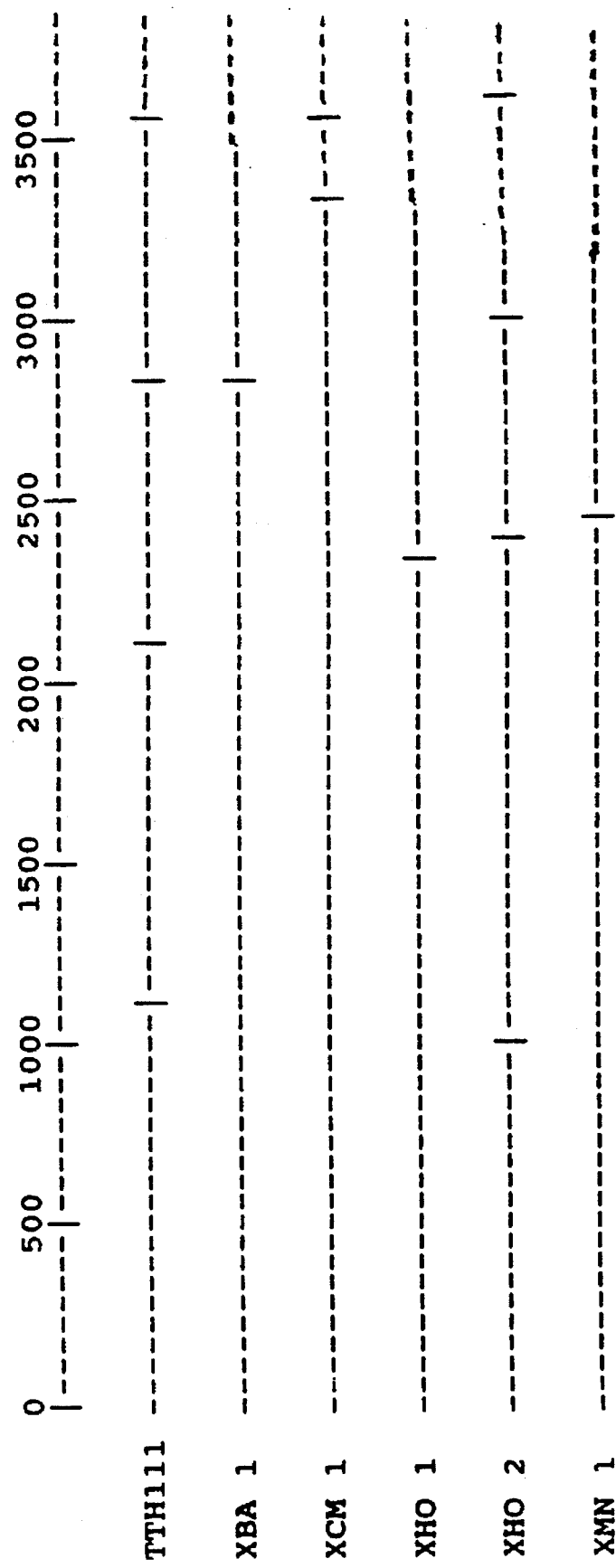

A Hind III fragment of unintegrated viral DNA representing the HIV-1(BA-L) genome was cloned by standard techniques into lambda phage Charon 28 DNA from total DNA of peripheral blood macrophages infected with and producing HIV-1(BA-L). A positive clone was selected by hybridization using a radiolabelled probe for the HIV-1 envelope. This clone, designated lambda BA-L1, was found to contain the entire gene for the envelope protein. Its structure is given in FIG. 7. The insert was transferred into a plasmid (pBluescript, Stratagene, LaJolle, Calif.) and the DNA sequence of the env gene was determined (see FIGS. 8A–8H). This clone is designated pBA-L1.

Figure 9A:
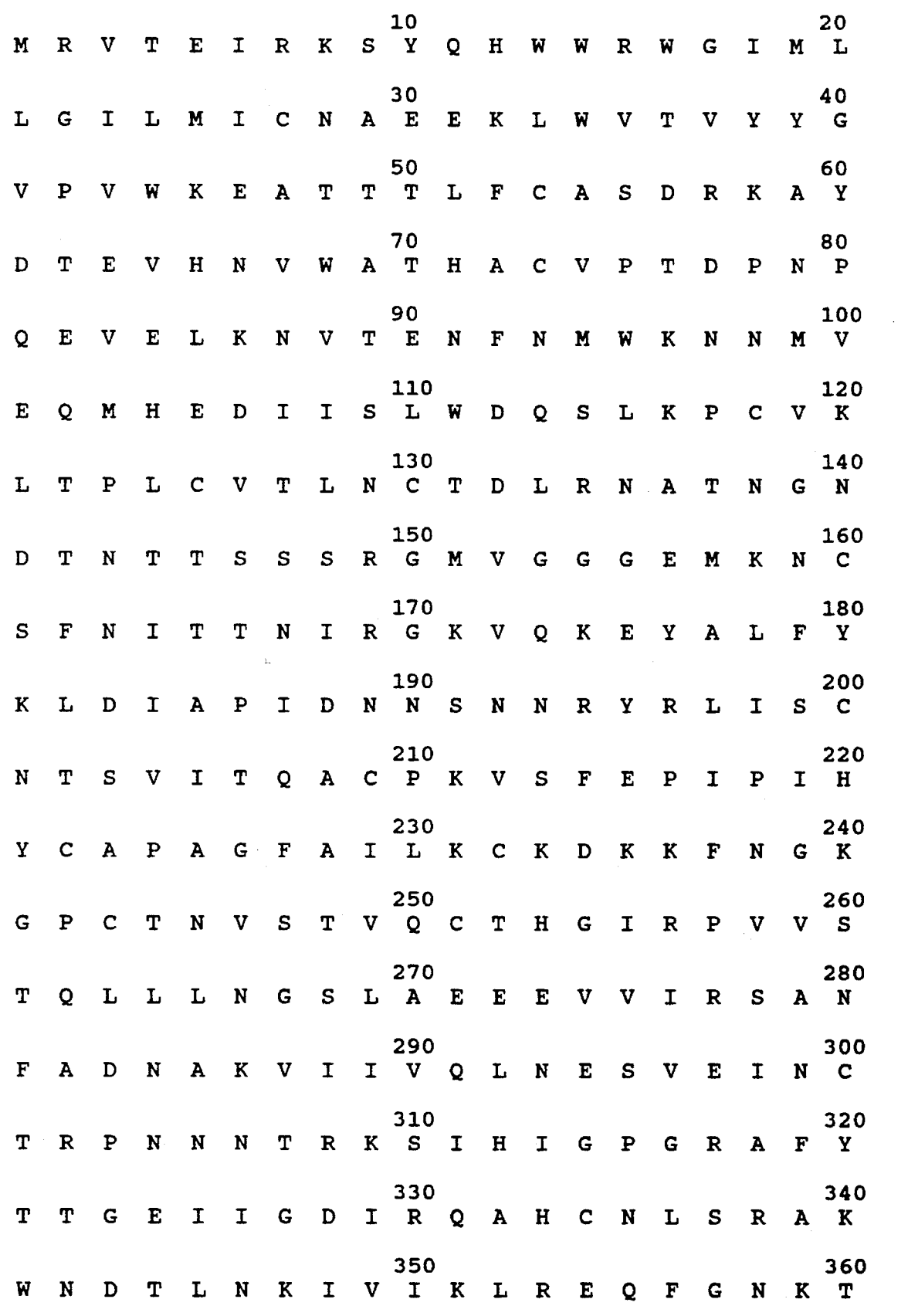
Figure 9B:
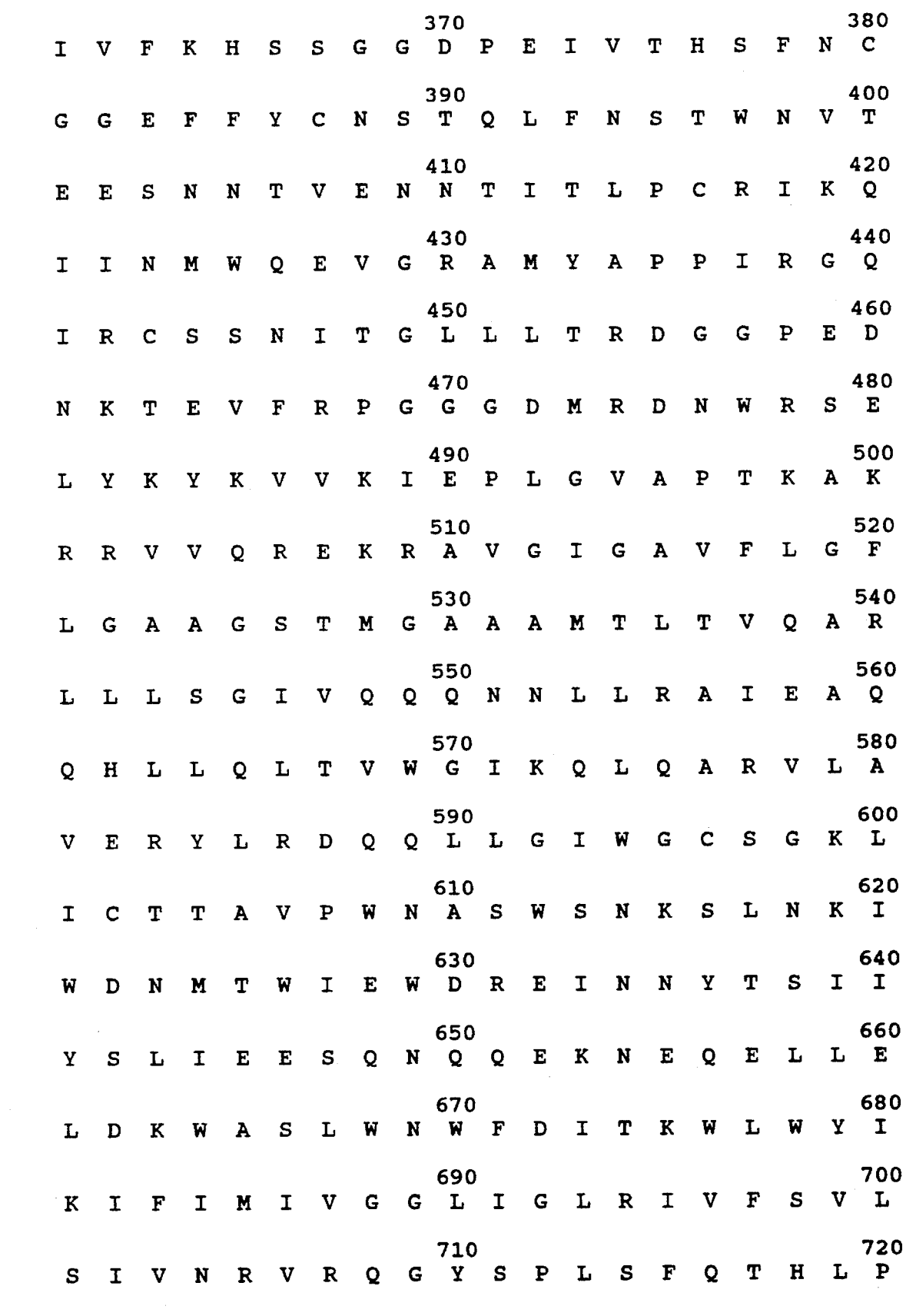
Figure 9C:
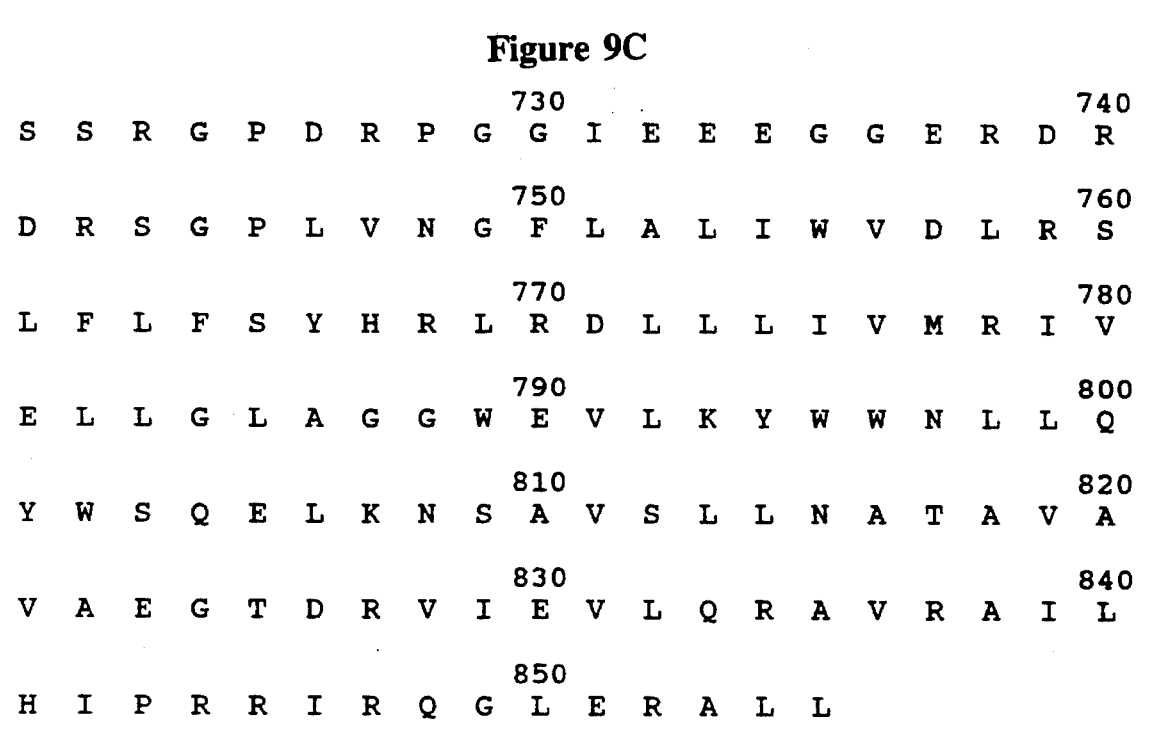

The amino acid sequence of the envelope protein, shown in FIGS. 9A–9C, and in SEQ ID NO:6, was inferred from the DNA sequence. A restriction map was also obtained from the DNA sequence of BA-L1 (shown in FIGS. 10A–10I) in order to determine the appropriate restriction enzyme sites for cloning the env gene into suitable expression vectors. An Eco RI-HindIII fragment of 0.4 Kb and a 2.8 Kb HindIII-Xba1 fragment when cloned together constitute the entire env gene. This plasmid contains, in addition to the coding regions for the envelope proteins, the coding region for the rev protein and the portion of the env protein which contains the rev-responsive region. Both are necessary for efficient expression of the envelope protein in eucaryotic cells (Feinberg et al., Cell 46, 807–817, 1986; Dayton et al., J. Acquir. Immune. Defic. Syndr. 1, 441–452). This plasmid thus contains all the HIV-1 genetic elements required for production of envelope protein following placement into appropriate expression vectors and introduction into recipient cells, all by standard techniques well known in the art.

Statement of Deposit

The lambda MN-ST1 clone and the BA-L plasmid clone were deposited at the American Type Culture Collection (Rockville, Md.) under the terms of the Budapest Treaty. The lambda MN-ST1 clone has been assigned the ATCC accession number ATCC 40889 and the BA-L plasmid clone has been assigned the ATCC accession number ATCC 40890.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. Isolated envelope protein of HIV-1 strain BA-L having the amino acid sequence of SEQ ID NO:6.

2. A recombinantly produced envelope protein of HIV-1 strain BA-L encoded by DNA contained within a 2.8 kilobase HindIII to XbaI DNA fragment and a 0.4 kilobase EcoRI to HindIII DNA fragment comprising the HIV-1 strain BA-L envelope gene.

3. An immunogenic preparation comprising the HIV-1 strain BA-L envelope protein according to claim 1, or claim 2 in an amount effective to induce an immune response against said envelope protein, and a pharmaceutically acceptable carrier.

4. The immunogenic preparation according to claim 3, further comprising an adjuvant.

5. A method of producing antibodies against HIV-1, comprising:

(a) administering to a mammal the immunogenic preparation of claim 3 or claim 4 in a series of about 2–3 doses given about 2–3 weeks apart; and (b) monitoring the level of circulating antibodies reactive with the HIV-1 envelope protein to determine the concentration of said circulating antibodies; and (c) repeating the series of administrations of step (a) if the circulating antibody concentration drops in the mammal.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 9739 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 6240..8810

( x i ) SEQUENCE DESCRIPTION: SEQ ID NO:1:

```
TGGAAGGGCT  AATTCACTCC  CAACGAAGAC  AAGATATCCT                              40
TGATCTGTGG  ATCTACCACA  CACAAGGCTA  CTTCCCTGAT                              80
TAGCAGAACT  ACACACCAGG  GCCAGGGATC  AGATATCCAC                             120
TGACCTTTGG  ATGGTGCTAC  AAGCTAGTAC  CAGTTGAGCC                             160
AGAGAAGTTA  GAAGAAGCCA  ACAAAGGAGA  GAACACCAGC                             200
TTGTTACACC  CTGTGAGCCT  GCATGGAATG  GATGACCCGG                             240
AGAGAGAAGT  GTTAGAGTGG  AGGTTTGACA  GCCGCCTAGC                             280
ATTTCATCAC  ATGGCCCGAG  AGCTGCATCC  GGAGTACTTC                             320
AAGAACTGCT  GACATCGAGC  TTGCTACAAG  GGACTTTCCG                             360
CTGGGGACTT  TCCAGGGAGG  CGTGGCCTGG  GCGGGACTGG                             400
GGAGTGGCGA  GCCCTCAGAT  CCTGCATATA  AGCAGCTGCT                             440
TTTTGCCTGT  ACTGGGTCTC  TCTGGTTAGA  CCAGATCTGA                             480
GCCTGGGAGC  TCTCTGGCTA  ACTAGGGAAC  CCACTGCTTA                             520
AGCCTCAATA  AAGCTTGCCT  TGAGTGCTTC  AAGTAGTGTG                             560
TGCCCGTCTG  TTATGTGACT  CTGGTAGCTA  GAGATCCCTC                             600
AGATCCTTTT  AGGCAGTGTG  GAAAATCTCT  AGCAGTGGCG                             640
CCCGAACAGG  GACTTGAAAG  CGAAAGAAAA  ACCAGAGCTC                             680
TCTCGACGCA  GGACTCGGCT  TGCTGAAGCG  CGCACGGCAA                             720
GAGGCGAGGG  GCGGCGACTG  GTGAGTACGC  CAAAAATTCT                             760
TGACTAGCGG  AGGCTAGAAG  GAGAGAGATG  GGTGCGAGAG                             800
CGTCGGTATT  AAGCGGGGGA  GAATTAGATC  GATGGGAAAA                             840
CATTCGGTTA  AGGCCAGGGG  GAAAGAAAAA  ATATAAATTA                             880
AAACATGTAG  TATGGGCAAG  CAGGGAGCTA  GAACGATTCG                             920
CAGTCAATCC  TGGCCTGTTA  GAAACATCAG  AAGGCTGTAG                             960
ACAAATACTG  GGACAGCTAC  AACCATCCCT  TCAGACAGGA                            1000
TCAGAAGAAC  TTAAATCATT  ATATAATACA  GTAGCAACCC                            1040
TCTATTGTGT  GCATCAAAAG  ATAGAGATAA  AGACACCAA                             1080
GGAAGCTTTA  GAGAAAATAG  AGGAAGAGCA  AAACAAAAGT                            1120
AAGAAAAAAG  CACAGCAAGC  AGCAGCTGAC  ACAGGAAACA                            1160
```

| | | | | |
|---|---|---|---|---|
| GAGGAAACAG | CAGCCAAGTC | AGCCAAAATT | ACCCCATAGT | 1200 |
| GCAGAACATC | GAGGGGCAAA | TGGTACATCA | GGCCATATCA | 1240 |
| CCTAGAACTT | TAAATGCATG | GGTAAAAGTA | GTAGAAGAGA | 1280 |
| AGGCTTTCAG | CCCAGAAGTA | ATACCCATGT | TTTCAGCATT | 1320 |
| ATCAGAAGGA | GCCACCCCAC | AAGATTTAAA | CACCATGCTA | 1360 |
| AACACAGTGG | GGGGACATCA | AGCAGCCATG | CAAATGTTAA | 1400 |
| AAGAGACCAT | CAATGAGGAA | GCTGCAGAAT | GGGATAGATT | 1440 |
| GCATCCAGTG | CATGCAGGGC | CTATTACACC | AGGCCAGATG | 1480 |
| AGAGAACCAA | GGGGAAGTGA | CATAGCAGGA | ACTACTAGTA | 1520 |
| CCCTTCAGGA | ACAAATAGGA | TGGATGACAA | ATAATCCACC | 1560 |
| TATCCCAGTA | GGAGAAATCT | ATAAAGATG | GATAATCCTG | 1600 |
| GGATTAAATA | AAATAGTAAG | GATGTATAGC | CCTTCCAGCA | 1640 |
| TTCTGGACAT | AAGACAAGGA | CCAAAGGAAC | CCTTTAGAGA | 1680 |
| CTATGTAGAC | CGGTTCTATA | AAACTCTAAG | AGCCGAGCAA | 1720 |
| GCTTCACAGG | AGGTAAAAAA | CCGGACGACA | GAAACCTTGT | 1760 |
| TGGTCCAAAA | TGCGAACCCA | GATTGTAAGA | CTATTTTAAA | 1800 |
| AGCATTGGGA | CCAGCAGCTA | CACTAGAAGA | AATGATGACA | 1840 |
| GCATGTCAGG | GAGTGGGAGG | ACCTGGTCAT | AAAGCAAGAG | 1880 |
| TTTTGGCGGA | AGCGATGAGC | CAAGTAACAA | ATTCAGCTAC | 1920 |
| CATAATGATG | CAGAGAGGCA | ATTTTAGGAA | TCAAAGAAAG | 1960 |
| ATTATCAAGT | GCTTCAATTG | TGGCAAAGAA | GGGCACATAG | 2000 |
| CCAAAAATTG | CAGGGCCCCT | AGGAAAAGGG | CTGTTGGAA | 2040 |
| ATGTGGAAAG | GAAGGACACC | AAATGAAAGA | TTGTACTGAG | 2080 |
| AGACAGGCTA | ATTTTTTAGG | GAAGATCTGG | CCTTCCTGCA | 2120 |
| AGGGAAGGCG | GAATTTTCCT | CAGAGCAGAA | CAGAGCCAAC | 2160 |
| AGCCCCACCA | GAAGAGAGCT | TCAGGTTTGG | GGAAGAGACA | 2200 |
| ACAACTCCCT | ATCAGAAGCA | GGAGAAGAAG | CAGGAGACGA | 2240 |
| TAGACAAGGA | CCTGTATCCT | TTAGCTTCCC | TCAAATCACT | 2280 |
| CTTTGGCAAC | GACCCATTGT | CACAATAAAG | ATAGGGGGC | 2320 |
| AACTAAAGGA | AGCTCTATTA | GATACAGGAG | CAGATGATAC | 2360 |
| AGTATTAGGA | GAAATGAATT | TGCCAAGAAG | ATGGAAACCA | 2400 |
| AAAATGATAG | GGGGAATTGG | AGGTTTTATC | AAAGTAAGAC | 2440 |
| AGTATGATCA | GATAACCATA | GAATCTGTG | ACATAAAGC | 2480 |
| TATAGGTACA | GTATTAGTAG | GACCTACACC | TGTCAACATA | 2520 |
| ATTGGAAGAA | ATCTGTTGAC | TCAGCTTGGG | TGCACTTTAA | 2560 |
| ATTTTCCCAT | TAGTCCTATT | GAAACTGTAC | CAGTAAAATT | 2600 |
| AAAGCCAGGA | ATGGATGGCC | CAAAAGTTAA | ACAATGGCCA | 2640 |
| TTGACAGAAG | AAAAAATAAA | AGCATTAATA | GAAATTTGTA | 2680 |
| CAGAAATGGA | AAAGGAAGGG | AAAATTTCAA | AAATTGGGCC | 2720 |
| TGAAAATCCA | TACAATACTC | CAGTATTTGC | CATAAAGAAA | 2760 |

| | | | | |
|---|---|---|---|---|
| AAAGACAGTA | CTAAATGGAG | AAAATTAGTA | GATTTCAGAG | 2800 |
| AACTTAATAA | GAAAACTCAA | GACTTCTGGG | AAGTTCAATT | 2840 |
| AGGAATACCA | CATCCTGCAG | GGTTAAAAAA | GAAAAAATCA | 2880 |
| GTAACAGTAC | TGGATGTGGG | TGATGCATAT | TTTTCAGTTC | 2920 |
| CCTTAGATAA | AGACTTCAGG | AAGTATACTG | CATTTACCAT | 2960 |
| ACCTAGTATA | AACAATGAAA | CACCAGGGAT | TAGATATCAG | 3000 |
| TACAATGTGC | TTCCACAGGG | ATGGAAAGGA | TCACCAGCAA | 3040 |
| TATTCCAAAG | TAGCATGACA | AAAATCTTAG | AGCCTTTTAG | 3080 |
| AAAACAAAAT | CCAGACATAG | TTATCTATCA | ATACATGGAT | 3120 |
| GATTTGTATG | TAGGATCTGA | CTTAGAAATA | GGGCAGCATA | 3160 |
| GAGCAAAAAT | AGAGGAACTG | AGACGACATC | TGTTGAGGTG | 3200 |
| GGGATTTACC | ACACCAGACA | AAAACATCA | GAAAGAACCT | 3240 |
| CCATTCCTTT | GGATGGGTTA | TGAACTCCAT | CCTGATAAAT | 3280 |
| GGACAGTACA | GCCTATAGTG | CTACCAGAAA | AAGACAGCTG | 3320 |
| GACTGTCAAT | GACATACAGA | AGTTAGTGGG | AAAATTGAAT | 3360 |
| TGGGCAAGTC | AGATTTACGC | AGGGATTAAA | GTAAAGCAAT | 3400 |
| TATGTAAACT | CCTTAGAGGA | ACCAAAGCAC | TAACAGAAGT | 3440 |
| AATACCACTA | ACAGAAGAAG | CAGAGCTAGA | ACTGGCAGAA | 3480 |
| AACAGGGAAA | TTCTAAAAGA | ACCAGTACAT | GGAGTGTATT | 3520 |
| ATGACCCATC | AAAAGACTTA | ATAGCAGAAG | TACAGAAGCA | 3560 |
| GGGGCAAGGC | CAATGGACAT | ATCAAATTTA | TCAAGAGCCA | 3600 |
| TTTAAAAATC | TGAAAACAGG | CAAATATGCA | AGAATGAGGG | 3640 |
| GTGCCCACAC | TAATGATGTA | AAACAATTAA | CAGAGGCAGT | 3680 |
| GCAAAAAATA | GCCACAGAAA | GCATAGTAAT | ATGGGGAAAG | 3720 |
| ACTCCTAAAT | TTAGACTACC | CATACAAAAA | GAAACATGGG | 3760 |
| AAACATGGTG | GACAGAGTAT | ACGTAAGCCA | CCTGGATTCC | 3800 |
| TGAGTGGGAG | GTTGTCAATA | CCCCTCCCTT | AGTGAAATTA | 3840 |
| TGGTACCAGT | TAGAGAAAGA | ACCCATAGTA | GGTGCAGAAA | 3880 |
| CTTTCTATGT | AGATGGGGCA | GCTAACAGGG | AGACTAAAAA | 3920 |
| AGGAAAAGCA | GGATATGTTA | CTAACAGAGG | AAGACAAAAG | 3960 |
| GTTGTCTCCC | TAACTGACAC | AACAAATCAG | AAGACTGAGT | 4000 |
| TACAAGCAAT | TCATCTAGCT | TTGCAAGATT | CAGGGTTAGA | 4040 |
| AGTAAACATA | GTAACAGACT | CACAATATGC | ATTAGGAATC | 4080 |
| ATTCAAGCAC | AACCAGATAA | AAGTGAATCA | GAGTTAGTCA | 4120 |
| GTCAAATAAT | AGAGCAGTTA | ATAAAAAGG | AAAAGGTCTA | 4160 |
| TCTGGCATGG | GTACCAGCAC | ACAAAGGAAT | TGGAGGAAAT | 4200 |
| GAACAAGTAG | ATAAATTAGT | CAGTGCTGGA | ATCAGGAAAG | 4240 |
| TACTATTTTT | AGATGGAATA | GATAAGGCCC | AAGAAGACCA | 4280 |
| TGAGAAATAT | CACAGTAATT | GGAGAGCAAT | GGCTAGTGAC | 4320 |
| TTTAACCTAC | CACCTATAGT | AGCAAAAGAA | ATAGTAGCCA | 4360 |

-continued

| | | | | |
|---|---|---|---|---|
| GCTGTGATAA | ATGTCAGCTA | AAAGGAGAAG | CCATGCATGG | 4400 |
| ACAAGTAGAC | TGTAGTCCAG | GAATATGGCA | ACTAGATTGT | 4440 |
| ACACATTTAG | AAGGAAAAGT | TATCCTGGTA | GCAGTTCATG | 4480 |
| TAGCCAGTGG | ATACATAGAA | GCAGAAGTTA | TTCCAGCAGA | 4520 |
| GACAGGGCAG | GAGACAGCAT | ACTTTCTCTT | AAAATTAGCA | 4560 |
| GGAAGATGGC | CAGTAAAAAC | AATACATACA | GACAATGGCC | 4600 |
| CCAATTTCAC | CAGTACTACG | GTTAAGGCCG | CCTGTTGGTG | 4640 |
| GACGGGAATC | AAGCAGGAAT | TTGGCATTCC | CTACAATCCC | 4680 |
| CAAAGTCAAG | GAGTAATAGA | ATCTATGAAT | AAAGAATTAA | 4720 |
| AGAAAATTAT | AGGACAGGTA | AGAGATCAGG | CTGAACATCT | 4760 |
| TAAGAGAGCA | GTACAAATGG | CAGTATTCAT | CCACAATTTT | 4800 |
| AAAAGAAAAG | GGGGGATTGG | GGGGTACAGT | GCAGGGGAAA | 4840 |
| GAATAGTAGG | CATAATAGCA | ACAGACATAC | AAACTAAAGA | 4880 |
| ACTACAAAAA | CAAATTACAA | AAATTCAAAA | TTTTCGGGTT | 4920 |
| TATTACAGGG | ACAGCAGAGA | TCCACTTTGG | AAAGGACCAG | 4960 |
| CAAAGCTTCT | CTGGAAAGGT | GAAGGGGCAG | TAGTAATACA | 5000 |
| AGATAATAAT | GACATAAAAG | TAGTGCCAAG | AAGAAAAGCA | 5040 |
| AAGGTCATTA | GGGATTATGG | AAAACAGACG | GCAGGTGATG | 5080 |
| ATTGTGTGGC | AAGCAGACAG | GATGAGGATT | AGAACATGGA | 5120 |
| AAAGTTTAGT | AAAACACCAT | ATGTATATTT | CAAAGAAAGC | 5160 |
| TAAAGGACGG | TTTTATAGAC | ATCACTATGA | AAGCACTCAT | 5200 |
| CCAAGAATAA | GTTCAGAAGT | ACACATCCCA | CTAGGGGATG | 5240 |
| CTAGATTGGT | AATAACAACA | TATTGGGGTC | TGCATACAGG | 5280 |
| AGAAAGAGAC | TGGCATTTAG | GTCAGGGAGT | CTCCATAGAA | 5320 |
| TGGAGGAAAA | AGAGATATAG | CACACAAGTA | GACCCTGACC | 5360 |
| TAGCAGACCA | CCTAATTCAT | CTGCATTACT | TTGATTGTTT | 5400 |
| TTCAGACTCT | GCCATAAGAA | AGGCCATATT | AGGACATAGA | 5440 |
| GTTAGTCCTA | TTTGTGAATT | TCAAGCAGGA | CATAACAAGG | 5480 |
| TAGGACCTCT | ACAGTACTTG | GCACTAACAG | CATTAATAAC | 5520 |
| ACCAAAAAAG | ATAAAGCCAC | CTTTGCCTAG | TGTTAAGAAA | 5560 |
| CTGACAGAGG | ATAGATGGAA | CAAGCCCCAG | AAGACCAAGG | 5600 |
| GCCACAGAGG | GAGCCATACA | ATCAATGGGC | ACTAGAGCTT | 5640 |
| TTAGAGGAGC | TTAAGAATGA | AGCTGTTAGA | CATTTTCCTA | 5680 |
| GGATATGGCT | CCATGGCTTA | GGGCAACATA | TCTATGAAAC | 5720 |
| TTATGGGGAT | ACTTGGGCAG | GAGTGGAAGC | CATAATAAGA | 5760 |
| ATTCTACAAC | AACTGCTGTT | TATTCATTTC | AGAATTGGGT | 5800 |
| GTCGACATAG | CAGAATAGGC | ATTATTCGAC | AGAGGAGAGC | 5840 |
| AAGAAATGGA | GCCAGTAGAT | CCTAGACTAG | AGCCCTGGAA | 5880 |
| GCATCCAGGA | AGTCAGCCTA | AGACTGCTTG | TACCACTTGC | 5920 |
| TATTGTAAAA | AGTGTTGCTT | TCATTGCCAA | GTTTGTTTCA | 5960 |

| | | | | |
|---|---|---|---|---|
| CAAAAAAAGC | CTTAGGCATC | TCCTATGGCA | GGAAGAAGCG | 6000 |
| GAGACAGCGA | CGAAGAGCTC | CTGAAGACAG | TCAGACTCAT | 6040 |
| CAAGTTTCTC | TACCAAAGCA | GTAAGTAGTA | CATGTAATGC | 6080 |
| AACCTTTAGT | AATAGCAGCA | ATAGTAGCAT | TAGTAGTAGC | 6120 |
| AGGAATAATA | GCAATAGTTG | TGTGATCCAT | AGTATTCATA | 6160 |
| GAATATAGGA | AAATAAGAAG | ACAAGAAAA | ATAGACAGGT | 6200 |
| TAATTGATAG | AATAAGCGAA | AGAGCAGAAG | ACAGTGGCAA | 6240 |
| TGAGAGTGAA | GGGGATCAGG | AGGAATTATC | AGCACTGGTG | 6280 |
| GGGATGGGGC | ACGATGCTCC | TTGGGTTATT | AATGATCTGT | 6320 |
| AGTGCTACAG | AAAAATTGTG | GGTCACAGTC | TATTATGGGG | 6360 |
| TACCTGTGTG | GAAAGAAGCA | ACCACCACTC | TATTTTGTGC | 6400 |
| ATCAGATGCT | AAAGCATATG | ATACAGAGGT | ACATAATGTT | 6440 |
| TGGGCCACAC | AAGCCTGTGT | ACCCACAGAC | CCCAACCCAC | 6480 |
| AAGAAGTAGA | ATTGGTAAAT | GTGACAGAAA | ATTTTAACAT | 6520 |
| GTGGAAAAAT | AACATGGTAG | AACAGATGCA | TGAGGATATA | 6560 |
| ATCAGTTTAT | GGGATCAAAG | CCTAAAGCCA | TGTGTAAAAT | 6600 |
| TAACCCCACT | CTGTGTTACT | TTAAATTGCA | CTGATTTGAG | 6640 |
| GAATACTACT | AATACCAATA | ATAGTACTGC | TAATAACAAT | 6680 |
| AGTAATAGCG | AGGGAACAAT | AAAGGGAGGA | GAAATGAAAA | 6720 |
| ACTGCTCTTT | CAATATCACC | ACAAGCATAA | GAGATAAGAT | 6760 |
| GCAGAAAGAA | TATGCACTTC | TTTATAAACT | TGATATAGTA | 6800 |
| TCAATAGATA | ATGATAGTAC | CAGCTATAGG | TTGATAAGTT | 6840 |
| GTAATACCTC | AGTCATTACA | CAAGCTTGTC | CAAAGATATC | 6880 |
| CTTTGAGCCA | ATTCCCATAC | ACTATTGTGC | CCCGGCTGGT | 6920 |
| TTTGCGATTC | TAAAATGTAA | CGATAAAAAG | TTCAGTGGAA | 6960 |
| AAGGATCATG | TAAAAATGTC | AGCACAGTAC | AATGTACACA | 7000 |
| TGGAATTAGG | CCAGTAGTAT | CAACTCAACT | GCTGTTAAAT | 7040 |
| GGCAGTCTAG | CAGAAGAAGA | GGTAGTAATT | AGATCTGAGA | 7080 |
| ATTTCACTGA | TAATGCTAAA | ACCATCATAG | TACATCTGAA | 7120 |
| TGAATCTGTA | CAAATTAATT | GTACAAGACC | CAACTACAAT | 7160 |
| AAAAGAAAAA | GGATACATAT | AGGACCAGGG | AGAGCATTTT | 7200 |
| ATACAACAAA | AAATATAATA | GGAACTATAA | GACAAGCACA | 7240 |
| TTGTAACATT | AGTAGAGCAA | AATGGAATGA | CACTTTAAGA | 7280 |
| CAGATAGTTA | GCAAATTAAA | AGAACAATTT | AAGAATAAAA | 7320 |
| CAATAGTCTT | TAATCAATCC | TCAGGAGGGG | ACCCAGAAAT | 7360 |
| TGTAATGCAC | AGTTTTAATT | GTGGAGGGGA | ATTTTTCTAC | 7400 |
| TGTAATACAT | CACCACTGTT | TAATAGTACT | TGGAATGGTA | 7440 |
| ATAATACTTG | GAATAATACT | ACAGGGTCAA | ATAACAATAT | 7480 |
| CACACTTCAA | TGCAAAATAA | AACAAATTAT | AAACATGTGG | 7520 |
| CAGGAAGTAG | GAAAAGCAAT | GTATGCCCCT | CCCATTGAAG | 7560 |

```
GACAAATTAG ATGTTCATCA AATATTACAG GGCTACTATT              7600
AACAAGAGAT GGTGGTAAGG ACACGGACAC GAACGACACC              7640
GAGATCTTCA GACCTGGAGG AGGAGATATG AGGGACAATT              7680
GGAGAAGTGA ATTATATAAA TATAAAGTAG TAACAATTGA              7720
ACCATTAGGA GTAGCACCCA CCAAGGCAAA GAGAAGAGTG              7760
GTGCAGAGAG AAAAAAGAGC AGCGATAGGA GCTCTGTTCC              7800
TTGGGTTCTT AGGAGCAGCA GGAAGCACTA TGGGCGCAGC              7840
GTCAGTGACG CTGACGGTAC AGGCCAGACT ATTATTGTCT              7880
GGTATAGTGC AACAGCAGAA CAATTTGCTG AGGGCCATTG              7920
AGGCGCAACA GCATATGTTG CAACTCACAG TCTGGGCAT               7960
CAAGCAGCTC CAGGCAAGAG TCCTGGCTGT GGAAAGATAC              8000
CTAAAGGATC AACAGCTCCT GGGGTTTTGG GGTTGCTCTG              8040
GAAAACTCAT TTGCACCACT ACTGTGCCTT GGAATGCTAG              8080
TTGGAGTAAT AAATCTCTGG ATGATATTTG AATAACATG               8120
ACCTGGATGC AGTGGGAAAG AGAAATTGAC AATTACACAA              8160
GCTTAATATA CTCATTACTA GAAAATCGC AAACCCAACA                8200
AGAAAAGAAT GAACAAGAAT TATTGGAATT GGATAAATGG              8240
GCAAGTTTGT GGAATTGGTT TGACATAACA AATTGGCTGT              8280
GGTATATAAA AATATTCATA ATGATAGTAG GAGGCTTGGT              8320
AGGTTTAAGA ATAGTTTTTG CTGTACTTTC TATAGTGAAT              8360
AGAGTTAGGC AGGGATACTC ACCATTGTCG TTGCAGACCC              8400
GCCCCCCAGT TCCGAGGGGA CCCGACAGGC CCGAAGGAAT              8440
CGAAGAAGAA GGTGGAGAGA GAGACAGAGA CACATCCGGT              8480
CGATTAGTGC ATGGATTCTT AGCAATTATC TGGGTCGACC              8520
TGCGGAGCCT GTTCCTCTTC AGCTACCACC ACAGAGACTT              8560
ACTCTTGATT GCAGCGAGGA TTGTGGAACT TCTGGGACGC              8600
AGGGGGTGGG AAGTCCTCAA ATATTGGTGG AATCTCCTAC              8640
AGTATTGGAG TCAGGAACTA AGAGTAGTG CTGTTAGCTT               8680
GCTTAATGCC ACAGCTATAG CAGTAGCTGA GGGGACAGAT              8720
AGGGTTATAG AAGTACTGCA AAGAGCTGGT AGAGCTATTC              8760
TCCACATACC TACAAGAATA AGACAGGGCT TGGAAAGGGC              8800
TTTGCTATAA GATGGGTGGC AAATGGTCAA AACGTGTGAC              8840
TGGATGGCCT ACTGTAAGGG AAAGAATGAG ACGAGCTGAA              8880
CCAGCTGAGC TAGCAGCAGA TGGGGTGGGA GCAGCATCCC              8920
GAGACCTGGA AAAACATGGA GCACTCACAA GTAGCAATAC              8960
AGCAGCTACC AATGCTGATT GTGCCTGGCT AGAAGCACAA              9000
GAGGAGGAGG AAGTGGGTTT CCAGTCAAA CCTCAGGTAC                9040
CTTTAAGACC AATGACTTAC AAAGCAGCTT TAGATCTTAG              9080
CCACTTTTTA AAAGAAAAGG GGGGACTGGA TGGGTTAATT              9120
TACTCCCAAA AGAGACAAGA CATCCTTGAT CTGTGGGTCT              9160
```

| | | | |
|---|---|---|---|
| ACCACACACA | AGGCTACTTC | CCTGATTGGC | AGAACTACAC | 9200 |
| ACCAGGGCCA | GGGATCAGAT | ATCCACTGAC | CTTTGGATGG | 9240 |
| TGCTTCAAGC | TAGTACCAGT | TGAGCCAGAG | AAGATAGAAG | 9280 |
| AGGCCAATAA | AGGAGAGAAC | AACTGCTTGT | TACACCCTAT | 9320 |
| GAGCCAGCAT | GGATGGATGA | CCCGGAGAGA | GAAGTGTTAG | 9360 |
| TGTGGAAGTC | TGACAGCCAC | CTAGCATTTC | AGCATTATGC | 9400 |
| CCGAGAGCTG | CATCCGGAGT | ACTACAAGAA | CTGCTGACAT | 9440 |
| CGAGCTATCT | ACAAGGGACT | TTCCGCTGGG | GACTTTCCAG | 9480 |
| GGAGGTGTGG | CCTGGGCGGG | ACCGGGGAGT | GGCGAGCCCT | 9520 |
| CAGATCGTGC | ATATAAGCAG | CTGCTTTCTG | CCTGTACTGG | 9560 |
| GTCTCTCTGG | TTAGACCAGA | TCTGAGCCTG | GGAGCTCTCT | 9600 |
| GGCTAACTAG | GGAACCCACT | GCTTAAGCCT | CAATAAAGCT | 9640 |
| TGCCTTGAGT | GCTTCAAGTA | GTGTGTGCCC | GTCTGTTATG | 9680 |
| TGACTCTGGT | AGCTAGAGAT | CCCTCAGATC | CTTTTAGGCA | 9720 |
| GTGTGGAAAA | TCTCTAGCA | | | 9739 |

( 2 ) INFORMATION FOR SEQ ID NO:2:

( i ) SEQUENCE CHARACTERISTICS:
          ( A ) LENGTH: 856 amino acids
          ( B ) TYPE: amino acid
          ( D ) TOPOLOGY: linear ( i i ) MOLECULE TYPE: protein ( i x ) SEQUENCE DESCRIPTION: SEQ ID NO:2:

```
Met  Arg  Val  Lys  Gly  Ile  Arg  Arg  Asn  Tyr  Gln  His
 1              5                        10

Trp  Trp  Gly  Trp  Gly  Thr  Met  Leu  Leu  Gly  Leu  Leu
         15                        20

Met  Ile  Cys  Ser  Ala  Thr  Glu  Lys  Leu  Trp  Val  Thr
25                       30                       35

Val  Tyr  Tyr  Gly  Val  Pro  Val  Trp  Lys  Glu  Ala  Thr
              40                       45

Thr  Thr  Leu  Phe  Cys  Ala  Ser  Asp  Ala  Lys  Ala  Tyr
     50                       55                       60

Asp  Thr  Glu  Val  His  Asn  Val  Trp  Ala  Thr  Gln  Ala
                   65                       70

Cys  Val  Pro  Thr  Asp  Pro  Asn  Pro  Gln  Glu  Val  Glu
               75                       80

Leu  Val  Asn  Val  Thr  Glu  Asn  Phe  Asn  Met  Trp  Lys
85                       90                       95

Asn  Asn  Met  Val  Glu  Gln  Met  His  Glu  Asp  Ile  Ile
               100                      105

Ser  Leu  Trp  Asp  Gln  Ser  Leu  Lys  Pro  Cys  Val  Lys
     110                      115                      120

Leu  Thr  Pro  Leu  Cys  Val  Thr  Leu  Asn  Cys  Thr  Asp
                   125                      130

Leu  Arg  Asn  Thr  Thr  Asn  Thr  Asn  Asn  Ser  Thr  Ala
          135                      140

Asn  Asn  Asn  Ser  Asn  Ser  Glu  Gly  Thr  Ile  Lys  Gly
145                      150                      155
```

```
Gly Glu Met Lys Asn Cys Ser Phe Asn Ile Thr Thr
            160                 165

Ser Ile Arg Asp Lys Met Gln Lys Glu Tyr Ala Leu
        170             175                 180

Leu Tyr Lys Leu Asp Ile Val Ser Ile Asp Asn Asp
                185                 190

Ser Thr Ser Tyr Arg Leu Ile Ser Cys Asn Thr Ser
        195                 200

Val Ile Thr Gln Ala Cys Pro Lys Ile Ser Phe Glu
205                 210                 215

Pro Ile Pro Ile His Tyr Cys Ala Pro Ala Gly Phe
        220                 225

Ala Ile Leu Lys Cys Asn Asp Lys Lys Phe Ser Gly
        230                 235                 240

Lys Gly Ser Cys Lys Asn Val Ser Thr Val Gln Cys
                245                 250

Thr His Gly Ile Arg Pro Val Val Ser Thr Gln Leu
        255                 260

Leu Leu Asn Gly Ser Leu Ala Glu Glu Val Val
265                 270                 275

Ile Arg Ser Glu Asn Phe Thr Asp Asn Ala Lys Thr
        280                 285

Ile Ile Val His Leu Asn Glu Ser Val Gln Ile Asn
        290                 295                 300

Cys Thr Arg Pro Asn Tyr Asn Lys Arg Lys Arg Ile
                305                 310

His Ile Gly Pro Gly Arg Ala Phe Tyr Thr Thr Lys
        315                 320

Asn Ile Ile Gly Thr Ile Arg Gln Ala His Cys Asn
325                 330                 335

Ile Ser Arg Ala Lys Trp Asn Asp Thr Leu Arg Gln
            340                 345

Ile Val Ser Lys Leu Lys Glu Gln Phe Lys Asn Lys
        350                 355                 360

Thr Ile Val Phe Asn Gln Ser Ser Gly Gly Asp Pro
                365                 370

Glu Ile Val Met His Ser Phe Asn Cys Gly Gly Glu
        375                 380

Phe Phe Tyr Cys Asn Thr Ser Pro Leu Phe Asn Ser
385                 390                 395

Thr Trp Asn Gly Asn Asn Thr Trp Asn Asn Thr Thr
            400                 405

Gly Ser Asn Asn Asn Ile Thr Leu Gln Cys Lys Ile
        410                 415                 420

Lys Gln Ile Ile Asn Met Trp Gln Glu Val Gly Lys
                425                 430

Ala Met Tyr Ala Pro Pro Ile Glu Gly Gln Ile Arg
        435                 440

Cys Ser Ser Asn Ile Thr Gly Leu Leu Leu Thr Arg
445                 450                 455

Asp Gly Gly Lys Asp Thr Asp Thr Asn Asp Thr Glu
            460                 465

Ile Phe Arg Pro Gly Gly Gly Asp Met Arg Asp Asn
```

|     |     |     |     | 470 |     |     |     | 475 |     |     |     | 480 |     |
| --- | --- | --- | --- | --- | --- | --- | --- | --- | --- | --- | --- | --- | --- |
| Trp | Arg | Ser | Glu | Leu | Tyr | Lys | Tyr | Lys | Val | Val | Thr |     |     |
|     |     |     |     | 485 |     |     |     |     | 490 |     |     |     |     |
| Ile | Glu | Pro | Leu | Gly | Val | Ala | Pro | Thr | Lys | Ala | Lys |     |     |
|     |     | 495 |     |     |     |     | 500 |     |     |     |     |     |     |
| Arg | Arg | Val | Val | Gln | Arg | Glu | Lys | Arg | Ala | Ala | Ile |     |     |
| 505 |     |     |     |     | 510 |     |     |     |     | 515 |     |     |     |
| Gly | Ala | Leu | Phe | Leu | Gly | Phe | Leu | Gly | Ala | Ala | Gly |     |     |
|     |     |     | 520 |     |     |     |     | 525 |     |     |     |     |     |
| Ser | Thr | Met | Gly | Ala | Ala | Ser | Val | Thr | Leu | Thr | Val |     |     |
|     | 530 |     |     |     |     | 535 |     |     |     |     | 540 |     |     |
| Gln | Ala | Arg | Leu | Leu | Leu | Ser | Gly | Ile | Val | Gln | Gln |     |     |
|     |     |     |     | 545 |     |     |     |     | 550 |     |     |     |     |
| Gln | Asn | Asn | Leu | Leu | Arg | Ala | Ile | Glu | Ala | Gln | Gln |     |     |
|     |     | 555 |     |     |     |     | 560 |     |     |     |     |     |     |
| His | Met | Leu | Gln | Leu | Thr | Val | Trp | Gly | Ile | Lys | Gln |     |     |
| 565 |     |     |     |     | 570 |     |     |     |     | 575 |     |     |     |
| Leu | Gln | Ala | Arg | Val | Leu | Ala | Val | Glu | Arg | Tyr | Leu |     |     |
|     |     |     | 580 |     |     |     |     | 585 |     |     |     |     |     |
| Lys | Asp | Gln | Gln | Leu | Leu | Gly | Phe | Trp | Gly | Cys | Ser |     |     |
| 590 |     |     |     |     |     | 595 |     |     |     |     | 600 |     |     |
| Gly | Lys | Leu | Ile | Cys | Thr | Thr | Thr | Val | Pro | Trp | Asn |     |     |
|     |     |     |     | 605 |     |     |     |     | 610 |     |     |     |     |
| Ala | Ser | Trp | Ser | Asn | Lys | Ser | Leu | Asp | Asp | Ile | Trp |     |     |
|     |     | 615 |     |     |     |     | 620 |     |     |     |     |     |     |
| Asn | Asn | Met | Thr | Trp | Met | Gln | Trp | Glu | Arg | Glu | Ile |     |     |
| 625 |     |     |     |     | 630 |     |     |     |     | 635 |     |     |     |
| Asp | Asn | Tyr | Thr | Ser | Leu | Ile | Tyr | Ser | Leu | Leu | Glu |     |     |
|     |     |     | 640 |     |     |     |     | 645 |     |     |     |     |     |
| Lys | Ser | Gln | Thr | Gln | Gln | Glu | Lys | Asn | Glu | Gln | Glu |     |     |
|     | 650 |     |     |     |     | 655 |     |     |     |     | 660 |     |     |
| Leu | Leu | Glu | Leu | Asp | Lys | Trp | Ala | Ser | Leu | Trp | Asn |     |     |
|     |     |     |     | 665 |     |     |     |     | 670 |     |     |     |     |
| Trp | Phe | Asp | Ile | Thr | Asn | Trp | Leu | Trp | Tyr | Ile | Lys |     |     |
|     |     | 675 |     |     |     |     | 680 |     |     |     |     |     |     |
| Ile | Phe | Ile | Met | Ile | Val | Gly | Gly | Leu | Val | Gly | Leu |     |     |
| 685 |     |     |     |     | 690 |     |     |     |     | 695 |     |     |     |
| Arg | Ile | Val | Phe | Ala | Val | Leu | Ser | Ile | Val | Asn | Arg |     |     |
|     |     |     | 700 |     |     |     |     | 705 |     |     |     |     |     |
| Val | Arg | Gln | Gly | Tyr | Ser | Pro | Leu | Ser | Leu | Gln | Thr |     |     |
|     | 710 |     |     |     |     | 715 |     |     |     |     | 720 |     |     |
| Arg | Pro | Pro | Val | Pro | Arg | Gly | Pro | Asp | Arg | Pro | Glu |     |     |
|     |     |     |     | 725 |     |     |     |     | 730 |     |     |     |     |
| Gly | Ile | Glu | Glu | Glu | Gly | Gly | Glu | Arg | Asp | Arg | Asp |     |     |
|     |     | 735 |     |     |     |     | 740 |     |     |     |     |     |     |
| Thr | Ser | Gly | Arg | Leu | Val | His | Gly | Phe | Leu | Ala | Ile |     |     |
| 745 |     |     |     |     | 750 |     |     |     |     | 755 |     |     |     |
| Ile | Trp | Val | Asp | Leu | Arg | Ser | Leu | Phe | Leu | Phe | Ser |     |     |
|     |     |     | 760 |     |     |     |     | 765 |     |     |     |     |     |
| Tyr | His | His | Arg | Asp | Leu | Leu | Leu | Ile | Ala | Ala | Arg |     |     |
|     | 770 |     |     |     |     | 775 |     |     |     |     | 780 |     |     |
| Ile | Val | Glu | Leu | Leu | Gly | Arg | Arg | Gly | Trp | Glu | Val |     |     |
|     |     |     |     | 785 |     |     |     |     | 790 |     |     |     |     |

| | | | | | | | | | |
|---|---|---|---|---|---|---|---|---|---|
| Leu | Lys | Tyr | Trp | Trp | Asn | Leu | Leu | Gln | Tyr | Trp | Ser |
| | | 795 | | | | | 800 | | | | |
| Gln | Glu | Leu | Lys | Ser | Ser | Ala | Val | Ser | Leu | Leu | Asn |
| 805 | | | | | 810 | | | | | 815 | |
| Ala | Thr | Ala | Ile | Ala | Val | Ala | Glu | Gly | Thr | Asp | Arg |
| | | | 820 | | | | | 825 | | | |
| Val | Ile | Glu | Val | Leu | Gln | Arg | Ala | Gly | Arg | Ala | Ile |
| | 830 | | | | | 835 | | | | | 840 |
| Leu | His | Ile | Pro | Thr | Arg | Ile | Arg | Gln | Gly | Leu | Glu |
| | | | | 845 | | | | | 850 | | |
| Arg | Ala | Leu | Leu | | | | | | | | |
| | | 855 | | | | | | | | | |

( 2 ) INFORMATION FOR SEQ ID NO:3:

( i ) SEQUENCE CHARACTERISTICS:
        ( A ) LENGTH: 9746 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 6243..8816

( x i ) SEQUENCE DESCRIPTION: SEQ ID NO:3:

| | | | | |
|---|---|---|---|---|
| TGGATGGGTT | AATTTACTCC | CAAAGAGACA | AGACATCCTT | 40 |
| GATCTGTGGG | TCTACCACAC | ACAAGGCTAC | TTCCCTGATT | 80 |
| GGCAGAACTA | CACACCAGGG | CCAGGGATCA | GATATCCACT | 120 |
| GACCTTTGGA | TGGTGCTTCA | AGCTAGTACC | AGTTGAGCCA | 160 |
| GAGAAGATAG | AAGAGGCCAA | TAAAGGAGAG | AACAACTGCT | 200 |
| TGTTACACCC | TATGAGCCAG | CATGGGATGG | ATGACCCGGA | 240 |
| GAGAGAAGTG | TTAGTGTGGA | AGTCTGACAG | CCACCTAGCA | 280 |
| TTTCAGCATT | ATGCCCGAGA | GCTGCATCCG | GAGTACTACA | 320 |
| AGAACTGCTG | ACATCGAGCT | ATCTACAAGG | GACTTTCCGC | 360 |
| TGGGGACTTT | CCAGGGAGGT | GTGGCCTGGG | CGGGACCGGG | 400 |
| GAGTGGCGAG | CCCTCAGATG | CTGCATATAA | GCAGCTGCTT | 440 |
| TCTGCCTGTA | CTGGGTCTCT | CTGGTTAGAC | CAGATCTGAG | 480 |
| CCTGGGAGCT | CTCTGGCTAA | CTAGGGAACC | CACTGCTTAA | 520 |
| GCCTCAATAA | AGCTTGCCTT | GAGTGCTTCA | AGTAGTGTGT | 560 |
| GCCCGTCTGT | TATGTGACTC | TGGTAGCTAG | AGATCCCTCA | 600 |
| GATCCTTTTA | GGCAGTGTGG | AAAATCTCTA | GCAGTGGCGC | 640 |
| CCGAACAGGG | ACTTGAAAGC | GAAAGAGAAA | CCAGAGGAGC | 680 |
| TCTCTCGACG | CAGGACTCGG | CTTGCTGAAG | CGCGCACGGC | 720 |
| AAGAGGCGAG | GGGCGGCGAC | TGGTGAGTAC | GCCAAAATTC | 760 |
| TTGACTAGCG | GAGGCTAGAA | GGAGAGAGAT | GGGTGCGAGA | 800 |
| GCGTCGGTAT | TAAGCGGGGG | AGAATTAGAT | CGATGGGAAA | 840 |
| AAATTCGGTT | AAGGCCAGGG | GGAAAGAAAA | AATATAAATT | 880 |
| AAAACATGTA | GTATGGGCAA | GCAGGGAGCT | AGAACGATTC | 920 |
| GCAGTCAATC | CTGGCCTGTT | AGAAACATCA | GAAGGCTGTA | 960 |

| | |
|---|---|
| GACAAATACT GGGACAGCTA CAACCATCCC TTCAGACAGG | 1000 |
| ATCAGAAGAA CTTAAATCAT TATATAATAC AGTAGCAACC | 1040 |
| CTCTATTGTG TGCATCAAAA GATAGAGATA AAAGACACCA | 1080 |
| AGGAAGCTTT AGAGAAAATA GAGGAAGAGC AAAACAAAAG | 1120 |
| TAAGAAAAAA GCACAGCAAG CAGTAGCTGA CACAGGAAAC | 1160 |
| AGAGGAAACA GCAGCCAAGT CAGCCAAAAT TACCCCATAG | 1200 |
| TGCAGAACAT CCAGGGGCAA ATGGTACATC AGGCCATATC | 1240 |
| ACCTAGAACT TTAAATGCAT GGGTAAAAGT AGTAGAAGAG | 1280 |
| AAGGCTTTCA GCCCAGAAGT AATACCCATG TTTTCAGCAT | 1320 |
| TATCAGAAGG AGCCACCCCA CAAGATTTAA ACACCATGCT | 1360 |
| AAACACAGTG GGGGGACATC AAGCAGCCAT GCAAATGTTA | 1400 |
| AAAGAGACCA TCAATGAGGA AGCTGCAGAA TGGGATAGAT | 1440 |
| TGCATCCAGT GCATGCAGGG CCTATTGCAC CAGGCCAGAT | 1480 |
| GAGAGAACCA AGGGGAAGTG ACATAGCAGG AACTACTAGT | 1520 |
| ACCCTTCAGG AACAAATAGG ATGGATGACA AATAATCCAC | 1560 |
| CTATCCCAGT AGGAGAAATC TATAAAAGAT GGATAATCCT | 1600 |
| GGGATTAAAT AAAATAGTAA GGATGTATAG CCCTTCCAGC | 1640 |
| ATTCTGGACA TAAGACAAGG ACCAAAGGAA CCCTTTAGAG | 1680 |
| ACTATGTAGA CCGGTTCTAT AAAACTCTAA GAGCCGAGCA | 1720 |
| AGCTTCACAG GAGGTAAAAA ATTGGATGAC AGAAACCTTG | 1760 |
| TTGGTCCAAA ATGCGAACCC AGATTGTAAG ACTATTTTAA | 1800 |
| AAGCATTGGG ACCAGCAGCT ACACTAGAAG AAATGATGAC | 1840 |
| AGCATGTCAG GGAGTGGGAG GACCTGGTCA TAAAGCAAGA | 1880 |
| GTTTTGGCGG AAGCGATGAG CCAAGTAACA AATTCAGCTA | 1920 |
| CCATAATGAT GCAGAGAGGC AATTTTAGGA ATCAAAGAAA | 1960 |
| GATTATCAAG TGCTTCAATT GTGGCAAAGA AGGGCACATA | 2000 |
| GCCAAAAATT GCAGGGCCCC TAGGAAAAGG GGCTGTTGGA | 2040 |
| AATGTGGAAA GGAAGGACAC CAAATGAAAG ATTGTACTGA | 2080 |
| GAGACAGGCT AATTTTTTAG GAAGATCTG GCCTTCCTGC | 2120 |
| AAGGGAAGGC AGGGAATTTT CCTCAGAGCA GAACAGAGCC | 2160 |
| AACAGCCCCA CCAGAAGAGA GCTTCAGGTT TGGGGAAGAG | 2200 |
| ACAACAACTC CCTATCAGAA GCAGGAGAAG AAGCAGGAGA | 2240 |
| CGATAGACAA GGACCTGTAT CCTTTAGCTT CCCTCAAATC | 2280 |
| ACTCTTTGGC AACGACCCAT TGTCACAATA AAGATAGGGG | 2320 |
| GGCAACTAAA GGAAGCTCTA TTAGATACAG GAGCAGATGA | 2360 |
| TACAGTATTA GAAGAAATGA ATTTGCCAGG AAGATGGAAA | 2400 |
| CCAAAAATGA TAGGGGGAAT TGGAGGTTTT ATCAAAGTAA | 2440 |
| GACAGTATGA TCAGATAACC ATAGAAATCT GTGGACATAA | 2480 |
| AGCTATAGGT ACAGTATTAG TAGGACCTAC ACCTGTCAAC | 2520 |
| ATAATTGGAA GAAATCTGTT GACTCAGCTT GGGTGCACTT | 2560 |

```
TAAATTTTCC CATTAGTCCT ATTGAAACTG TACCAGTAAA              2600

ATTAAAGCCA GGAATGGATG GCCCAAAAGT TAAACAATGG              2640

CCATTGACAG AAGAAAAAAT AAAAGCATTA ATAGAAATTT              2680

GTACAGAAAT GGAAAAGGAA GGGAAAATTT CAAAAATTGG              2720

GCCTGAAAAT CCATACAATA CTCCAGTATT TGCCATAAAG              2760

AAAAAAGACA GTACTAAATG GAGAAAATTA GTAGATTTCA              2800

GAGAACTTAA TAAGAAAACT CAAGACTTCT GGGAAGTTCA              2840

ATTAGGAATA CCACATCCTG CAGGGTTAAA AAAGAAAAAA              2880

TCAGTAACAG TACTGGATGT GGGTGATGCA TATTTTTCAG              2920

TTCCCTTAGA TAAAGACTTC AGGAAGTATA CTGCATTTAC              2960

CATACCTAGT ATAAACAATG AAACACCAGG GATTAGATAT              3000

CAGTACAATG TGCTTCCACA GGGATGGAAA GGATCACCAG              3040

CAATATTCCA AAGTAGCATG ACAAAAATCT TAGAGCCTTT              3080

TAGAAAACAA AATCCAGACA TAGTTATCTA TCAATACATG              3120

GATGATTTGT ATGTAGGATC TGACTTAGAA ATAGGGCAGC              3160

ATAGAGCAAA AATAGAGGAA CTGAGACGAC ATCTGTTGAG              3200

GTGGGGATTT ACCACACCAG ACAAAAAACA TCAGAAAGAA              3240

CCTCCATTCC TTTGGATGGG TTATGAACTC CATCCTGATA              3280

AATGGACAGT ACAGCCTATA GTGCTGCCAG AAAAAGACAG              3320

CTGGACTGTC AATGACATAC AGAAGTTAGT GGGAAAATTG              3360

AATTGGGCAA GTCAAATTTA CGCAGGGATT AAAGTAAAGC              3400

AATTATGTAA ACTCCTTAGA GGAACCAAAG CACTAACAGA              3440

AGTAATACCA CTAACAGAAG AAGCAGAGCT AGAACTGGCA              3480

GAAAACAGGG AAATTCTAAA AGAACCAGTA CATGGAGTGT              3520

ATTATGACCC ATCAAAAGAC TTAATAGCAG AAGTACAGAA              3560

GCAGGGGCAA GGCCAATGGA CATATCAAAT TTATCAAGAG              3600

CCATTTAAAA ATCTGAAAAC AGGCAAATAT GCAAGAATGA              3640

GGGGTGCCCA CACTAATGAT GTAAAACAAT TAACAGAGGC              3680

AGTGCAAAAA ATAGCCACAG AAAGCATAGT AATATGGGGA              3720

AAGACTCCTA AATTTAGACT ACCCATACAA AAAGAAACAT              3760

GGGAAACATG GTGGACAGAG TATTGGCAAG CCACCTGGAT              3800

TCCTGAGTGG GAGTTTGTCA ATACCCCTCC CTTAGTGAAA              3840

TTATGGTACC AGTTAGAGAA AGAACCCATA GTAGGAGCAG              3880

AAACTTTCTA TGTAGATGGG GCAGCTAACA GGGAGACTAA              3920

AAAAGGAAAA GCAGGATATG TTACTAACAG AGGAAGACAA              3960

AAGGTTGTCT CCCTAACTGA CACAACAAAT CAGAAGACTG              4000

AGTTACAAGC AATTCATCTA GCTTTGCAAG ATTCAGGGTT              4040

AGAAGTAAAC ATAGTAACAG ACTCACAATA TGCATTAGGA              4080

ATCATTCAAG CACAACCAGA TAAAAGTGAA TCAGAGTTAG              4120

TCAGTCAAAT AATAGAGCAG TTAATAAAAA AGGAAAAGGT              4160
```

| | | | | |
|---|---|---|---|---|
| CTATCTGGCA | TGGGTACCAG | CACACAAAGG | AATTGGAGGA | 4200 |
| AATGAACAAG | TAGATAAATT | AGTCAGTGCT | GGAATCAGGA | 4240 |
| AAGTACTATT | TTTAGATGGA | ATAGATAAGG | CCCAAGAAGA | 4280 |
| CCATGAGAAA | TATCACAGTA | ATTGGAGAGC | AATGGCTAGT | 4320 |
| GACTTTAACC | TACCACCTAT | AGTAGCAAAA | GAAATAGTAG | 4360 |
| CCAGCTGTGA | TAAATGTCAG | CTAAAAGGAG | AAGCCATGCA | 4400 |
| TGGACAAGTA | GACTGTAGTC | CAGGAATATG | GCAACTAGAT | 4440 |
| TGTACACATT | TAGAAGGAAA | AGTTATCCTG | GTAGCAGTTC | 4480 |
| ATGTAGCCAG | TGGATACATA | GAAGCAGAAG | TTATTCCAGC | 4520 |
| AGAGACAGGG | CAGGAGACAG | CATACTTTCT | CTTAAAATTA | 4560 |
| GCAGGAAGAT | GGCCAGTAAA | AACAATACAT | ACAGACAATG | 4600 |
| GCCCCAATTT | CACCAGTACT | ACGGTTAAGG | CCGCCTGTTG | 4640 |
| GTGGGCGGGG | ATCAAGCAGG | AATTTGGCAT | TCCCTACAAT | 4680 |
| CCCCAAAGTC | AAGGAGTAAT | AGAATCTATG | AATAAAGAAT | 4720 |
| TAAAGAAAAT | TATAGGACAG | GTAAGAGATC | AGGCTGAACA | 4760 |
| TCTTAAGACA | GCAGTACAAA | TGGCAGTATT | CATCCACAAT | 4800 |
| TTTAAAAGAA | AAGGGGGGAT | TGGGGGGTAC | AGTGCAGGGG | 4840 |
| AAAGAATAGT | AGACATAATA | GCAACAGACA | TACAAACTAA | 4880 |
| AGAACTACAA | AAACAAATTA | CAAAAATTCA | AAATTTTCGG | 4920 |
| GTTTATTACA | GGGACAGCAG | AGATCCACTT | TGGAAAGGAC | 4960 |
| CAGCAAAGCT | TCTCTGGAAA | GGTGAAGGGG | CAGTAGTAAT | 5000 |
| ACAAGATAAT | AGTGACATAA | AAGTAGTGCC | AAGAAGAAAA | 5040 |
| GCAAAGATCA | TTAGGGATTA | TGGAAAACAG | ATGGCAGGTG | 5080 |
| ATGATTGTGT | GGCAAGTAGA | CAGGATGAGG | ATTAGAACAT | 5120 |
| GGAAAAGTTT | AGTAAAACAC | CATATGTATA | TTTCAAAGAA | 5160 |
| AGCTAAAGGA | TGGTTTTATA | GACATCACTA | TGAAAGCACT | 5200 |
| CATCCAAGAA | TAAGTTCAGA | AGTACACATC | CCACTAGGGG | 5240 |
| ATGCTAGATT | GGTAATAACA | ACATATTGGG | GTCTGCATAC | 5280 |
| AGGAGAAAGA | GACTGGCATT | TAGGTCAGGG | AGTCTCCATA | 5320 |
| GAATGGAGGA | AAAAGAGATA | TAGCACACAA | GTAGACCCTG | 5360 |
| ACCTAGCAGA | CCACCTAATT | CATCTGCATT | ACTTTGATTG | 5400 |
| TTTTTCAGAC | TCTGCCATAA | GAAAGGCCAT | ATTAGGACAT | 5440 |
| AGAGTTAGTC | CTATTTGTGA | ATTTCAAGCA | GGACATAACA | 5480 |
| AGGTAGGATC | TCTACAGTAC | TTGGCACTAA | CAGCATTAAT | 5520 |
| AACACCAAAA | AAGATAAAGC | CACCTTTGCC | TAGTGTTAAG | 5560 |
| AAACTGACAG | AGGATAGATG | GAACAAGCCC | CAGAAGACCA | 5600 |
| AGGGCCACAG | AGGGAGCCAT | ACAATCAATG | GCATTAGAG | 5640 |
| CTTTTAGAGG | AGCTTAAGAA | TGAAGCTGTT | AGACATTTTC | 5680 |
| CTAGGATATG | GCTCCATGGC | TTAGGGCAAC | ATATCTATGA | 5720 |
| AACTTATGGG | GATACTTGGG | CAGGAGTGGA | AGCCATAATA | 5760 |

| | |
|---|---|
| AGAATTCTAC AACAACTGCT GTTTATTCAT TTCAGAATTG | 5800 |
| GGTGTCGACA TAGCAGAATA GGCATTATTC GACAGAGGAG | 5840 |
| AGCAAGAAAT GGAGCCAGTA GATCCTAGAC TAGAGCCCTG | 5880 |
| GAAGCATCCA GGAAGTCAGC CTAAGACTGC TTGTACCACT | 5920 |
| TGCTATTGTA AAAAGTGTTG CTTTCATTGC CAAGTTTGTT | 5960 |
| TCACAAAAAA AGCCTTAGGC ATCTCCTATG GCAGGAAGAA | 6000 |
| GCGGAGACAG CGACGAAGAG CTCCTGAAGA CAGTCAGACT | 6040 |
| CATCAAGTTT CTCTACCAAA GCAGTAAGTA GTACATGTAA | 6080 |
| TGCAACCTTT AGTAATAGCA GCAATAGTAG CATTAGTAGT | 6120 |
| AGCAGGAATA ATAGCAATAG TTGTGTGATC CATAGTATTC | 6160 |
| ATAGAATATA GGAAAATAAG AAGACAAAGA AAAATAGACA | 6200 |
| GGGTAATTGA CAGAATAAGC GAAAGAGCAG AAGACAGTGG | 6240 |

```
CA ATG AGA GTG AAG GGG ATC AGG AGG AAT TAT CAG CAC                      6278
   Met Arg Val Lys Gly Ile Arg Arg Asn Tyr Gln His
    1               5                       10

TGG TGG GGA TGG GGC ACG ATG CTC CTT GGG TTA TTA                         6314
Trp Trp Gly Trp Gly Thr Met Leu Leu Gly Leu Leu
             15                  20

ATG ATC TGT AGT GCT ACA GAA AAA TTG TGG GTC ACA                         6350
Met Ile Cys Ser Ala Thr Glu Lys Leu Trp Val Thr
 25                  30                      35

GTC TAT TAT GGG GTA CCT GTG TGG AAA GAA GCA ACC                         6386
Val Tyr Tyr Gly Val Pro Val Trp Lys Glu Ala Thr
             40                  45

ACC ACT CTA TTT TGT GCA TCA GAT GCT AAA GCA TAT                         6422
Thr Thr Leu Phe Cys Ala Ser Asp Ala Lys Ala Tyr
 50                  55                      60

GAT ACA GAG GTA CAT AAT GTT TGG GCC ACA CAT GCC                         6458
Asp Thr Glu Val His Asn Val Trp Ala Thr His Ala
             65                  70

TGT GTA CCC ACA GAC CCC AAC CCA CAA GAA GTA GAA                         6494
Cys Val Pro Thr Asp Pro Asn Pro Gln Glu Val Glu
 75                  80

TTG GTA AAT GTG ACA GAA AAT TTT AAC ATG TGG AAA                         6530
Leu Val Asn Val Thr Glu Asn Phe Asn Met Trp Lys
 85                  90                      95

AAT AAC ATG GTA GAA CAG ATG CAT GAG GAT ATA ATC                         6566
Asn Asn Met Val Glu Gln Met His Glu Asp Ile Ile
             100                 105

AGT TTA TGG GAT CAA AGC CTA AAG CCA TGT GTA AAA                         6602
Ser Leu Trp Asp Gln Ser Leu Lys Pro Cys Val Lys
 110                 115                     120

TTA ACC CCA CTC TGT GTT ACT TTA AAT TGC ACT GAT                         6638
Leu Thr Pro Leu Cys Val Thr Leu Asn Cys Thr Asp
             125                 130

TTG AGG AAT ACT ACT AAT ACC AAT AAT AGT ACT GCT                         6674
Leu Arg Asn Thr Thr Asn Thr Asn Asn Ser Thr Ala
 135                 140

AAT AAC AAT AGT AAT AGC GAG GGA ACA ATA AAG GGA                         6710
Asn Asn Asn Ser Asn Ser Glu Gly Thr Ile Lys Gly
145                  150                     155

GGA GAA ATG AAA AAC TGC TCT TTC AAT ATC ACC ACA                         6746
Gly Glu Met Lys Asn Cys Ser Phe Asn Ile Thr Thr
             160                 165
```

| | | | | | | | | | | | |
|---|---|---|---|---|---|---|---|---|---|---|---|
| AGC | ATA | AGA | GAT | AAG | ATG | CAG | AAA | GAA | TAT | GCA | CTT | 6782 |
| Ser | Ile | Arg | Asp | Lys | Met | Gln | Lys | Glu | Tyr | Ala | Leu |
| 170 | | | | | 175 | | | | | | 180 |
| CTT | TAT | AAA | CTT | GAT | ATA | GTA | TCA | ATA | AAT | AAT | GAT | 6818 |
| Leu | Tyr | Lys | Leu | Asp | Ile | Val | Ser | Ile | Asn | Asn | Asp |
| | | | | 185 | | | | | 190 | | |
| AGT | ACC | AGC | TAT | AGG | TTG | ATA | AGT | TGT | AAT | ACC | TCA | 6854 |
| Ser | Thr | Ser | Tyr | Arg | Leu | Ile | Ser | Cys | Asn | Thr | Ser |
| | | 195 | | | | | 200 | | | | |
| GTC | ATT | ACA | CAA | GCT | TGT | CCA | AAG | ATA | TCC | TTT | GAG | 6890 |
| Val | Ile | Thr | Gln | Ala | Cys | Pro | Lys | Ile | Ser | Phe | Glu |
| 205 | | | | | 210 | | | | | 215 | |
| CCA | ATT | CCC | ATA | CAC | TAT | TGT | GCC | CCG | GCT | GGT | TTT | 6926 |
| Pro | Ile | Pro | Ile | His | Tyr | Cys | Ala | Pro | Ala | Gly | Phe |
| | | | 220 | | | | | 225 | | | |
| GCG | ATT | CTA | AAG | TGT | AAC | GAT | AAA | AAG | TTC | AGT | GGA | 6962 |
| Ala | Ile | Leu | Lys | Cys | Asn | Asp | Lys | Lys | Phe | Ser | Gly |
| | 230 | | | | | 235 | | | | | 240 |
| AAA | GGA | TCA | TGT | AAA | AAT | GTC | AGC | ACA | GTA | CAA | TGT | 6998 |
| Lys | Gly | Ser | Cys | Lys | Asn | Val | Ser | Thr | Val | Gln | Cys |
| | | | | 245 | | | | | 250 | | |
| ACA | CAT | GGA | ATT | AGG | CCA | GTA | GTA | TCA | ACT | CAA | CTG | 7034 |
| Thr | His | Gly | Ile | Arg | Pro | Val | Val | Ser | Thr | Gln | Leu |
| | | 255 | | | | | 260 | | | | |
| CTG | TTA | AAT | GGC | AGT | CTA | GCA | GAA | GAA | GAG | GTA | GTA | 7070 |
| Leu | Leu | Asn | Gly | Ser | Leu | Ala | Glu | Glu | Glu | Val | Val |
| 265 | | | | | 270 | | | | | 275 | |
| ATT | AGA | TCT | GAG | AAT | TTC | AAT | GAT | AAT | GCT | AAA | ACC | 7106 |
| Ile | Arg | Ser | Glu | Asn | Phe | Asn | Asp | Asn | Ala | Lys | Thr |
| | | | 280 | | | | | 285 | | | |
| ATC | ATA | GTA | CAT | CTG | AAT | GAA | TCT | GTA | CAA | ATT | AAT | 7142 |
| Ile | Ile | Val | His | Leu | Asn | Glu | Ser | Val | Gln | Ile | Asn |
| | 290 | | | | | 295 | | | | | 300 |
| TGT | ACA | AGA | CCC | AAC | TAC | AAT | AAA | AGA | AAA | AGG | ATA | 7178 |
| Cys | Thr | Arg | Pro | Asn | Tyr | Asn | Lys | Arg | Lys | Arg | Ile |
| | | | | 305 | | | | | 310 | | |
| CAT | ATA | GGA | CCA | GGG | AGA | GCA | TTT | TAT | ACA | ACA | AAA | 7214 |
| His | Ile | Gly | Pro | Gly | Arg | Ala | Phe | Tyr | Thr | Thr | Lys |
| | | 315 | | | | | 320 | | | | |
| AAT | ATA | ATA | GGA | ACT | ATA | AGA | CAA | GCA | CAT | TGT | AAC | 7250 |
| Asn | Ile | Ile | Gly | Thr | Ile | Arg | Gln | Ala | His | Cys | Asn |
| 325 | | | | | 330 | | | | | 335 | |
| ATT | AGT | AGA | GCA | AAA | TGG | AAT | GAC | ACT | TTA | AGA | CAG | 7286 |
| Ile | Ser | Arg | Ala | Lys | Trp | Asn | Asp | Thr | Leu | Arg | Gln |
| | | | 340 | | | | | 345 | | | |
| ATA | GTT | AGC | AAA | TTA | AAA | GAA | CAA | TTT | AAG | AAT | AAA | 7322 |
| Ile | Val | Ser | Lys | Leu | Lys | Glu | Gln | Phe | Lys | Asn | Lys |
| | 350 | | | | | 355 | | | | | 360 |
| ACA | ATA | GTC | TTT | AAT | CAA | TCC | TCA | GGA | GGG | GAC | CCA | 7358 |
| Thr | Ile | Val | Phe | Asn | Gln | Ser | Ser | Gly | Gly | Asp | Pro |
| | | | | 365 | | | | | 370 | | |
| GAA | ATT | GTA | ATG | CAC | AGT | TTT | AAT | TGT | GGA | GGG | GAA | 7394 |
| Glu | Ile | Val | Met | His | Ser | Phe | Asn | Cys | Gly | Gly | Glu |
| | | 375 | | | | | 380 | | | | |
| TTT | TTC | TAC | TGT | AAT | ACA | TCA | CCA | CTG | TTT | AAT | AGT | 7430 |
| Phe | Phe | Tyr | Cys | Asn | Thr | Ser | Pro | Leu | Phe | Asn | Ser |
| 385 | | | | | 390 | | | | | 395 | |
| ACT | TGG | AAT | GGT | AAT | AAT | ACT | TGG | AAT | AAT | ACT | ACA | 7466 |
| Thr | Trp | Asn | Gly | Asn | Asn | Thr | Trp | Asn | Asn | Thr | Thr |
| | | | 400 | | | | | 405 | | | |

| | | | | | | | | | | |
|---|---|---|---|---|---|---|---|---|---|---|
| GGG | TCA | AAT | AAC | AAT | ATC | ACA | CTT | CAA | TGC | AAA | ATA | 7502 |
| Gly | Ser | Asn | Asn | Asn | Ile | Thr | Leu | Gln | Cys | Lys | Ile |
| | 410 | | | | 415 | | | | | 420 |
| AAA | CAA | ATT | ATA | AAC | ATG | TGG | CAG | GAA | GTA | GGA | AAA | 7538 |
| Lys | Gln | Ile | Ile | Asn | Met | Trp | Gln | Glu | Val | Gly | Lys |
| | | | 425 | | | | | 430 |
| GCA | ATA | TAT | GCC | CCT | CCC | ATT | GAA | GGA | CAA | ATT | AGA | 7574 |
| Ala | Ile | Tyr | Ala | Pro | Pro | Ile | Glu | Gly | Gln | Ile | Arg |
| | | 435 | | | | | 440 |
| TGT | TCA | TCA | AAT | ATT | ACA | GGG | CTA | CTA | TTA | ACA | AGA | 7610 |
| Cys | Ser | Ser | Asn | Ile | Thr | Gly | Leu | Leu | Leu | Thr | Arg |
| 445 | | | | | 450 | | | | | 455 |
| GAT | GGT | GGT | AAG | GAC | ACG | GAC | ACG | AAC | GAC | ACC | GAG | 7646 |
| Asp | Gly | Gly | Lys | Asp | Thr | Asp | Thr | Asn | Asp | Thr | Glu |
| | | | 460 | | | | | 465 |
| ATC | TTC | AGA | CCT | GGA | GGA | GGA | GAT | ATG | AGG | GAC | AAT | 7682 |
| Ile | Phe | Arg | Pro | Gly | Gly | Gly | Asp | Met | Arg | Asp | Asn |
| | 470 | | | | | 475 | | | | | 480 |
| TGG | AGA | AGT | GAA | TTA | TAT | AAA | TAT | AAA | GTA | GTA | ACA | 7718 |
| Trp | Arg | Ser | Glu | Leu | Tyr | Lys | Tyr | Lys | Val | Val | Thr |
| | | | | 485 | | | | | 490 |
| ATT | GAA | CCA | TTA | GGA | GTA | GCA | CCC | ACC | AAG | GCA | AAG | 7754 |
| Ile | Glu | Pro | Leu | Gly | Val | Ala | Pro | Thr | Lys | Ala | Lys |
| | | 495 | | | | | 500 |
| AGA | AGA | GTG | GTG | CAG | AGA | GAA | AAA | AGA | GCA | GCG | ATA | 7790 |
| Arg | Arg | Val | Val | Gln | Arg | Glu | Lys | Arg | Ala | Ala | Ile |
| 505 | | | | | 510 | | | | | 515 |
| GGA | GCT | CTG | TTC | CTT | GGG | TTC | TTA | GGA | GCA | GCA | GGA | 7826 |
| Gly | Ala | Leu | Phe | Leu | Gly | Phe | Leu | Gly | Ala | Ala | Gly |
| | | | 520 | | | | | 525 |
| AGC | ACT | ATG | GGC | GCA | GCG | TCA | GTG | ACG | CTG | ACG | GTA | 7862 |
| Ser | Thr | Met | Gly | Ala | Ala | Ser | Val | Thr | Leu | Thr | Val |
| | | 530 | | | | | 535 | | | | 540 |
| CAG | GCC | AGA | CTA | TTA | TTG | TCT | GGT | ATA | GTG | CAA | CAG | 7898 |
| Gln | Ala | Arg | Leu | Leu | Leu | Ser | Gly | Ile | Val | Gln | Gln |
| | | | | 545 | | | | | 550 |
| CAG | AAC | AAT | TTG | CTG | AGG | GCC | ATT | GAG | GCG | CAA | CAG | 7934 |
| Gln | Asn | Asn | Leu | Leu | Arg | Ala | Ile | Glu | Ala | Gln | Gln |
| | | 555 | | | | | 560 |
| CAT | ATG | TTG | CAA | CTC | ACA | GTC | TGG | GGC | ATC | AAG | CAG | 7970 |
| His | Met | Leu | Gln | Leu | Thr | Val | Trp | Gly | Ile | Lys | Gln |
| 565 | | | | | 570 | | | | | 575 |
| CTC | CAG | GCA | AGA | ATC | CTG | GCT | GTG | GAA | AGA | TAC | CTA | 8006 |
| Leu | Gln | Ala | Arg | Ile | Leu | Ala | Val | Glu | Arg | Tyr | Leu |
| | | | 580 | | | | | 585 |
| AAG | GAT | CAA | CAG | CTC | CTG | GGG | ATT | TGG | GGT | TGC | TCT | 8042 |
| Lys | Asp | Gln | Gln | Leu | Leu | Gly | Ile | Trp | Gly | Cys | Ser |
| | | 590 | | | | | 595 | | | | 600 |
| GGA | AAA | CTC | ATT | TGC | ACC | ACT | ACT | GTG | CCT | TGG | AAT | 8078 |
| Gly | Lys | Leu | Ile | Cys | Thr | Thr | Thr | Val | Pro | Trp | Asn |
| | | | | 605 | | | | | 610 |
| GCT | AGT | TGG | AGT | AAT | AAA | TCT | CTG | GAT | GAT | ATT | TGG | 8114 |
| Ala | Ser | Trp | Ser | Asn | Lys | Ser | Leu | Asp | Asp | Ile | Trp |
| | | | 615 | | | | | 620 |
| AAT | AAC | ATG | ACC | TGG | ATG | CAG | TGG | GAA | AGA | GAA | ATT | 8150 |
| Asn | Asn | Met | Thr | Trp | Met | Gln | Trp | Glu | Arg | Glu | Ile |
| 625 | | | | | 630 | | | | | 635 |
| GAC | AAT | TAC | ACA | AGC | TTA | ATA | TAC | TCA | TTA | CTA | GAA | 8186 |
| Asp | Asn | Tyr | Thr | Ser | Leu | Ile | Tyr | Ser | Leu | Leu | Glu |
| | | | | 640 | | | | | 645 |

| | | | | | | | | | | | |
|---|---|---|---|---|---|---|---|---|---|---|---|
| AAA | TCG | CAA | ACC | CAA | CAA | GAA | ATG | AAT | GAA | CAA | GAA |
| Lys | Ser | Gln | Thr | Gln | Gln | Glu | Met | Asn | Glu | Gln | Glu |
| 650 | | | | 655 | | | | | 660 | | |

8222

| TTA | TTG | GAA | TTG | GAT | AAA | TGG | GCA | AGT | TTG | TGG | AAT |
|---|---|---|---|---|---|---|---|---|---|---|---|
| Leu | Leu | Glu | Leu | Asp | Lys | Trp | Ala | Ser | Leu | Trp | Asn |
| | | | | 665 | | | | | 670 | | |

8258

| TGG | TTT | GAC | ATA | ACA | AAT | TGG | CTG | TGG | TAT | ATA | AAA |
|---|---|---|---|---|---|---|---|---|---|---|---|
| Trp | Phe | Asp | Ile | Thr | Asn | Trp | Leu | Trp | Tyr | Ile | Lys |
| | | 675 | | | | | 680 | | | | |

8294

| ATA | TTC | ATA | ATG | ATA | GTA | GGA | GGC | TTG | GTA | GGT | TTA |
|---|---|---|---|---|---|---|---|---|---|---|---|
| Ile | Phe | Ile | Met | Ile | Val | Gly | Gly | Leu | Val | Gly | Leu |
| 685 | | | | | 690 | | | | | 695 | |

8330

| AGA | ATA | GTT | TTT | GCT | GTA | CTT | TCT | ATA | GTG | AAT | AGA |
|---|---|---|---|---|---|---|---|---|---|---|---|
| Arg | Ile | Val | Phe | Ala | Val | Leu | Ser | Ile | Val | Asn | Arg |
| | | | 700 | | | | | 705 | | | |

8366

| GTT | AGG | CAG | GGA | TAC | TCA | CCA | TTG | TCG | TTG | CAG | ACC |
|---|---|---|---|---|---|---|---|---|---|---|---|
| Val | Arg | Gln | Gly | Tyr | Ser | Pro | Leu | Ser | Leu | Gln | Thr |
| | 710 | | | | | 715 | | | | | 720 |

8402

| CGC | CCC | CCA | GTT | CCG | AGG | GGA | CCC | GAC | AGG | CCC | GAA |
|---|---|---|---|---|---|---|---|---|---|---|---|
| Arg | Pro | Pro | Val | Pro | Arg | Gly | Pro | Asp | Arg | Pro | Glu |
| | | | | 725 | | | | | 730 | | |

8438

| GGA | ATC | GAA | GAA | GAA | GGT | GGA | GAG | AGA | GAC | AGA | GAC |
|---|---|---|---|---|---|---|---|---|---|---|---|
| Gly | Ile | Glu | Glu | Glu | Gly | Gly | Glu | Arg | Asp | Arg | Asp |
| | | | 735 | | | | | 740 | | | |

8474

| ACA | TCC | GGT | CGA | TTA | GTG | CAT | GGA | TTC | TTA | GCA | ATT |
|---|---|---|---|---|---|---|---|---|---|---|---|
| Thr | Ser | Gly | Arg | Leu | Val | His | Gly | Phe | Leu | Ala | Ile |
| 745 | | | | | 750 | | | | | 755 | |

8510

| ATC | TGG | GTC | GAC | CTG | CGG | AGC | CTG | TTC | CTC | TTC | AGC |
|---|---|---|---|---|---|---|---|---|---|---|---|
| Ile | Trp | Val | Asp | Leu | Arg | Ser | Leu | Phe | Leu | Phe | Ser |
| | | | 760 | | | | | 765 | | | |

8546

| TAC | CAC | CAC | TTG | AGA | GAC | TTA | CTC | TTG | ATT | GCA | GCG |
|---|---|---|---|---|---|---|---|---|---|---|---|
| Tyr | His | His | Leu | Arg | Asp | Leu | Leu | Leu | Ile | Ala | Ala |
| | 770 | | | | | 775 | | | | | 780 |

8582

| AGG | ATT | GTG | GAA | CTT | CTG | GGA | CGC | AGG | GGG | TGG | GAA |
|---|---|---|---|---|---|---|---|---|---|---|---|
| Arg | Ile | Val | Glu | Leu | Leu | Gly | Arg | Arg | Gly | Trp | Glu |
| | | | | 785 | | | | | 790 | | |

8618

| GTC | CTC | AAA | TAT | TGG | TGG | AAT | CTC | CTA | CAG | TAT | TGG |
|---|---|---|---|---|---|---|---|---|---|---|---|
| Val | Leu | Lys | Tyr | Trp | Trp | Asn | Leu | Leu | Gln | Tyr | Trp |
| | | 795 | | | | | 800 | | | | |

8654

| AGT | CAG | GAA | CTA | AAG | AGT | AGT | GCT | GTT | AGC | TTG | CTT |
|---|---|---|---|---|---|---|---|---|---|---|---|
| Ser | Gln | Glu | Leu | Lys | Ser | Ser | Ala | Val | Ser | Leu | Leu |
| 805 | | | | | 810 | | | | | 815 | |

8690

| AAT | GCC | ACA | GAT | ATA | GCA | GTA | GCT | GAG | GGG | ACA | GAT |
|---|---|---|---|---|---|---|---|---|---|---|---|
| Asn | Ala | Thr | Asp | Ile | Ala | Val | Ala | Glu | Gly | Thr | Asp |
| | | | 820 | | | | | 825 | | | |

8726

| AGG | GTT | ATA | GAA | GTA | CTG | CAA | AGA | GCT | GGT | AGA | GCT |
|---|---|---|---|---|---|---|---|---|---|---|---|
| Arg | Val | Ile | Glu | Val | Leu | Gln | Arg | Ala | Gly | Arg | Ala |
| | 830 | | | | | 835 | | | | | 840 |

8762

| ATT | CTC | CAC | ATA | CCT | ACA | AGA | ATA | AGA | CAG | GGC | TTG |
|---|---|---|---|---|---|---|---|---|---|---|---|
| Ile | Leu | His | Ile | Pro | Thr | Arg | Ile | Arg | Gln | Gly | Leu |
| | | | | 845 | | | | | 850 | | |

8798

| GAA | AGG | GCT | TTG | CTA |
|---|---|---|---|---|
| Glu | Arg | Ala | Leu | Leu |
| | | 855 | | |

8813

TAAGATGGGT GGCAAATGGT CAAAACGTGT GACTGGATGG                8853

CCTACTGTAA GGGAAAAAAT GAGACGAGCT GAACCAGCTG                8893

AGCCAGCAGC AGATGGGGTG GGAGCAGCAT CCCGAGACCT                8933

GGAAAAACAT GGAGCACTCA CAAGTAGCAA TACAGCAGCT                8973

| | | | | |
|---|---|---|---|---|
| ACCAATGCTG | ATTGTGCCTG | GCTAGAAGCA | CAAGAGGAGG | 9013 |
| AGGAAGTGGG | TTTTCCAGTC | AGACCTCAGG | TACCTTTAAG | 9053 |
| ACCAATGACT | TACAAAGCAG | CTTTAGATCT | TAGCCACTTT | 9093 |
| TTAAAAGAAA | AGGGGGGACT | GGATGGGTTA | ATTTACTCCC | 9133 |
| AAAAGAGACA | AGACATCCTT | GATCTGTGGG | TCTACCACAC | 9173 |
| ACAAGGCTAC | TTCCCTGATT | GGCAGAACTA | CACACCAGGG | 9213 |
| CCAGGGATCA | GATATCCACT | GACCTTTGGA | TGGTGCTTCA | 9253 |
| AGCTAGTACC | AGTTGAGCCA | GAGAAGATAG | AAGAGGCCAA | 9293 |
| TAAAGGAGAG | AACAACTGCT | TGTTACACCC | TATGAGCCAG | 9333 |
| CATGGGATGG | ATGACCCGGA | GAGAGAAGTG | TTAGTGTGGA | 9373 |
| AGTCTGACAG | CCACCTAGCA | TTTCAGCATT | ATGCCCGAGA | 9413 |
| GCTGCATCCG | GAGTACTACA | AGAACTGCTG | ACATCGAGCT | 9453 |
| ATCTACAAGG | GACTTTCCGC | TGGGGACTTT | CCAGGGAGGT | 9493 |
| GTGGCCTGGG | CGGGACCGGG | GAGTGGCGAG | CCCTCAGATG | 9533 |
| CTGCATATAA | GCAGCTGCTT | TCTGCCTGTA | CTGGGTCTCT | 9573 |
| CTGGTTAGAC | CAGATCTGAG | CCTGGGAGCT | CTCTGGCTAA | 9613 |
| CTAGGGAACC | CACTGCTTAA | GCCTCAATAA | AGCTTGCCTT | 9653 |
| GAGTGCTTCA | AGTAGTGTGT | GCCCGTCTGT | TATGTGACTC | 9693 |
| TGGTAGCTAG | AGATCCCTCA | GATCCTTTTA | GGCAGTGTGG | 9733 |
| AAAATCTCTA | GCA | | | 9746 |

( 2 ) INFORMATION FOR SEQ ID NO:4:

( i ) SEQUENCE CHARACTERISTICS:
        ( A ) LENGTH: 857 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Arg Val Lys Gly Ile Arg Arg Asn Tyr Gln His
 1               5                   10

Trp Trp Gly Trp Gly Thr Met Leu Leu Gly Leu Leu
             15                  20

Met Ile Cys Ser Ala Thr Glu Lys Leu Trp Val Thr
 25                  30                  35

Val Tyr Tyr Gly Val Pro Val Trp Lys Glu Ala Thr
             40                  45

Thr Thr Leu Phe Cys Ala Ser Asp Ala Lys Ala Tyr
     50                  55                  60

Asp Thr Glu Val His Asn Val Trp Ala Thr His Ala
                 65                  70

Cys Val Pro Thr Asp Pro Asn Pro Gln Glu Val Glu
             75                  80

Leu Val Asn Val Thr Glu Asn Phe Asn Met Trp Lys
 85                  90                  95

Asn Asn Met Val Glu Gln Met His Glu Asp Ile Ile
             100                 105
```

-continued

| | | | | | | | | | | |
|---|---|---|---|---|---|---|---|---|---|---|
| Ser | Leu | Trp | Asp | Gln | Ser | Leu | Lys | Pro | Cys | Val | Lys |
| | 110 | | | | 115 | | | | | 120 |
| Leu | Thr | Pro | Leu | Cys | Val | Thr | Leu | Asn | Cys | Thr | Asp |
| | | | | 125 | | | | | 130 | |
| Leu | Arg | Asn | Thr | Thr | Asn | Thr | Asn | Asn | Ser | Thr | Ala |
| | | 135 | | | | 140 | | | | |
| Asn | Asn | Asn | Ser | Asn | Ser | Glu | Gly | Thr | Ile | Lys | Gly |
| 145 | | | | | 150 | | | | | 155 | |
| Gly | Glu | Met | Lys | Asn | Cys | Ser | Phe | Asn | Ile | Thr | Thr |
| | | | 160 | | | | | 165 | | | |
| Ser | Ile | Arg | Asp | Lys | Met | Gln | Lys | Glu | Tyr | Ala | Leu |
| | 170 | | | | | 175 | | | | | 180 |
| Leu | Tyr | Lys | Leu | Asp | Ile | Val | Ser | Ile | Asn | Asn | Asp |
| | | | | 185 | | | | 190 | | | |
| Ser | Thr | Ser | Tyr | Arg | Leu | Ile | Ser | Cys | Asn | Thr | Ser |
| | | 195 | | | | | 200 | | | | |
| Val | Ile | Thr | Gln | Ala | Cys | Pro | Lys | Ile | Ser | Phe | Glu |
| 205 | | | | | 210 | | | | | 215 | |
| Pro | Ile | Pro | Ile | His | Tyr | Cys | Ala | Pro | Ala | Gly | Phe |
| | | | 220 | | | | | 225 | | | |
| Ala | Ile | Leu | Lys | Cys | Asn | Asp | Lys | Lys | Phe | Ser | Gly |
| | 230 | | | | | 235 | | | | | 240 |
| Lys | Gly | Ser | Cys | Lys | Asn | Val | Ser | Thr | Val | Gln | Cys |
| | | | | 245 | | | | | 250 | | |
| Thr | His | Gly | Ile | Arg | Pro | Val | Val | Ser | Thr | Gln | Leu |
| | | 255 | | | | | 260 | | | | |
| Leu | Leu | Asn | Gly | Ser | Leu | Ala | Glu | Glu | Val | Val |
| 265 | | | | | 270 | | | | | 275 | |
| Ile | Arg | Ser | Glu | Asn | Phe | Asn | Asp | Asn | Ala | Lys | Thr |
| | | | 280 | | | | | 285 | | | |
| Ile | Ile | Val | His | Leu | Asn | Glu | Ser | Val | Gln | Ile | Asn |
| | 290 | | | | | 295 | | | | | 300 |
| Cys | Thr | Arg | Pro | Asn | Tyr | Asn | Lys | Arg | Lys | Arg | Ile |
| | | | | 305 | | | | | 310 | | |
| His | Ile | Gly | Pro | Gly | Arg | Ala | Phe | Tyr | Thr | Thr | Lys |
| | | 315 | | | | | 320 | | | | |
| Asn | Ile | Ile | Gly | Thr | Ile | Arg | Gln | Ala | His | Cys | Asn |
| 325 | | | | | 330 | | | | | 335 | |
| Ile | Ser | Arg | Ala | Lys | Trp | Asn | Asp | Thr | Leu | Arg | Gln |
| | | | 340 | | | | | 345 | | | |
| Ile | Val | Ser | Lys | Leu | Lys | Glu | Gln | Phe | Lys | Asn | Lys |
| | 350 | | | | | 355 | | | | | 360 |
| Thr | Ile | Val | Phe | Asn | Gln | Ser | Ser | Gly | Gly | Asp | Pro |
| | | | | 365 | | | | | 370 | | |
| Glu | Ile | Val | Met | His | Ser | Phe | Asn | Cys | Gly | Gly | Glu |
| | | | 375 | | | | | 380 | | | |
| Phe | Phe | Tyr | Cys | Asn | Thr | Ser | Pro | Leu | Phe | Asn | Ser |
| 385 | | | | | 390 | | | | | 395 | |
| Thr | Trp | Asn | Gly | Asn | Asn | Thr | Trp | Asn | Asn | Thr | Thr |
| | | | 400 | | | | | 405 | | | |
| Gly | Ser | Asn | Asn | Asn | Ile | Thr | Leu | Gln | Cys | Lys | Ile |
| | 410 | | | | | 415 | | | | | 420 |
| Lys | Gln | Ile | Ile | Asn | Met | Trp | Gln | Glu | Val | Gly | Lys |
| | | | | 425 | | | | | 430 | | |

```
Ala  Ile  Tyr  Ala  Pro  Pro  Ile  Glu  Gly  Gln  Ile  Arg
          435                 440

Cys  Ser  Ser  Asn  Ile  Thr  Gly  Leu  Leu  Leu  Thr  Arg
445                 450                           455

Asp  Gly  Gly  Lys  Asp  Thr  Asp  Thr  Asn  Asp  Thr  Glu
               460                      465

Ile  Phe  Arg  Pro  Gly  Gly  Gly  Asp  Met  Arg  Asp  Asn
     470                 475                           480

Trp  Arg  Ser  Glu  Leu  Tyr  Lys  Tyr  Lys  Val  Val  Thr
                    485                 490

Ile  Glu  Pro  Leu  Gly  Val  Ala  Pro  Thr  Lys  Ala  Lys
          495                 500

Arg  Arg  Val  Val  Gln  Arg  Glu  Lys  Arg  Ala  Ala  Ile
505                      510                           515

Gly  Ala  Leu  Phe  Leu  Gly  Phe  Leu  Gly  Ala  Ala  Gly
               520                      525

Ser  Thr  Met  Gly  Ala  Ala  Ser  Val  Thr  Leu  Thr  Val
     530                 535                           540

Gln  Ala  Arg  Leu  Leu  Leu  Ser  Gly  Ile  Val  Gln  Gln
                    545                 550

Gln  Asn  Asn  Leu  Leu  Arg  Ala  Ile  Glu  Ala  Gln  Gln
               555                 560

His  Met  Leu  Gln  Leu  Thr  Val  Trp  Gly  Ile  Lys  Gln
565                      570                 575

Leu  Gln  Ala  Arg  Ile  Leu  Ala  Val  Glu  Arg  Tyr  Leu
               580                 585

Lys  Asp  Gln  Gln  Leu  Leu  Gly  Ile  Trp  Gly  Cys  Ser
     590                      595                      600

Gly  Lys  Leu  Ile  Cys  Thr  Thr  Val  Pro  Trp  Asn
                    605                 610

Ala  Ser  Trp  Ser  Asn  Lys  Ser  Leu  Asp  Asp  Ile  Trp
          615                 620

Asn  Asn  Met  Thr  Trp  Met  Gln  Trp  Glu  Arg  Glu  Ile
625                      630                           635

Asp  Asn  Tyr  Thr  Ser  Leu  Ile  Tyr  Ser  Leu  Leu  Glu
               640                 645

Lys  Ser  Gln  Thr  Gln  Gln  Glu  Met  Asn  Glu  Gln  Glu
     650                      655                      660

Leu  Leu  Glu  Leu  Asp  Lys  Trp  Ala  Ser  Leu  Trp  Asn
               665                      670

Trp  Phe  Asp  Ile  Thr  Asn  Trp  Leu  Trp  Tyr  Ile  Lys
          675                      680

Ile  Phe  Ile  Met  Ile  Val  Gly  Gly  Leu  Val  Gly  Leu
685                      690                           695

Arg  Ile  Val  Phe  Ala  Val  Leu  Ser  Ile  Val  Asn  Arg
               700                      705

Val  Arg  Gln  Gly  Tyr  Ser  Pro  Leu  Ser  Leu  Gln  Thr
     710                      715                      720

Arg  Pro  Pro  Val  Pro  Arg  Gly  Pro  Asp  Arg  Pro  Glu
                    725                      730

Gly  Ile  Glu  Glu  Glu  Gly  Gly  Glu  Arg  Asp  Arg  Asp
               735                      740

Thr  Ser  Gly  Arg  Leu  Val  His  Gly  Phe  Leu  Ala  Ile
```

| | | | | | | | | | |
|---|---|---|---|---|---|---|---|---|---|
745| | | |750| | | |755| |
Ile|Trp|Val|Asp|Leu|Arg|Ser|Leu|Phe|Leu|Phe|Ser
| | |760| | | |765| | |
Tyr|His|His|Leu|Arg|Asp|Leu|Leu|Ile|Ala|Ala
| |770| | | |775| | | |780
Arg|Ile|Val|Glu|Leu|Leu|Gly|Arg|Arg|Gly|Trp|Glu
| | | |785| | | |790| |
Val|Leu|Lys|Tyr|Trp|Trp|Asn|Leu|Leu|Gln|Tyr|Trp
| | |795| | | |800| | |
Ser|Gln|Glu|Leu|Lys|Ser|Ser|Ala|Val|Ser|Leu|Leu
805| | | |810| | | |815| |
Asn|Ala|Thr|Asp|Ile|Ala|Val|Ala|Glu|Gly|Thr|Asp
| | |820| | | |825| | |
Arg|Val|Ile|Glu|Val|Leu|Gln|Arg|Ala|Gly|Arg|Ala
| |830| | | |835| | | |840
Ile|Leu|His|Ile|Pro|Thr|Arg|Ile|Arg|Gln|Gly|Leu
| | | |845| | | |850| |
Glu|Arg|Ala|Leu|Leu
| | |855| |

( 2 ) INFORMATION FOR SEQ ID NO:5:

( i ) SEQUENCE CHARACTERISTICS:
        ( A ) LENGTH: 3807 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 648..3215

( x i ) SEQUENCE DESCRIPTION: SEQ ID NO:5:

| | | | | |
|---|---|---|---|---|
| GATCAAGGGC | CACAGAGGGA | GCCACACAAT | GAATGGACAC | 40 |
| TAGAGCTTTT | AGAGGAGCTT | AAGAGTGAAG | CTGTTAGACA | 80 |
| CTTTCCTAGG | ATATGGCTTC | ATGGCTTAGG | GCAACATATC | 120 |
| TATGAAACTT | ATGGGGATAC | TTGGGCAGGA | GTGGAAGCCA | 160 |
| TAATAAGAAT | TCTGCAACAA | CTGCTGTTTA | TCCATTTCAG | 200 |
| GATTGGGTGC | CAACATAGCA | GAATAGGTAT | TATTCAACAG | 240 |
| AGGAGAGCAA | GAAATGGAGC | CAGTAGATCC | TAAACTAGAG | 280 |
| CCCTGGAAGC | ATCCAGGAAG | TCAGCCTAAG | ACTGCTTGTA | 320 |
| CCACTTGCTA | TTGTAAAAAG | TGTTGCTTTC | ATTGCCAAGT | 360 |
| TTGCTTCATA | ACAAAAGGCT | TAGGCATCTC | CTATGGCAGG | 400 |
| AAGAAGCGGA | GACAGCGACG | AAGAGCTCCT | CAAGACAGTG | 440 |
| AGACTCATCA | AGTTTCTCTA | TCAAAGCAGT | AAGTAGTACA | 480 |
| TGTAATGCAA | GCTTTACAAA | TATCAGCTAT | AGTAGGATTA | 520 |
| GTAGTAGCAG | CAATAATAGC | AATAGTTGTG | TGGACCATAG | 560 |
| TATTCATAGA | ATATAGGAAA | ATATTAAGGC | AAAGAAAAAT | 600 |
| AGACAGGTTA | ATTGATAGAA | TAACAGAAAG | AGCAGAAGAC | 640 |

| | | | | | | | | | | |
|---|---|---|---|---|---|---|---|---|---|---|
|AGTGGCA|ATG|AGA|GTG|ACG|GAG|ATC|AGG|AAG|AGT|TAT|CAG|CAC|683|
| |Met|Arg|Val|Thr|Glu|Ile|Arg|Lys|Ser|Tyr|Gln|His| |
| |1| | |5| | | | |10| | | |

| | | | | | | | | | | | |
|---|---|---|---|---|---|---|---|---|---|---|---|
| TGG | TGG | AGA | TGG | GGC | ATC | ATG | CTC | CTT | GGG | ATA | TTA | 719 |
| Trp | Trp | Arg | Trp | Gly | Ile | Met | Leu | Leu | Gly | Ile | Leu | |
| | | 15 | | | | 20 | | | | | | |
| ATG | ATC | TGT | AAT | GCT | GAA | GAA | AAA | TTG | TGG | GTC | ACA | 755 |
| Met | Ile | Cys | Asn | Ala | Glu | Glu | Lys | Leu | Trp | Val | Thr | |
| 25 | | | | | 30 | | | | | 35 | | |
| GTC | TAT | TAT | GGG | GTA | CCT | GTG | TGG | AAA | GAA | GCA | ACC | 791 |
| Val | Tyr | Tyr | Gly | Val | Pro | Val | Trp | Lys | Glu | Ala | Thr | |
| | | | 40 | | | | | 45 | | | | |
| ACC | ACT | CTA | TTT | TGT | GCA | TCA | GAT | CGT | AAA | GCA | TAT | 827 |
| Thr | Thr | Leu | Phe | Cys | Ala | Ser | Asp | Arg | Lys | Ala | Tyr | |
| | | 50 | | | | 55 | | | | | 60 | |
| GAT | ACA | GAG | GTA | CAT | AAT | GTT | TGG | GCC | ACA | CAT | GCC | 863 |
| Asp | Thr | Glu | Val | His | Asn | Val | Trp | Ala | Thr | His | Ala | |
| | | | | 65 | | | | | | 70 | | |
| TGT | GTA | CCC | ACA | GAC | CCC | AAC | CCA | CAA | GAA | GTA | GAA | 899 |
| Cys | Val | Pro | Thr | Asp | Pro | Asn | Pro | Gln | Glu | Val | Glu | |
| | | 75 | | | | 80 | | | | | | |
| TTG | AAA | AAT | GTG | ACA | GAA | AAT | TTT | AAC | ATG | TGG | AAA | 935 |
| Leu | Lys | Asn | Val | Thr | Glu | Asn | Phe | Asn | Met | Trp | Lys | |
| 85 | | | | | 90 | | | | | 95 | | |
| AAT | AAC | ATG | GTA | GAA | CAA | ATG | CAT | GAG | GAT | ATA | ATC | 971 |
| Asn | Asn | Met | Val | Glu | Gln | Met | His | Glu | Asp | Ile | Ile | |
| | | | 100 | | | | | 105 | | | | |
| AGT | TTA | TGG | GAT | CAA | AGC | CTA | AAG | CCA | TGT | GTA | AAA | 1007 |
| Ser | Leu | Trp | Asp | Gln | Ser | Leu | Lys | Pro | Cys | Val | Lys | |
| | 110 | | | | | 115 | | | | | 120 | |
| TTA | ACC | CCA | CTC | TGT | GTT | ACT | TTA | AAT | TGC | ACT | GAT | 1043 |
| Leu | Thr | Pro | Leu | Cys | Val | Thr | Leu | Asn | Cys | Thr | Asp | |
| | | | | 125 | | | | | 130 | | | |
| TTG | AGG | AAT | GCT | ACT | AAT | GGG | AAT | GAC | ACT | AAT | ACC | 1079 |
| Leu | Arg | Asn | Ala | Thr | Asn | Gly | Asn | Asp | Thr | Asn | Thr | |
| | | 135 | | | | | 140 | | | | | |
| ACT | AGT | AGT | AGC | AGG | GGA | ATG | GTG | GGG | GGA | GGA | GAA | 1115 |
| Thr | Ser | Ser | Ser | Arg | Gly | Met | Val | Gly | Gly | Gly | Glu | |
| 145 | | | | | 150 | | | | | 155 | | |
| ATG | AAA | AAT | TGC | TCT | TTC | AAT | ATC | ACC | ACA | AAC | ATA | 1151 |
| Met | Lys | Asn | Cys | Ser | Phe | Asn | Ile | Thr | Thr | Asn | Ile | |
| | | | 160 | | | | | 165 | | | | |
| AGA | GGT | AAG | GTG | CAG | AAA | GAA | TAT | GCA | CTT | TTT | TAT | 1187 |
| Arg | Gly | Lys | Val | Gln | Lys | Glu | Tyr | Ala | Leu | Phe | Tyr | |
| | 170 | | | | | 175 | | | | | 180 | |
| AAA | CTT | GAT | ATA | GCA | CCA | ATA | GAT | AAT | AAT | AGT | AAT | 1223 |
| Lys | Leu | Asp | Ile | Ala | Pro | Ile | Asp | Asn | Asn | Ser | Asn | |
| | | | | 185 | | | | | 190 | | | |
| AAT | AGA | TAT | AGG | TTG | ATA | AGT | TGT | AAC | ACC | TCA | GTC | 1259 |
| Asn | Arg | Tyr | Arg | Leu | Ile | Ser | Cys | Asn | Thr | Ser | Val | |
| | | 195 | | | | | 200 | | | | | |
| ATT | ACA | CAG | GCC | TGT | CCA | AAG | GTA | TCC | TTT | GAG | CCA | 1295 |
| Ile | Thr | Gln | Ala | Cys | Pro | Lys | Val | Ser | Phe | Glu | Pro | |
| 205 | | | | | 210 | | | | | 215 | | |
| ATT | CCC | ATA | CAT | TAT | TGT | GCC | CCG | GCT | GGT | TTT | GCG | 1331 |
| Ile | Pro | Ile | His | Tyr | Cys | Ala | Pro | Ala | Gly | Phe | Ala | |
| | | | 220 | | | | | 225 | | | | |
| ATT | CTA | AAG | TGT | AAA | GAT | AAG | AAG | TTC | AAT | GGA | AAA | 1367 |
| Ile | Leu | Lys | Cys | Lys | Asp | Lys | Lys | Phe | Asn | Gly | Lys | |
| | 230 | | | | | 235 | | | | | 240 | |
| GGA | CCA | TGT | ACA | AAT | GTC | AGC | ACA | GTA | CAA | TGT | ACA | 1403 |
| Gly | Pro | Cys | Thr | Asn | Val | Ser | Thr | Val | Gln | Cys | Thr | |
| | | | | 245 | | | | | 250 | | | |

| | | | | | | | | | | | |
|---|---|---|---|---|---|---|---|---|---|---|---|
| CAT | GGA | ATT | AGG | CCA | GTA | GTA | TCA | ACT | CAA | CTG | CTG | 1439 |
| His | Gly | Ile | Arg | Pro | Val | Val | Ser | Thr | Gln | Leu | Leu | |
| | | 255 | | | | 260 | | | | | | |

| TTA | AAT | GGC | AGT | CTA | GCA | GAA | GAA | GAG | GTA | GTA | ATT | 1475 |
| Leu | Asn | Gly | Ser | Leu | Ala | Glu | Glu | Glu | Val | Val | Ile | |
| 265 | | | | | 270 | | | | | 275 | | |

| AGA | TCC | GCC | AAT | TTC | GCG | GAC | AAT | GCT | AAA | GTC | ATA | 1511 |
| Arg | Ser | Ala | Asn | Phe | Ala | Asp | Asn | Ala | Lys | Val | Ile | |
| | | | 280 | | | | | 285 | | | | |

| ATA | GTA | CAG | CTG | AAT | GAA | TCT | GTA | GAA | ATT | AAT | TGT | 1547 |
| Ile | Val | Gln | Leu | Asn | Glu | Ser | Val | Glu | Ile | Asn | Cys | |
| 290 | | | | | 295 | | | | | 300 | | |

| ACA | AGA | CCC | AAC | AAC | AAT | ACA | AGA | AAA | AGT | ATA | CAT | 1583 |
| Thr | Arg | Pro | Asn | Asn | Asn | Thr | Arg | Lys | Ser | Ile | His | |
| | | | 305 | | | | | 310 | | | | |

| ATA | GGA | CCA | GGC | AGA | GCA | TTT | TAT | ACA | ACA | GGA | GAA | 1619 |
| Ile | Gly | Pro | Gly | Arg | Ala | Phe | Tyr | Thr | Thr | Gly | Glu | |
| | | | 315 | | | | 320 | | | | | |

| ATA | ATA | GGA | GAT | ATA | AGA | CAA | GCA | CAT | TGT | AAC | CTT | 1655 |
| Ile | Ile | Gly | Asp | Ile | Arg | Gln | Ala | His | Cys | Asn | Leu | |
| 325 | | | | 330 | | | | | 335 | | | |

| AGT | AGA | GCA | AAA | TGG | AAT | GAC | ACT | TTA | AAT | AAG | ATA | 1691 |
| Ser | Arg | Ala | Lys | Trp | Asn | Asp | Thr | Leu | Asn | Lys | Ile | |
| | | | 340 | | | | | 345 | | | | |

| GTT | ATA | AAA | TTA | AGA | GAA | CAA | TTT | GGG | AAT | AAA | ACA | 1727 |
| Val | Ile | Lys | Leu | Arg | Glu | Gln | Phe | Gly | Asn | Lys | Thr | |
| 350 | | | | | 355 | | | | | 360 | | |

| ATA | GTC | TTT | AAG | CAC | TCC | TCA | GGA | GGG | GAC | CCA | GAA | 1763 |
| Ile | Val | Phe | Lys | His | Ser | Ser | Gly | Gly | Asp | Pro | Glu | |
| | | | | 365 | | | | | 370 | | | |

| ATT | GTG | ACG | CAC | AGT | TTT | AAT | TGT | GGA | GGG | GAA | TTT | 1799 |
| Ile | Val | Thr | His | Ser | Phe | Asn | Cys | Gly | Gly | Glu | Phe | |
| | | 375 | | | | | 380 | | | | | |

| TTC | TAC | TGT | AAT | TCA | ACA | CAA | CTG | TTT | AAT | AGT | ACT | 1835 |
| Phe | Tyr | Cys | Asn | Ser | Thr | Gln | Leu | Phe | Asn | Ser | Thr | |
| 385 | | | | | 390 | | | | | 395 | | |

| TGG | AAT | GTT | ACT | GAA | GAG | TCA | AAT | AAC | ACT | GTA | GAA | 1871 |
| Trp | Asn | Val | Thr | Glu | Glu | Ser | Asn | Asn | Thr | Val | Glu | |
| | | | 400 | | | | | 405 | | | | |

| AAT | AAC | ACA | ATC | ACA | CTC | CCA | TGC | AGA | ATA | AAA | CAA | 1907 |
| Asn | Asn | Thr | Ile | Thr | Leu | Pro | Cys | Arg | Ile | Lys | Gln | |
| 410 | | | | | 415 | | | | | 420 | | |

| ATT | ATA | AAC | ATG | TGG | CAG | GAA | GTA | GGA | AGA | GCA | ATG | 1943 |
| Ile | Ile | Asn | Met | Trp | Gln | Glu | Val | Gly | Arg | Ala | Met | |
| | | | | 425 | | | | | 430 | | | |

| TAT | GCC | CCT | CCC | ATC | AGA | GGA | CAA | ATT | AGA | TGT | TCA | 1979 |
| Tyr | Ala | Pro | Pro | Ile | Arg | Gly | Gln | Ile | Arg | Cys | Ser | |
| | | 435 | | | | | 440 | | | | | |

| TCA | AAT | ATT | ACA | GGG | CTG | CTA | TTA | ACA | AGA | GAT | GGT | 2015 |
| Ser | Asn | Ile | Thr | Gly | Leu | Leu | Leu | Thr | Arg | Asp | Gly | |
| 445 | | | | | 450 | | | | | 455 | | |

| GGT | CCT | GAG | GAC | AAC | AAG | ACC | GAG | GTC | TTC | AGA | CCT | 2051 |
| Gly | Pro | Glu | Asp | Asn | Lys | Thr | Glu | Val | Phe | Arg | Pro | |
| | | | 460 | | | | | 465 | | | | |

| GGA | GGA | GGA | GAT | ATG | AGG | GAT | AAT | TGG | AGA | AGT | GAA | 2087 |
| Gly | Gly | Gly | Asp | Met | Arg | Asp | Asn | Trp | Arg | Ser | Glu | |
| | | 470 | | | | | 475 | | | | 480 | |

| TTA | TAT | AAA | TAT | AAA | GTA | GTA | AAA | ATT | GAA | CCA | TTA | 2123 |
| Leu | Tyr | Lys | Tyr | Lys | Val | Val | Lys | Ile | Glu | Pro | Leu | |
| | | | | 485 | | | | | 490 | | | |

| | | | | | | | | | | | |
|---|---|---|---|---|---|---|---|---|---|---|---|
| GGA | GTA | GCA | CCC | ACC | AAG | GCA | AAG | AGA | AGA | GTG | GTG | 2159 |
| Gly | Val | Ala | Pro | Thr | Lys | Ala | Lys | Arg | Arg | Val | Val | |
| | | 495 | | | | | 500 | | | | | |
| CAG | AGA | GAA | AAA | AGA | GCA | GTG | GGA | ATA | GGA | GCT | GTG | 2195 |
| Gln | Arg | Glu | Lys | Arg | Ala | Val | Gly | Ile | Gly | Ala | Val | |
| 505 | | | | | 510 | | | | | 515 | | |
| TTC | CTT | GGG | TTC | TTG | GGA | GCA | GCA | GGA | AGC | ACT | ATG | 2231 |
| Phe | Leu | Gly | Phe | Leu | Gly | Ala | Ala | Gly | Ser | Thr | Met | |
| | | | 520 | | | | | 525 | | | | |
| GGC | GCA | GCG | GCA | ATG | ACG | CTG | ACG | GTA | CAG | GCC | AGA | 2267 |
| Gly | Ala | Ala | Ala | Met | Thr | Leu | Thr | Val | Gln | Ala | Arg | |
| | | 530 | | | | 535 | | | | | 540 | |
| CTA | TTA | TTG | TCT | GGT | ATA | GTG | CAA | CAG | CAG | AAC | AAT | 2303 |
| Leu | Leu | Leu | Ser | Gly | Ile | Val | Gln | Gln | Gln | Asn | Asn | |
| | | | | | 545 | | | | | 550 | | |
| CTG | CTG | AGG | GCT | ATT | GAG | GCG | CAA | CAG | CAT | CTG | TTG | 2339 |
| Leu | Leu | Arg | Ala | Ile | Glu | Ala | Gln | Gln | His | Leu | Leu | |
| | | | 555 | | | | | 560 | | | | |
| CAA | CTC | ACA | GTC | TGG | GGC | ATC | AAG | CAG | CTC | CAG | GCA | 2375 |
| Gln | Leu | Thr | Val | Trp | Gly | Ile | Lys | Gln | Leu | Gln | Ala | |
| 565 | | | | | 570 | | | | | 575 | | |
| AGA | GTC | CTG | GCT | GTG | GAA | AGA | TAC | CTA | AGG | GAT | CAA | 2411 |
| Arg | Val | Leu | Ala | Val | Glu | Arg | Tyr | Leu | Arg | Asp | Gln | |
| | | | | 580 | | | | | 585 | | | |
| CAG | CTC | CTG | GGG | ATT | TGG | GGT | TGC | TCT | GGA | AAA | CTC | 2447 |
| Gln | Leu | Leu | Gly | Ile | Trp | Gly | Cys | Ser | Gly | Lys | Leu | |
| | 590 | | | | | | 595 | | | | 600 | |
| ATC | TGC | ACC | ACT | GCT | GTG | CCT | TGG | AAT | GCT | AGT | TGG | 2483 |
| Ile | Cys | Thr | Thr | Ala | Val | Pro | Trp | Asn | Ala | Ser | Trp | |
| | | | | | 605 | | | | | 610 | | |
| AGT | AAT | AAA | TCT | CTG | AAT | AAG | ATT | TGG | GAT | AAC | ATG | 2519 |
| Ser | Asn | Lys | Ser | Leu | Asn | Lys | Ile | Trp | Asp | Asn | Met | |
| | | 615 | | | | | 620 | | | | | |
| ACC | TGG | ATA | GAG | TGG | GAC | AGA | GAA | ATT | AAC | AAT | TAC | 2555 |
| Thr | Trp | Ile | Glu | Trp | Asp | Arg | Glu | Ile | Asn | Asn | Tyr | |
| 625 | | | | | 630 | | | | | 635 | | |
| ACA | AGC | ATA | ATA | TAC | AGC | TTA | ATT | GAA | GAA | TCG | CAG | 2591 |
| Thr | Ser | Ile | Ile | Tyr | Ser | Leu | Ile | Glu | Glu | Ser | Gln | |
| | | | 640 | | | | | 645 | | | | |
| AAC | CAA | CAA | GAA | AAG | AAT | GAA | CAA | GAA | TTA | TTA | GAA | 2627 |
| Asn | Gln | Gln | Glu | Lys | Asn | Glu | Gln | Glu | Leu | Leu | Glu | |
| | 650 | | | | | 655 | | | | | 660 | |
| TTA | GAT | AAA | TGG | GCA | AGT | TTG | TGG | AAT | TGG | TTT | GAC | 2663 |
| Leu | Asp | Lys | Trp | Ala | Ser | Leu | Trp | Asn | Trp | Phe | Asp | |
| | | | | 665 | | | | | 670 | | | |
| ATA | ACA | AAA | TGG | CTG | TGG | TAT | ATA | AAA | ATA | TTC | ATA | 2699 |
| Ile | Thr | Lys | Trp | Leu | Trp | Tyr | Ile | Lys | Ile | Phe | Ile | |
| | | 675 | | | | | 680 | | | | | |
| ATG | ATA | GTA | GGA | GGC | TTG | ATA | GGT | TTA | AGA | ATA | GTT | 2735 |
| Met | Ile | Val | Gly | Gly | Leu | Ile | Gly | Leu | Arg | Ile | Val | |
| 685 | | | | | 690 | | | | | 695 | | |
| TTT | TCT | GTA | CTT | TCT | ATA | GTG | AAT | AGA | GTT | AGG | CAG | 2771 |
| Phe | Ser | Val | Leu | Ser | Ile | Val | Asn | Arg | Val | Arg | Gln | |
| | | | 700 | | | | | 705 | | | | |
| GGA | TAC | TCA | CCA | TTA | TCG | TTT | CAG | ACC | CAC | CTC | CCA | 2807 |
| Gly | Tyr | Ser | Pro | Leu | Ser | Phe | Gln | Thr | His | Leu | Pro | |
| | 710 | | | | | 715 | | | | | 720 | |
| TCC | TCG | AGG | GGA | CCC | GAC | AGG | CCC | GGA | GGA | ATC | GAA | 2843 |
| Ser | Ser | Arg | Gly | Pro | Asp | Arg | Pro | Gly | Gly | Ile | Glu | |
| | | | | 725 | | | | | 730 | | | |

| | | | | | | | | | | | | |
|---|---|---|---|---|---|---|---|---|---|---|---|---|
| GAA | GAA | GGT | GGA | GAG | AGA | GAC | AGA | GAC | AGA | TCC | GGT | 2879 |
| Glu | Glu | Gly | Gly | Glu | Arg | Asp | Arg | Asp | Arg | Ser | Gly | |
| | | 735 | | | | 740 | | | | | | |
| CCA | TTA | GTG | AAC | GGA | TTC | TTG | GCG | CTT | ATC | TGG | GTC | 2915 |
| Pro | Leu | Val | Asn | Gly | Phe | Leu | Ala | Leu | Ile | Trp | Val | |
| 745 | | | | | 750 | | | | | 755 | | |
| GAT | CTG | CGG | AGC | CTG | TTC | CTC | TTC | AGC | TAC | CAC | CGC | 2951 |
| Asp | Leu | Arg | Ser | Leu | Phe | Leu | Phe | Ser | Tyr | His | Arg | |
| | | | 760 | | | | | 765 | | | | |
| TTG | AGA | GAC | TTA | CTC | TTG | ATT | GTG | ATG | AGG | ATT | GTG | 2987 |
| Leu | Arg | Asp | Leu | Leu | Leu | Ile | Val | Met | Arg | Ile | Val | |
| | 770 | | | | | 775 | | | | | 780 | |
| GAA | CTT | CTG | GGA | CTA | GCA | GGG | GGG | TGG | GAA | GTC | CTC | 3023 |
| Glu | Leu | Leu | Gly | Leu | Ala | Gly | Gly | Trp | Glu | Val | Leu | |
| | | | | 785 | | | | | 790 | | | |
| AAA | TAT | TGG | TGG | AAT | CTC | CTA | CAG | TAT | TGG | AGT | CAG | 3059 |
| Lys | Tyr | Trp | Trp | Asn | Leu | Leu | Gln | Tyr | Trp | Ser | Gln | |
| | | | 795 | | | | 800 | | | | | |
| GAA | CTA | AAG | AAT | AGT | GCT | GTT | AGC | TTG | CTC | AAT | GCC | 3095 |
| Glu | Leu | Lys | Asn | Ser | Ala | Val | Ser | Leu | Leu | Asn | Ala | |
| 805 | | | | | 810 | | | | | 815 | | |
| ACA | GCT | GTA | GCA | GTA | GCT | GAA | GGG | ACA | GAT | AGG | GTT | 3131 |
| Thr | Ala | Val | Ala | Val | Ala | Glu | Gly | Thr | Asp | Arg | Val | |
| | | | 820 | | | | | 825 | | | | |
| ATA | GAA | GTA | TTA | CAG | AGA | GCT | GTT | AGA | GCT | ATT | CTC | 3167 |
| Ile | Glu | Val | Leu | Gln | Arg | Ala | Val | Arg | Ala | Ile | Leu | |
| | 830 | | | | | 835 | | | | | 840 | |
| CAC | ATA | CCT | AGA | AGA | ATA | AGA | CAG | GGC | TTG | GAA | AGG | 3203 |
| His | Ile | Pro | Arg | Arg | Ile | Arg | Gln | Gly | Leu | Glu | Arg | |
| | | | | 845 | | | | | 850 | | | |
| GCT | TTG | CTA | | | | | | | | | | 3212 |
| Ala | Leu | Leu | | | | | | | | | | |
| | | 855 | | | | | | | | | | |

| | | | | |
|---|---|---|---|---|
| TAAGATGGGT | GGCAAGTGGT | CAAAAAGTAG | TATAGTCGTA | 3252 |
| TGGCCTGCTG | TAAGGAAAAG | AATGAGAAGA | ACTGAGCCAG | 3292 |
| CAGCAGATGG | AGTAGGAGCA | GTATCTAGAG | ACCTGGAAAA | 3332 |
| ACATGGAGCA | ATCACAAGTA | GCAATACAGC | AGCTAACAAT | 3372 |
| GCTGATTGTG | CCTGGCTAGA | AGCACAAGAG | GATGAAGAAG | 3412 |
| TGGGTTTTCC | AGTCAGACCT | CAGGTACCTT | TAAGACCAAT | 3452 |
| GACTCGCAGT | GCAGCTATAG | ATCTTAGCCA | CTTTTTTAAG | 3492 |
| AAAAAGGGGG | GACTGGAAGG | GCTAATTCAC | TCCCAAAAAA | 3532 |
| GACAAGATAT | CCTTGATTTG | TGGGTCTACC | ACACACAAGG | 3572 |
| CTACTTCCCT | GATTGGCAGA | ACTACACACC | AGGGCCAGGG | 3612 |
| ACCAGATTTC | CACTGACCTT | TGGATGGTGC | TTCAAGCTAG | 3652 |
| TACCAGTTGA | GCCAGAGAAG | GTAGAAGAGG | CCAATGAAGG | 3692 |
| AGAGAACAAC | TGCTTGTCAC | ACCCTATGAG | CCTGCATGGG | 3732 |
| ATGGATGACC | CGGAGAAAGA | AGTGTTAGCA | TGGAAGTTTG | 3772 |
| ACAGCAGCCT | AGCATTCCAT | CACGTGGCCC | GAGAA | 3807 |

( 2 ) INFORMATION FOR SEQ ID NO:6:

( i ) SEQUENCE CHARACTERISTICS:
        ( A ) LENGTH: 855 amino acids
        ( B ) TYPE: amino acid ( D ) TOPOLOGY: linear ( i i ) MOLECULE TYPE: protein ( x i ) SEQUENCE DESCRIPTION: SEQ ID NO:6:

```
Met Arg Val Thr Glu Ile Arg Lys Ser Tyr Gln His
 1               5                  10

Trp Trp Arg Trp Gly Ile Met Leu Leu Gly Ile Leu
        15              20

Met Ile Cys Asn Ala Glu Glu Lys Leu Trp Val Thr
25              30                  35

Val Tyr Tyr Gly Val Pro Val Trp Lys Glu Ala Thr
            40              45

Thr Thr Leu Phe Cys Ala Ser Asp Arg Lys Ala Tyr
    50              55                      60

Asp Thr Glu Val His Asn Val Trp Ala Thr His Ala
                65              70

Cys Val Pro Thr Asp Pro Asn Pro Gln Glu Val Glu
            75              80

Leu Lys Asn Val Thr Glu Asn Phe Asn Met Trp Lys
85                  90                  95

Asn Asn Met Val Glu Gln Met His Glu Asp Ile Ile
                100             105

Ser Leu Trp Asp Gln Ser Leu Lys Pro Cys Val Lys
    110             115                     120

Leu Thr Pro Leu Cys Val Thr Leu Asn Cys Thr Asp
            125                     130

Leu Arg Asn Ala Thr Asn Gly Asn Asp Thr Asn Thr
        135             140

Thr Ser Ser Ser Arg Gly Met Val Gly Gly Gly Glu
145                 150                     155

Met Lys Asn Cys Ser Phe Asn Ile Thr Thr Asn Ile
            160                     165

Arg Gly Lys Val Gln Lys Glu Tyr Ala Leu Phe Tyr
    170                 175                 180

Lys Leu Asp Ile Ala Pro Ile Asp Asn Asn Ser Asn
                185                 190

Asn Arg Tyr Arg Leu Ile Ser Cys Asn Thr Ser Val
        195                 200

Ile Thr Gln Ala Cys Pro Lys Val Ser Phe Glu Pro
205                 210                     215

Ile Pro Ile His Tyr Cys Ala Pro Ala Gly Phe Ala
            220                 225

Ile Leu Lys Cys Lys Asp Lys Lys Phe Asn Gly Lys
    230                 235                 240

Gly Pro Cys Thr Asn Val Ser Thr Val Gln Cys Thr
                245                 250

His Gly Ile Arg Pro Val Val Ser Thr Gln Leu Leu
        255                 260

Leu Asn Gly Ser Leu Ala Glu Glu Glu Val Val Ile
265                 270                     275

Arg Ser Ala Asn Phe Ala Asp Asn Ala Lys Val Ile
            280                 285

Ile Val Gln Leu Asn Glu Ser Val Glu Ile Asn Cys
    290                 295                 300
```

```
Thr  Arg  Pro  Asn  Asn  Asn  Thr  Arg  Lys  Ser  Ile  His
                    305                 310

Ile  Gly  Pro  Gly  Arg  Ala  Phe  Tyr  Thr  Thr  Gly  Glu
          315                 320

Ile  Ile  Gly  Asp  Ile  Arg  Gln  Ala  His  Cys  Asn  Leu
325                 330                      335

Ser  Arg  Ala  Lys  Trp  Asn  Asp  Thr  Leu  Asn  Lys  Ile
               340                 345

Val  Ile  Lys  Leu  Arg  Glu  Gln  Phe  Gly  Asn  Lys  Thr
          350                 355                      360

Ile  Val  Phe  Lys  His  Ser  Ser  Gly  Gly  Asp  Pro  Glu
                    365                      370

Ile  Val  Thr  His  Ser  Phe  Asn  Cys  Gly  Gly  Glu  Phe
               375                 380

Phe  Tyr  Cys  Asn  Ser  Thr  Gln  Leu  Phe  Asn  Ser  Thr
385                      390                      395

Trp  Asn  Val  Thr  Glu  Glu  Ser  Asn  Asn  Thr  Val  Glu
                    400                 405

Asn  Asn  Thr  Ile  Thr  Leu  Pro  Cys  Arg  Ile  Lys  Gln
          410                 415                      420

Ile  Ile  Asn  Met  Trp  Gln  Glu  Val  Gly  Arg  Ala  Met
                    425                      430

Tyr  Ala  Pro  Pro  Ile  Arg  Gly  Gln  Ile  Arg  Cys  Ser
          435                      440

Ser  Asn  Ile  Thr  Gly  Leu  Leu  Leu  Thr  Arg  Asp  Gly
445                           450                 455

Gly  Pro  Glu  Asp  Asn  Lys  Thr  Glu  Val  Phe  Arg  Pro
               460                      465

Gly  Gly  Gly  Asp  Met  Arg  Asp  Asn  Trp  Arg  Ser  Glu
          470                      475                 480

Leu  Tyr  Lys  Tyr  Lys  Val  Val  Lys  Ile  Glu  Pro  Leu
                    485                      490

Gly  Val  Ala  Pro  Thr  Lys  Ala  Lys  Arg  Arg  Val  Val
          495                      500

Gln  Arg  Glu  Lys  Arg  Ala  Val  Gly  Ile  Gly  Ala  Val
505                      510                      515

Phe  Leu  Gly  Phe  Leu  Gly  Ala  Ala  Gly  Ser  Thr  Met
               520                      525

Gly  Ala  Ala  Ala  Met  Thr  Leu  Thr  Val  Gln  Ala  Arg
          530                 535                      540

Leu  Leu  Leu  Ser  Gly  Ile  Val  Gln  Gln  Gln  Asn  Asn
               545                      550

Leu  Leu  Arg  Ala  Ile  Glu  Ala  Gln  Gln  His  Leu  Leu
          555                      560

Gln  Leu  Thr  Val  Trp  Gly  Ile  Lys  Gln  Leu  Gln  Ala
565                      570                      575

Arg  Val  Leu  Ala  Val  Glu  Arg  Tyr  Leu  Arg  Asp  Gln
               580                      585

Gln  Leu  Leu  Gly  Ile  Trp  Gly  Cys  Ser  Gly  Lys  Leu
          590                      595                 600

Ile  Cys  Thr  Thr  Ala  Val  Pro  Trp  Asn  Ala  Ser  Trp
                    605                      610

Ser  Asn  Lys  Ser  Leu  Asn  Lys  Ile  Trp  Asp  Asn  Met
```

|     |     |     | 615 |     |     |     | 620 |     |     |
| --- | --- | --- | --- | --- | --- | --- | --- | --- | --- |
| Thr 625 | Trp | Ile | Glu | Trp | Asp 630 | Arg | Glu | Ile | Asn | Asn 635 | Tyr |
| Thr | Ser | Ile | Ile 640 | Tyr | Ser | Leu | Ile | Glu 645 | Glu | Ser | Gln |
| Asn | Gln 650 | Gln | Glu | Lys | Asn | Glu 655 | Gln | Glu | Leu | Leu | Glu 660 |
| Leu | Asp | Lys | Trp | Ala 665 | Ser | Leu | Trp | Asn | Trp 670 | Phe | Asp |
| Ile | Thr | Lys 675 | Trp | Leu | Trp | Tyr | Ile 680 | Lys | Ile | Phe | Ile |
| Met 685 | Ile | Val | Gly | Gly | Leu 690 | Ile | Gly | Leu | Arg | Ile 695 | Val |
| Phe | Ser | Val | Leu 700 | Ser | Ile | Val | Asn | Arg 705 | Val | Arg | Gln |
| Gly | Tyr 710 | Ser | Pro | Leu | Ser | Phe 715 | Gln | Thr | His | Leu | Pro 720 |
| Ser | Ser | Arg | Gly | Pro 725 | Asp | Arg | Pro | Gly | Gly 730 | Ile | Glu |
| Glu | Glu | Gly 735 | Gly | Glu | Arg | Asp | Arg 740 | Asp | Arg | Ser | Gly |
| Pro 745 | Leu | Val | Asn | Gly | Phe 750 | Leu | Ala | Leu | Ile | Trp 755 | Val |
| Asp | Leu | Arg | Ser 760 | Leu | Phe | Leu | Phe | Ser 765 | Tyr | His | Arg |
| Leu | Arg 770 | Asp | Leu | Leu | Leu | Ile 775 | Val | Met | Arg | Ile | Val 780 |
| Glu | Leu | Leu | Gly | Leu 785 | Ala | Gly | Gly | Trp | Glu 790 | Val | Leu |
| Lys | Tyr | Trp 795 | Trp | Asn | Leu | Leu | Gln 800 | Tyr | Trp | Ser | Gln |
| Glu 805 | Leu | Lys | Asn | Ser | Ala 810 | Val | Ser | Leu | Leu | Asn 815 | Ala |
| Thr | Ala | Val | Ala 820 | Val | Ala | Glu | Gly | Thr 825 | Asp | Arg | Val |
| Ile | Glu 830 | Val | Leu | Gln | Arg | Ala 835 | Val | Arg | Ala | Ile | Leu 840 |
| His | Ile | Pro | Arg | Arg 845 | Ile | Arg | Gln | Gly | Leu 850 | Glu | Arg |
| Ala | Leu | Leu 855 | | | | | | | | | |